United States Patent
Maeda et al.

(10) Patent No.: US 11,912,679 B2
(45) Date of Patent: Feb. 27, 2024

(54) ARYL ALKYNAMIDE DERIVATIVES

(71) Applicants: Astellas Pharma, Inc., Tokyo (JP); Mitobridge, Inc., Cambridge, MA (US)

(72) Inventors: Junko Maeda, Tokyo (JP); Ikumi Kuriwaki, Tokyo (JP); Kai Kitamura, Tokyo (JP); Yumi Yamashita, Tokyo (JP); Kenichi Kakefuda, Tokyo (JP); Akio Kamikawa, Tokyo (JP); Kenji Negoro, Tokyo (JP); Wataru Hamaguchi, Tokyo (JP); Ryushi Seo, Tokyo (JP); Jeffrey Ciavarri, Cambridge, MA (US)

(73) Assignees: Astellas Pharma, Inc., Tokyo (JP); Mitobridge, Inc., Cambridge, MA (US)

( * ) Notice: Subject to any disclaimer, the term of this patent is extended or adjusted under 35 U.S.C. 154(b) by 0 days.

(21) Appl. No.: 18/372,771

(22) Filed: Sep. 26, 2023

(65) Prior Publication Data
US 2024/0018113 A1    Jan. 18, 2024

Related U.S. Application Data

(63) Continuation of application No. PCT/US2023/013924, filed on Feb. 27, 2023.
(Continued)

(51) Int. Cl.
| | |
|---|---|
| C07C 233/69 | (2006.01) |
| C07C 233/22 | (2006.01) |
| C07C 233/81 | (2006.01) |
| C07C 235/42 | (2006.01) |
| C07C 237/42 | (2006.01) |
| C07C 311/13 | (2006.01) |
| C07C 311/46 | (2006.01) |
| C07D 205/04 | (2006.01) |
| C07D 207/12 | (2006.01) |
| C07D 207/16 | (2006.01) |
| C07D 207/273 | (2006.01) |
| C07D 209/08 | (2006.01) |
| C07D 211/48 | (2006.01) |
| C07D 211/62 | (2006.01) |
| C07D 213/56 | (2006.01) |
| C07D 213/75 | (2006.01) |
| C07D 231/12 | (2006.01) |
| C07D 231/40 | (2006.01) |
| C07D 239/26 | (2006.01) |
| C07D 279/12 | (2006.01) |
| C07D 295/155 | (2006.01) |
| C07D 295/16 | (2006.01) |
| C07D 295/195 | (2006.01) |
| C07D 305/08 | (2006.01) |
| C07D 307/22 | (2006.01) |

(Continued)

(52) U.S. Cl.
CPC .......... *C07D 295/16* (2013.01); *C07C 233/22* (2013.01); *C07C 233/69* (2013.01); *C07C 233/81* (2013.01); *C07C 235/42* (2013.01); *C07C 237/42* (2013.01); *C07C 311/13* (2013.01); *C07C 311/46* (2013.01); *C07D 205/04* (2013.01); *C07D 207/12* (2013.01); *C07D 207/16* (2013.01); *C07D 207/273* (2013.01); *C07D 209/08* (2013.01); *C07D 211/48* (2013.01); *C07D 211/62* (2013.01); *C07D 213/56* (2013.01); *C07D 213/75* (2013.01); *C07D 231/12* (2013.01); *C07D 231/40* (2013.01); *C07D 239/26* (2013.01); *C07D 279/12* (2013.01); *C07D 295/155* (2013.01); *C07D 295/195* (2013.01); *C07D 305/08* (2013.01); *C07D 307/22* (2013.01); *C07D 309/14* (2013.01); *C07D 333/48* (2013.01); *C07D 401/06* (2013.01); *C07D 403/06* (2013.01); *C07D 403/10* (2013.01); *C07D 405/10* (2013.01); *C07D 487/10* (2013.01)

(58) Field of Classification Search
CPC .... C07C 233/22; C07C 233/69; C07D 295/16
See application file for complete search history.

(56) References Cited

U.S. PATENT DOCUMENTS

| 6,150,413 A | 11/2000 | Bernardon et al. |
| 2007/0299114 A1* | 12/2007 | Kugimiya ............... C07C 57/42 514/427 |

FOREIGN PATENT DOCUMENTS

| WO | 2005/115990 A1 | 12/2005 |
| WO | 2019/122202 A1 | 6/2019 |

(Continued)

OTHER PUBLICATIONS

Hwang et al., Palladium-Catalyzed Oxidative Aminocarbonylation by Decarboxylative Coupling: Synthesis of Alkynyl Amides. Eur J Org Chem. 2015;2235-2243.

(Continued)

*Primary Examiner* — Samantha L Shterengarts
*Assistant Examiner* — Karen Cheng
(74) *Attorney, Agent, or Firm* — McCarter & English, LLP; Wei Song; James M. Alburger

(57) ABSTRACT

[Problem] A compound which is useful as a STING inhibitor is provided.
[Means for Solution] The present inventors have found aryl alkynamide derivatives having an inhibitory action on STING. The aryl alkynamide derivatives of the present invention have an inhibitory action on STING and can be used as an agent for treating an autoimmune disease, a neurodegenerative disease, a type I interferonopathy and/or other STING-mediated disease.

19 Claims, 3 Drawing Sheets

Related U.S. Application Data

(60) Provisional application No. 63/314,783, filed on Feb. 28, 2022.

(51) Int. Cl.
*C07D 309/14* (2006.01)
*C07D 333/48* (2006.01)
*C07D 401/06* (2006.01)
*C07D 403/06* (2006.01)
*C07D 403/10* (2006.01)
*C07D 405/10* (2006.01)
*C07D 487/10* (2006.01)

(56) References Cited

FOREIGN PATENT DOCUMENTS

| WO | 2019/182886 A1 | 9/2019 |
|---|---|---|
| WO | 2020/106741 A1 | 5/2020 |
| WO | 2020/150417 A2 | 7/2020 |
| WO | 2021/068950 A1 | 4/2021 |

OTHER PUBLICATIONS

Lepailleur et al., Receptor- and ligand-based study on novel 2,2'-bithienyl derivatives as non-peptidic AANAT inhibitors. J Chem Inf Model. Mar. 22, 2010;50(3):446-60.

Pan et al., Selenium Radical-Triggered Spiro-Tricyclization of N-Aryl-N-(2-hydroxyethyl)propiolamides. Synthesis. 2022;54(13):3105-3113.

Yasui et al., Sc(OTf)3-Catalyzed Iodocyclization/Ritter-Type Amidation of N-Alkoxypropiolamides: A Synthetic Strategy for Isoxazol-3(2H)-ones. J Org Chem. Nov. 5, 2021;86(21):15498-15508. Supporting information.

International Search Report and Written Opinion for Application No. PCT/US2023/013924, dated May 17, 2023, 13 pages.

* cited by examiner

[Fig. 1]
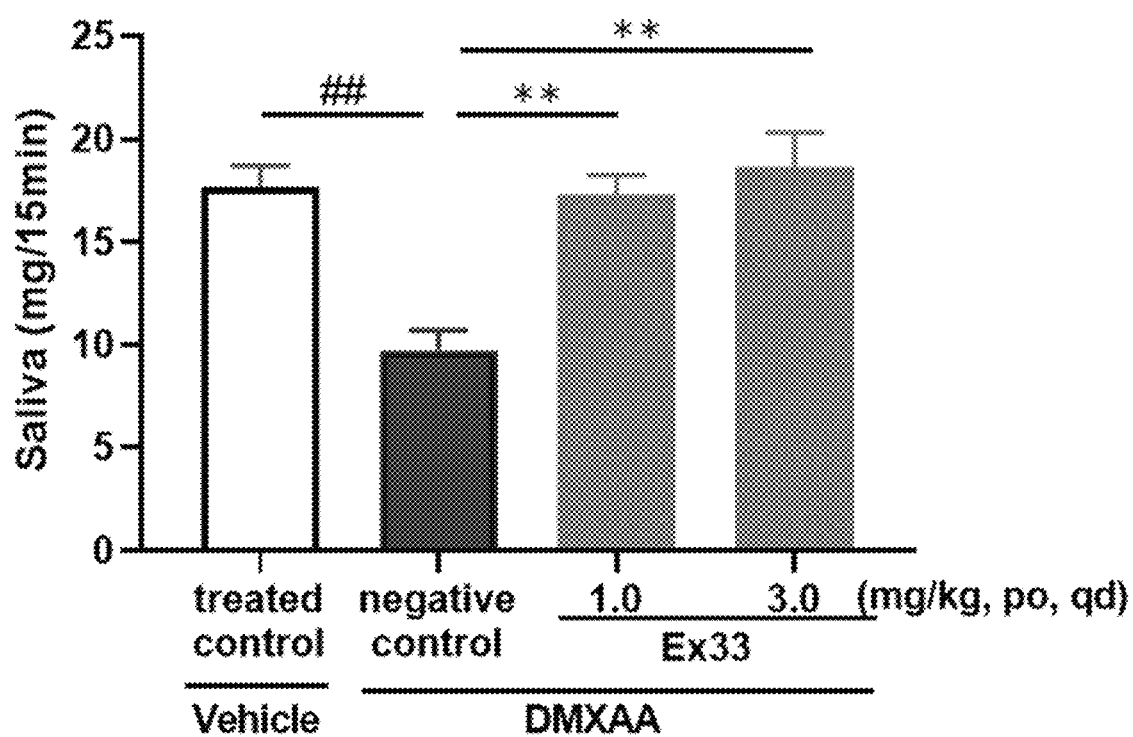
n = 10, mean value ± SEM
; P < 0.01, Student's t-test
**; P < 0.01, Dunnett's multiple comparison test

[Fig. 2]
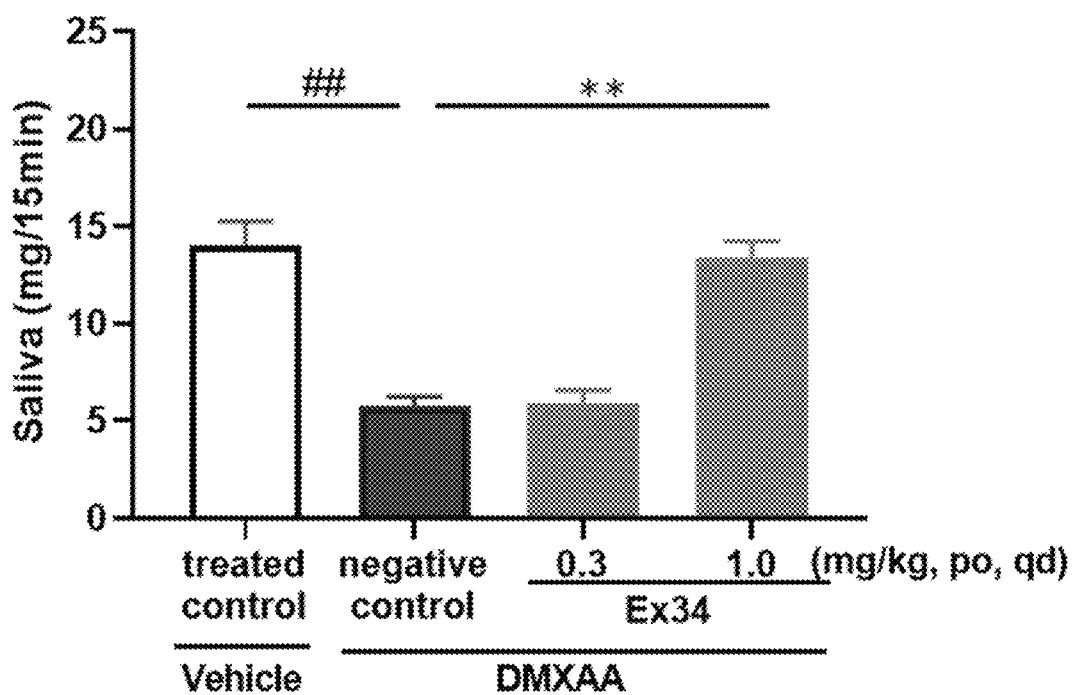

[Fig. 3]
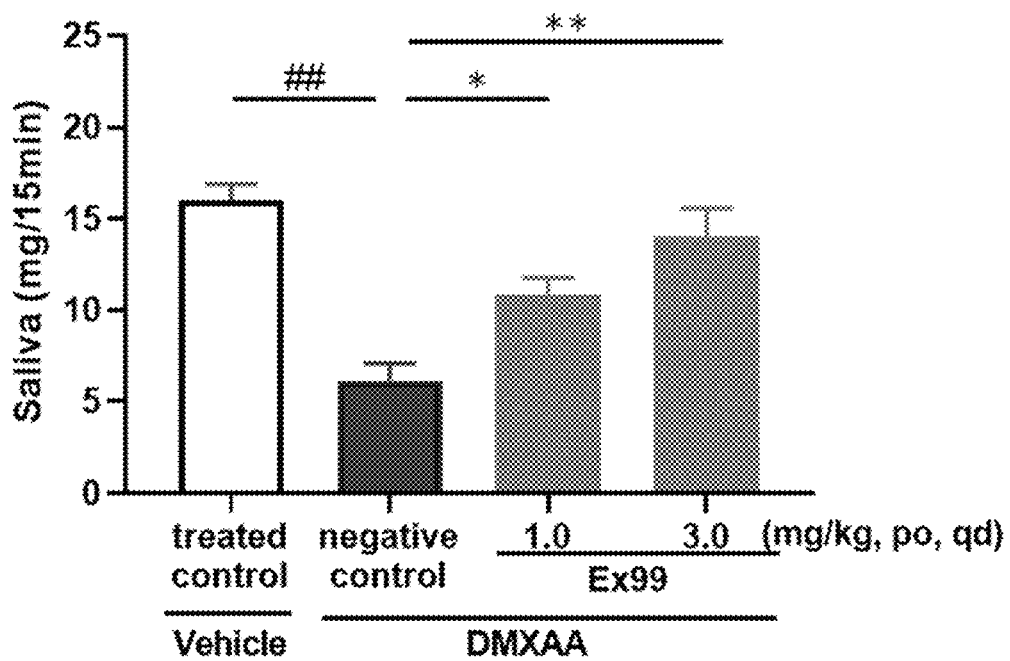
n = 10, mean value ± SEM
; P < 0.01, Student's t-test
*; P < 0.05, **; P < 0.01, Dunnett's multiple comparison test

ARYL ALKYNAMIDE DERIVATIVES

CROSS REFERENCE TO RELATED APPLICATIONS

This application is a continuation application of International Application No. PCT/US2023/13924, filed Feb. 27, 2023, which in turn claims priority to U.S. Provisional Application No. 63/314,783, filed Feb. 28, 2022. The entire contents of each of the foregoing applications are included herein by reference.

TECHNICAL FIELD

The present invention relates to aryl alkynamide derivatives which are useful as a Stimulator of Interferon Genes (STING) inhibitor and are expected to be useful as an active ingredient of a pharmaceutical composition, for example, a pharmaceutical composition for treating an autoimmune disease, a neurodegenerative disease, a type I interferonopathy and/or other STING-mediated disease.

BACKGROUND ART

STING is an adaptor protein that is widely expressed in immune cells and is involved in immune responses. When endogenous and exogenous double strand DNA (dsDNA) in the cytoplasm is recognized by cyclic GMP-AMP (cGAMP) synthase (cGAS), a DNA sensor, through the production of a second messenger cGAMP, STING serves as a mediator of inflammation leading to secretion of pro-inflammatory cytokines, such as type-I interferon (IFN) as well as downstream cytokines of nuclear factor-kappa B (NF-kB).

The cGAS-STING pathway plays an important role in host defense against viral infections, but the accumulation of endogenous dsDNA in the cytoplasm or gain-of-function mutations in the STING can lead to excessive immune responses that are known to cause type I interferonopathy including Aicardi-Goutieres syndrome (AGS) and STING-associated vasculopathy with onset in infancy (SAVI). In addition, activation of the cGAS-STING pathway or increase of its ligands have been reported in a wide variety of diseases such as systemic lupus erythematosus (Annals of the Rheumatic Diseases, Vol. 77, No. 10, p. 1507-1515, 2018), Sjogren's syndrome (Journal of Autoimmunity, Vol. 108, Article No. 102381, 2020), Crohn's disease (Cell Death and Disease, Vol. 12, Article No. 815, 2021), amyotrophic lateral sclerosis (Cell, Volume 183, Issue 3, p. 636-649, 2020) and Huntington's disease (PNAS, Vol. 117, No. 27, p. 15989-15999, 2020).

Patent Document 1 discloses that a compound represented by the following formula has an inhibitory activity on the STING pathway and is useful for treating a condition, disease or disorder in which increased STING pathway activation contributes to the pathology and/or symptoms and/or progression of the condition, disease or disorder in a subject (for the symbols in the formula, refer to the patent document).

[Chem 1]

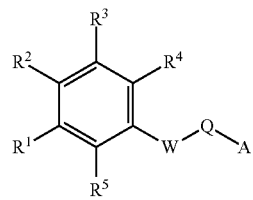

Patent Document 2 discloses that a compound represented by the following formula has an inhibitory activity on STING and is useful for treating a STING-associated disease, condition or disorder (for the symbols in the formula, refer to the patent document).

[Chem 2]

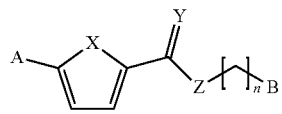

Patent Document 3 discloses that a compound represented by the following formula has an inhibitory activity on STING and is useful for treating STING-mediated diseases (for the symbols in the formula, refer to the patent document).

[Chem 3]

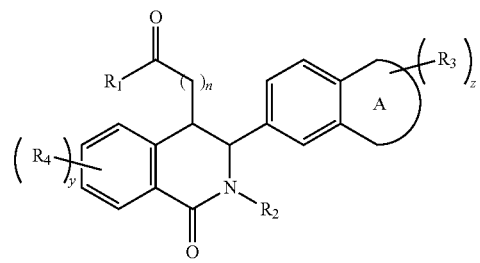

Patent Document 4 discloses that a compound represented by the following formula has an inhibitory activity on production of amyloid beta and is useful for treating neurodegenerative diseases resulting from amyloid beta (in which $X_1$ represents acetylene group or the like, and $Ar_1$ represents optionally substituted imidazolyl or the like. For the other symbols in the formula, refer to the patent document). However, any inhibitory activity on STING is not described.

[Chem 4]

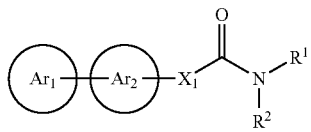

Patent Document 5 discloses that a compound represented by the following formula has an antagonistic activity on retinoic acid receptor (RAR) and is useful for treating a wide variety of disease states, for example dermatological, rheumatic, respiratory, cardiovascular, bone and ophthalmological disorders (in which X-Y represents alkynamide group or the like. For the other symbols in the formula, refer to the patent document). However, any inhibitory activity on STING is not described.

[Chem 5]

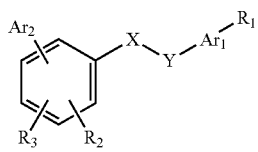

Non-Patent Document 1 discloses that a compound represented by the following formula has an inhibitory activity on arylalkylamine N-acetyl transferase (AANAT) (in which R represents amines). However, any inhibitory activity on STING is not described.

[Chem 6]

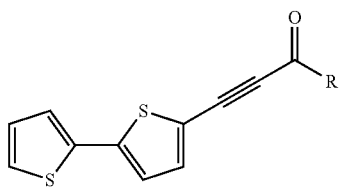

Non-Patent Document 2 discloses a compound represented by the following formula as a resultant of aminocarbonylation reaction. However, any inhibitory activity on STING is not described.

[Chem 7]

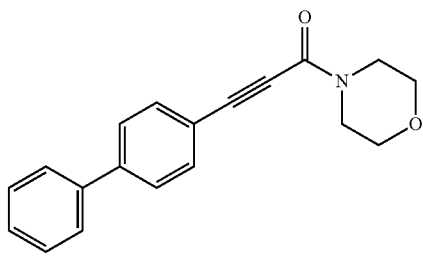

Non-Patent Document 3 discloses a compound represented by the following formula as a starting material of iodocyclization reaction. However, any inhibitory activity on STING is not described.

[Chem 8]

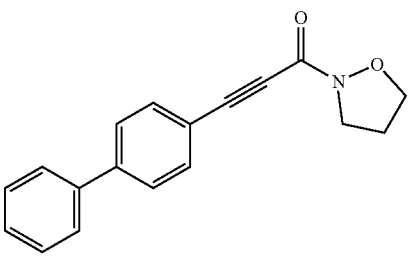

Non-Patent Document 4 discloses a compound represented by the following formula as a starting material of spiro-tricyclization reaction. However, any inhibitory activity on STING is not described.

[Chem 9]

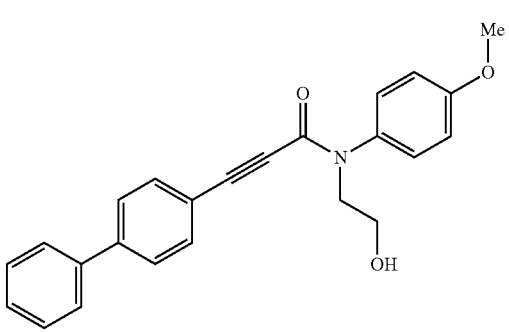

Patent Document

[Patent Document 1] International Publication WO 2020/106741
[Patent Document 2] International Publication WO 2019/122202
[Patent Document 3] International Publication WO 2019/182886
[Patent Document 4] International Publication WO 2005/115990
[Patent Document 5] U.S. Pat. No. 6,150,413

Non-Patent Document

[Non-Patent Document 1] Journal of Chemical Information and Modeling, 50, pp 446-460 (2010)
[Non-Patent Document 2] European Journal of Organic Chemistry, pp 2235-2243 (2015)
[Non-Patent Document 3] Journal of Organic Chemistry, 86, pp 15498-15508 (2021)
[Non-Patent Document 4] Synthesis, 54, pp 3105-3113 (2022)

DISCLOSURE OF INVENTION

Problems to be Solved by the Invention

A compound which is useful as STING inhibitor and is expected to be useful as an active ingredient of a pharmaceutical composition, for example, a pharmaceutical composition for treating an autoimmune disease, a neurodegenerative disease, a type I interferonopathy or other STING-mediated disease, is provided.

Means for Solving the Problems

The present inventors have extensively conducted studies on a compound having an inhibitory action on STING, and as a result, have found that an aryl alkynamide derivative has an inhibitory action on STING, and is expected to be useful as an active ingredient of a pharmaceutical composition for treating an autoimmune disease, a neurodegenerative disease, a type I interferonopathy and/or other STING-mediated disease or the like, particularly Sjogren's syndrome and systemic lupus erythematosus. In this way, the present invention has been attained.

The present invention relates to a compound of formula (I) or a salt thereof, and a pharmaceutical composition comprising a compound of formula (I) or a salt thereof and one or more pharmaceutically acceptable excipients.

[Chem 10]

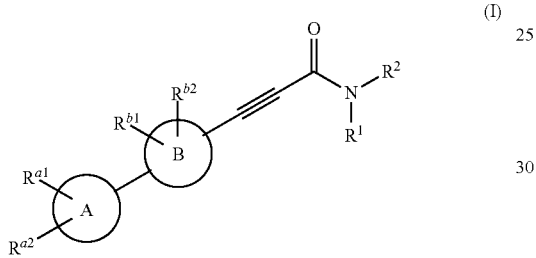

(I)

(wherein,

Ring A is phenyl which may be optionally fused with 5-membered heterocyclyl, 6-membered heteroaryl containing one or two nitrogen atoms, pyrazolyl or 6-membered saturated or partially unsaturated heterocyclyl, Ring B is phenyl which may be optionally fused with phenyl or 6-membered heteroaryl containing one or two nitrogen atoms, 6-membered heteroaryl containing one or two nitrogen atoms, pyrazolyl or imidazolyl, $R^{a1}$ and $R^{a2}$ are independently H, $C_{1-6}$ alkyl, —O—$C_{1-6}$ alkyl, —O—$C_{1-6}$ alkylene-$C_{2-6}$ alkenyl, —O—$C_{1-6}$ alkylene-$C_{2-6}$ alkynyl, halogen, halogeno-$C_{1-6}$ alkyl, —O-halogeno-$C_{1-6}$ alkyl or —OH, $R^{b1}$ and $R^{b2}$ are independently H, $C_{1-6}$ alkyl, —O—$C_{1-6}$ alkyl, halogeno-$C_{1-6}$ alkyl, —O-halogeno-$C_{1-6}$ alkyl, halogen, —$C_{1-6}$ alkylene-OH, —$C_{1-6}$ alkylene-$NR^cR^d$, —C(=O)—$NR^cR^d$, —$NR^cR^d$, —CN or —OH, $R^c$ and $R^d$ are independently H, $C_{1-6}$ alkyl, $C_{3-8}$ cycloalkyl, —C(=O)—$C_{1-6}$ alkyl, or —S(=O)$_2$—$C_{1-6}$ alkyl, or, $R^c$ and $R^d$ may be optionally linked to each other to form 4- to 7-membered saturated heterocyclyl together with the nitrogen atom to which $R^c$ and $R^d$ are attached, wherein the heterocyclyl may be optionally substituted with one or two $R^e$, $R^e$ is $C_{1-6}$ alkyl, —O—$C_{1-6}$ alkyl or halogen, $R^1$ is H, optionally substituted $C_{1-6}$ alkyl, optionally substituted $C_{3-8}$ cycloalkyl, optionally substituted 4- to 7-membered saturated heterocyclyl, optionally substituted phenyl or optionally substituted heteroaryl, $R^2$ is $C_{1-6}$ alkyl which is substituted with one or two $R^3$, $C_{3-8}$ cycloalkyl which is substituted with one or two $R^4$, 4- to 7-membered saturated heterocyclyl which is substituted with one or two $R^5$, or phenyl which is substituted with one or two $R^6$, or, $R^1$ and $R^2$ are linked to each other to form 4- to 7-membered saturated heterocyclyl together with the nitrogen atom to which $R^1$ and $R^2$ are attached, wherein the heterocyclyl may be optionally fused with phenyl, and the heterocyclyl and/or the fused phenyl may be optionally substituted with one to three $R^7$, each $R^3$ is independently —OH, —O—$C_{1-6}$ alkyl, —C(=O)—$NH_2$, —C(=O)—NH—$C_{1-6}$ alkyl, —C(=O)—N($C_{1-6}$ alkyl)$_2$, —$NH_2$, —NH—$C_{1-6}$ alkyl, —N($C_{1-6}$ alkyl)$_2$, —NH—C(=O)—$C_{1-6}$ alkyl, —NH—S(=O)$_2$—$C_{1-6}$ alkyl, —NH—S(=O)$_2$—$C_{1-6}$ alkylene-OH, —NH—S(=O)$_2$—$C_{1-6}$ alkylene-C(=O)—OH, —S(=O)$_2$—$NH_2$, —S(=O)$_2$—$C_{1-6}$ alkyl or —S(=O)(=NH)—$C_{1-6}$ alkyl, each $R^4$ is independently —OH, —O—$C_{1-6}$ alkyl, —C(=O)—$NH_2$, —C(=O)—NH—$C_{1-6}$ alkyl, —C(=O)—N($C_{1-6}$ alkyl)$_2$, —$NH_2$, —NH—$C_{1-6}$ alkyl, —N($C_{1-6}$ alkyl)$_2$, —NH—C(=O)—$C_{1-6}$ alkyl, —NH—S(=O)$_2$—$C_{1-6}$ alkyl, —S(=O)$_2$—$NH_2$, —S(=O)$_2$—$C_{1-6}$ alkyl or —S(=O)(=NH)—$C_{1-6}$ alkyl, each $R^5$ is independently —OH, oxo or imino, each $R^6$ is independently —C(=O)—OH, —S(=O)$_2$—$NH_2$, —S(=O)$_2$—$C_{1-6}$ alkyl, —S(=O)(=NH)—$C_{1-6}$ alkyl or —NH—S(=O)$_2$—$C_{1-6}$ alkyl, and each $R^7$ is independently $C_{1-6}$ alkyl, —$C_{1-6}$ alkylene-OH, —$C_{1-6}$ alkylene-C(=O)—OH, $C_{3-8}$ cycloalkyl, —OH, —O—$C_{1-6}$ alkyl, —$NH_2$, —NH—$C_{1-6}$ alkyl, —N($C_{1-6}$ alkyl)$_2$, —NH—C(=O)—$C_{1-6}$ alkyl, —NH—S(=O)$_2$—$C_{1-6}$ alkyl, —S(=O)$_2$—$C_{1-6}$ alkyl, —S(=O)(=NH)—$C_{1-6}$ alkyl, —C(=O)—OH, —C(=O)—$NH_2$, —C(=O)—NH—$C_{1-6}$ alkyl, —C(=O)—N($C_{1-6}$ alkyl)$_2$, oxo, imino or 4- to 7-membered saturated heterocyclyl which may be optionally substituted with one or two oxo, provided that the compound of formula (I) is not the compound of formula (II), (III), (IV) or (IVa)).

[Chem 11]

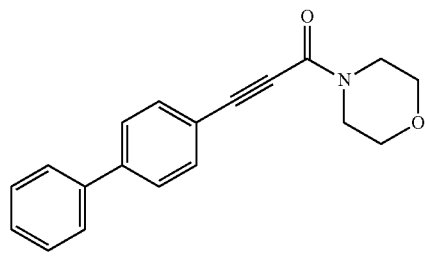

(II)

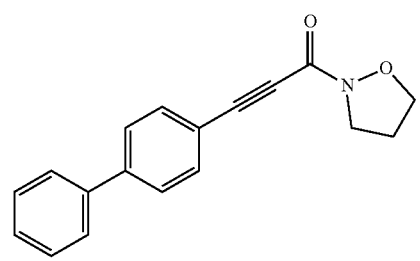

(III)

-continued (IV)

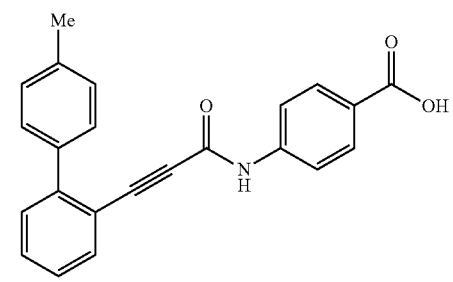

(IVa)

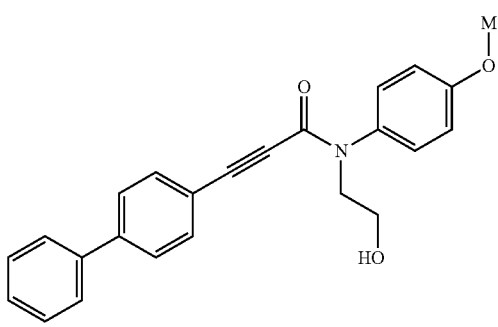

Further, unless specifically described otherwise, when symbols in one formula in the present specification are also used in other formulae, same symbols denote same meanings.

Further, the present invention relates to a pharmaceutical composition for treatment of an autoimmune disease, a neurodegenerative disease, a type I interferonopathy and/or other STING-mediated disease, comprising the compound of formula (I) or a salt thereof.

[Chem 12]

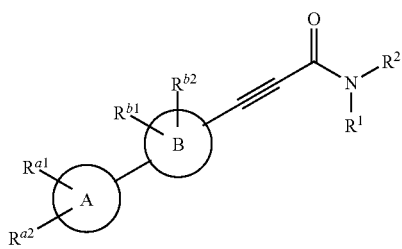

(I)

(wherein,

Ring A is phenyl which may be optionally fused with 5-membered heterocyclyl, 6-membered heteroaryl containing one or two nitrogen atoms, pyrazolyl or 6-membered saturated or partially unsaturated heterocyclyl, Ring B is phenyl which may be optionally fused with phenyl or 6-membered heteroaryl containing one or two nitrogen atoms, 6-membered heteroaryl containing one or two nitrogen atoms, pyrazolyl or imidazolyl, $R^{a1}$ and $R^{a2}$ are independently H, $C_{1-6}$ alkyl, —O—$C_{1-6}$ alkyl, —O—$C_{1-6}$ alkylene-$C_{2-6}$ alkenyl, —O—$C_{1-6}$ alkylene-$C_{2-6}$ alkynyl, halogen, halogeno-$C_{1-6}$ alkyl, —O-halogeno-$C_{1-6}$ alkyl or —OH, $R^{b1}$ and $R^{b2}$ are independently H, $C_{1-6}$ alkyl, —O—$C_{1-6}$ alkyl, halogeno-$C_{1-6}$ alkyl, —O-halogeno-$C_{1-6}$ alkyl, halogen, —$C_{1-6}$ alkylene-OH, —$C_{1-6}$ alkylene-$NR^cR^d$, —C(=O)—$NR^cR^d$, —$NR^cR^d$, —CN or —OH, $R^c$ and $R^d$ are independently H, $C_{1-6}$ alkyl, $C_{3-8}$ cycloalkyl, —C(=O)—$C_{1-6}$ alkyl, or —S(=O)$_2$—$C_{1-6}$ alkyl, or, $R^c$ and $R^d$ may be optionally linked to each other to form a 4- to 7-membered saturated heterocyclyl together with the nitrogen atom to which $R^c$ and $R^d$ are attached, wherein the heterocyclyl may be optionally substituted with one or two $R^e$, $R^e$ is $C_{1-6}$ alkyl, —O—$C_{1-6}$ alkyl or halogen, $R^1$ is H, optionally substituted $C_{1-6}$ alkyl, optionally substituted $C_{3-8}$ cycloalkyl, optionally substituted 4- to 7-membered saturated heterocyclyl, optionally substituted phenyl or optionally substituted heteroaryl, $R^2$ is $C_{1-6}$ alkyl which is substituted with one or two $R^3$, $C_{3-8}$ cycloalkyl which is substituted with one or two $R^4$, 4- to 7-membered saturated heterocyclyl which is substituted with one or two $R^5$, or phenyl which is substituted with one or two $R^6$, or, $R^1$ and $R^2$ are linked to each other to form 4- to 7-membered saturated heterocyclyl together with the nitrogen atom to which $R^1$ and $R^2$ are attached, wherein the heterocyclyl may be optionally fused with phenyl, and the heterocyclyl and/or the fused phenyl may be optionally substituted with one to three $R^7$, each $R^3$ is independently —OH, —O—$C_{1-6}$ alkyl, —C(=O)—$NH_2$, —C(=O)—NH—$C_{1-6}$ alkyl, —C(=O)—N($C_{1-6}$ alkyl)$_2$, —$NH_2$, —NH—$C_{1-6}$ alkyl, —N($C_{1-6}$ alkyl)$_2$, —NH—C(=O)—$C_{1-6}$ alkyl, —NH—S(=O)$_2$—$C_{1-6}$ alkyl, —NH—S(=O)$_2$—$C_{1-6}$ alkylene-OH, —NH—S(=O)$_2$—$C_{1-6}$ alkylene-C(=O)—OH, —S(=O)$_2$—$NH_2$, —S(=O)$_2$—$C_{1-6}$ alkyl or —S(=O)(=NH)—$C_{1-6}$ alkyl, each $R^4$ is independently —OH, —O—$C_{1-6}$ alkyl, —C(=O)—$NH_2$, —C(=O)—NH—$C_{1-6}$ alkyl, —C(=O)—N($C_{1-6}$ alkyl)$_2$, —$NH_2$, —NH—$C_{1-6}$ alkyl, —N($C_{1-6}$ alkyl)$_2$, —NH—C(=O)—$C_{1-6}$ alkyl, —NH—S(=O)$_2$—$C_{1-6}$ alkyl, —S(=O)$_2$—$NH_2$, —S(=O)$_2$—$C_{1-6}$ alkyl or —S(=O)(=NH)—$C_{1-6}$ alkyl, each $R^5$ is independently —OH, oxo or imino, each $R^6$ is independently —C(=O)—OH, —S(=O)$_2$—$NH_2$, —S(=O)$_2$—$C_{1-6}$ alkyl, —S(=O)(=NH)—$C_{1-6}$ alkyl or —NH—S(=O)$_2$—$C_{1-6}$ alkyl, and each $R^7$ is independently $C_{1-6}$ alkyl, —$C_{1-6}$ alkylene-OH, —$C_{1-6}$ alkylene-C(=O)—OH, $C_{3-8}$ cycloalkyl, —OH, —O—$C_{1-6}$ alkyl, —$NH_2$, —NH—$C_{1-6}$ alkyl, —N($C_{1-6}$ alkyl)$_2$, —NH—C(=O)—$C_{1-6}$ alkyl, —NH—S(=O)$_2$—$C_{1-6}$ alkyl, —S(=O)$_2$—$C_{1-6}$ alkyl, —S(=O)(=NH)—$C_{1-6}$ alkyl, —C(=O)—OH, —C(=O)—$NH_2$, —C(=O)—NH—$C_{1-6}$ alkyl, —C(=O)—N($C_{1-6}$ alkyl)$_2$, oxo, imino or 4- to 7-membered saturated heterocyclyl which may be optionally substituted with one or two oxo.)

Here, the pharmaceutical composition includes an agent for treatment of an autoimmune disease, a neurodegenerative disease, a type I interferonopathy and/or other STING-mediated disease, comprising the compound of formula (I) or a salt thereof.

Furthermore, the present invention relates to a compound of formula (I) or salt thereof, which is a STING inhibitor; a compound of formula (I) or salt thereof for use as a STING inhibitor; a STING inhibitor comprising a compound of formula (I) or salt thereof; use of the compound of formula (I) or a salt thereof for the manufacture of a pharmaceutical composition for treatment of an autoimmune disease, a neurodegenerative disease, a type I interferonopathy and/or other STING-mediated disease; use of the compound of formula (I) or a salt thereof for treatment of an autoimmune disease, a neurodegenerative disease, a type I interferonopathy and/or the other STING-mediated disease; the compound of formula (I) or a salt thereof for use in treatment of an autoimmune disease, a neurodegenerative disease, a type I interferonopathy and/or other STING-mediated disease; and a method for treatment of an autoimmune disease, a neurodegenerative disease, a type I interferonopathy and/or the other STING-mediated disease, comprising administering to a subject an effective amount of the compound of formula (I) or a salt thereof.

Here, the "subject" is a human or a non-human animal in need of the treatment, and in one embodiment, a human in need of the treatment.

Effects of the Invention

The compound of formula (I) or a salt thereof has a STING inhibitory action and can be used as an agent for treatment of an autoimmune disease, a neurodegenerative disease, a type I interferonopathy and/or other STING-mediated disease.

BRIEF DESCRIPTION OF THE DRAWINGS

FIG. 1 shows results of the saliva production which evaluates an improving effect of the compound of the Example 33 on salivary disfunction in mice drug-induced Sjogren's syndrome-like model. Data are expressed as mean±SEM. The statistical significance between vehicle-treated control group and DMXAA-treated negative control group was determined using Student's t-test. ##represents P<0.01. The statistical significances between groups treated with DMXAA were determined using Dunnett's multiple comparison test. ** represents P<0.01. Quaque die (QD) represents a once-daily dosing.

FIG. 2 shows results of the saliva production which evaluates an improving effect of the compound of the Example 34 on salivary disfunction in mice drug-induced Sjogren's syndrome-like model. Data are expressed as mean±SEM. The statistical significance between vehicle-treated control group and DMXAA-treated negative control group was determined using Student's t-test. ##represents P<0.01. The statistical significances between groups treated with DMXAA were determined using Dunnett's multiple comparison test. ** represents P<0.01. Quaque die (QD) represents a once-daily dosing.

FIG. 3 shows results of the saliva production which evaluates an improving effect of the compound of the Example 99 on salivary disfunction in mice drug-induced Sjogren's syndrome-like model. Data are expressed as mean±SEM. The statistical significance between vehicle-treated control group and DMXAA-treated negative control group was determined using Student's t-test. ##represents P<0.01. The statistical significances between groups treated with DMXAA were determined using Dunnett's multiple comparison test. *, **, represents P<0.05 and 0.01, respectively. Quaque die (QD) represents a once-daily dosing.

EMBODIMENTS FOR CARRYING OUT THE INVENTION

Hereinafter, the present invention will be described in detail. In this specification, the following terms have the following meanings unless indicated otherwise. The following definitions are meant to clarify, but not limit, the terms defined. If a particular term used herein is not specifically defined, terms are used within their accepted meanings to the person skilled in the art.

In the present specification, "$C_{1-6}$ alkyl" is a linear or branched alkyl group having 1 to 6 carbon atoms (hereinafter, abbreviated as $C_{1-6}$), for example methyl, ethyl, n-propyl, isopropyl, n-butyl, isobutyl, sec-butyl, tert-butyl, n-pentyl, n-hexyl or the like. The "$C_{1-6}$ alkyl" is a linear or branched $C_{1-4}$ alkyl in an embodiment; methyl, ethyl, n-propyl, isopropyl or t-butyl in another embodiment; methyl, ethyl, n-propyl, isopropyl in another embodiment; ethyl or n-propyl in another embodiment; methyl or isopropyl in another embodiment; methyl in another embodiment; or t-butyl in still another embodiment.

"$C_{1-6}$ alkylene" is a linear or branched $C_{1-6}$ alkylene, for example, methylene, ethylene, trimethylene, tetramethylene, pentamethylene, hexamethylene, methylmethylene, propylene, 2-methyltrimethylene, ethylethylene, 1,2-dimethylethylene or 1,1,2,2-tetramethylethylene. The "$C_{1-6}$ alkylene" is $C_{1-4}$ alkylene in an embodiment; methylene, ethylene or trimethylene in another embodiment; or methylene in still another embodiment.

"$C_{2-6}$ alkenyl" is a linear or branched $C_{2-6}$ alkenyl, for example, ethenyl, propenyl, butenyl, pentenyl, hexenyl or the like. The "$C_{2-6}$ alkenyl is $C_{2-4}$ alkenyl in an embodiment; ethenyl, propenyl or butenyl in another embodiment; ethenyl in another embodiment; or propenyl in still another embodiment.

"$C_{2-6}$ alkynyl" is a linear or branched $C_{2-6}$ alkynyl, for example, ethynyl, propynyl, butynyl, pentynyl, hexynyl or the like. The "$C_{2-6}$ alkynyl is $C_{2-4}$ alkynyl in an embodiment; ethynyl, propynyl or butynyl in another embodiment; ethynyl in another embodiment; or propynyl in still another embodiment.

"$C_{3-8}$ cycloalkyl" is a $C_{3-8}$ saturated hydrocarbon ring group and may form a bridged bicyclic ring or a spiro ring. The "$C_{3-8}$ cycloalkyl" is, for example, cyclopropyl, cyclobutyl, cyclopentyl, cyclohexyl, cycloheptyl, cyclooctyl, bicyclo[2.2.1]heptyl, bicyclo[3.1.0]hexyl, bicyclo[3.1.1]heptyl or spiro[2.5]octyl. The "$C_{3-8}$ cycloalkyl" is cyclopropyl, cyclobutyl, cyclopentyl, cyclohexyl, cycloheptyl or cyclooctyl in an embodiment; cyclopropyl, cyclobutyl, cyclopentyl or cyclohexyl in another embodiment; cyclopropyl or cyclopentyl in another embodiment; cyclopropyl in yet another embodiment; or cyclopentyl in still another embodiment.

"Halogen" means F, Cl, Br or I. The "halogen" is F or Cl in an embodiment; F in another embodiment; Cl in yet another embodiment; Br is other embodiment; or I is still other embodiment.

"Halogeno $C_{1-6}$ alkyl" is a linear or branched $C_{1-6}$ alkyl group substituted with one or more halogens. The "halogeno $C_{1-6}$ alkyl" is trifluoromethyl, trifluoroethyl, difluoromethyl, difluoroethyl, fluoromethyl, fluoroethyl, chloromethyl, bromomethyl or iodomethyl in an embodiment; trifluoromethyl or difluoromethyl in another embodiment; trifluoromethyl in another embodiment; or difluoromethyl in yet another embodiment.

"Heteroaryl" is a 5- to 6-membered aromatic ring which has one or more heteroatoms, especially oxygen atoms, nitrogen atoms or sulfur atoms, as the constituting atoms of the ring. Examples of the "Heteroaryl" include, but are not limited to, pyrrolyl, furyl, thienyl, pyrazolyl, imidazolyl, isoxazolyl, oxazolyl, isothiazolyl, thiazolyl, triazolyl, oxadiazolyl, thiadiazolyl, tetrazolyl, pyridyl, pyrazinyl, pyrimidinyl, pyridazinyl or triazinyl. The "Heteroaryl" is pyrazolyl or pyridyl in an embodiment; pyridyl in another embodiment.

"Oxo" is a group represented by (=O), and "imino" is a group represented by (=NH).

"6-membered heteroaryl containing one or two nitrogen atoms" means pyridyl, pyrazinyl, pyrimidinyl or pyridazinyl. The "6-membered heteroaryl containing one or two nitrogen atoms" is pyridyl in an embodiment; pyrazinyl in another embodiment; pyrimidinyl in still another embodiment; or pyridazinyl in yet another embodiment.

"6-membered saturated or partially unsaturated heterocyclyl" is a 6-membered hydrocarbon ring, which is saturated or has one double bond in the ring, and which has one or more heteroatoms instead of the carbon atoms, especially oxygen atoms, nitrogen atoms or sulfur atoms, as the constituting atoms of the ring and which may form a bridged bicyclic ring or a spiro ring. Examples of the "6-membered saturated or partially unsaturated heterocyclyl" include, but are not limited to, tetrahydropyran, piperidine, tetrahydrothiopyran, morpholine, piperazine, thiomorpholine, dioxane, dihydropyran, tetrahydropyridine or dihydrothiopyran. The "6-membered saturated or partially unsaturated heterocyclyl" is tetrahydropyran, dihydropyran, piperidine, tetrahydropyridine or morpholine in an embodiment; or tetrahydropyran or dihydropyran in another embodiment.

"4- to 7-membered saturated heterocyclyl" is a 4- to 7-membered saturated hydrocarbon ring which has one or more heteroatoms instead of the carbon atoms, especially oxygen atoms, nitrogen atoms or sulfur atoms, as the constituting atoms of the ring, and which may form a bridged bicyclic ring or a spiro ring. Examples of "4- to 7-membered saturated heterocyclyl" include, but are not limited to, oxetanyl, azetidinyl, thietanyl, tetrahydrofuranyl, pyrrolidinyl, tetrahydrothiophenyl, tetrahydropyranyl, piperidinyl, tetrahydrothiopyranyl, oxepanyl, azepanyl, thiepanyl, dioxolanyl, imidazolidinyl, pyrazolidinyl, dithiolanyl, oxazolidinyl, isoxazolidinyl, thiazolidinyl, isothiazolidinyl, dioxanyl, piperazinyl, dithianyl, morpholinyl, thiomorpholinyl, oxathianyl, dioxepanyl, diazepanyl, dithiepanyl, oxazepanyl, thiazepanyl, oxathiepanyl, 2,6-diazaspiro[3.3]heptyl, 2-oxa-6-azaspiro[3.3]heptyl, 2-azabicyclo[2.2.1]heptyl or 6-azaspiro[2.5]octyl. The "4- to 7-membered saturated heterocyclyl" is oxetanyl, azetidinyl, tetrahydrofuranyl, pyrrolidinyl, tetrahydrothiophenyl, tetrahydropyranyl, piperidinyl, tetrahydrothiopyranyl, morpholinyl, piperazinyl, thiomorpholinyl or 2,6-diazaspiro[3.3]heptyl in an embodiment; azetidinyl, tetrahydrofuranyl, pyrrolidinyl, tetrahydrothiophenyl, tetrahydropyranyl, piperidinyl, morpholinyl, piperazinyl, thiomorpholinyl or 2,6-diazaspiro[3.3]heptyl in another embodiment; azetidinyl, pyrrolidinyl, piperidinyl, morpholinyl, piperazinyl, thiomorpholinyl or 2,6-diazaspiro[3.3]heptyl in another embodiment; tetrahydropyranyl in another embodiment; tetrahydrofuranyl or pyrrolidinyl in another embodiment; tetrahydrothiophenyl in another embodiment; azetidinyl, pyrrolidinyl, piperidinyl or thiomorpholinyl in an embodiment.

The "4- to 7-membered saturated heterocyclyl" in "$R^c$ and $R^d$ may be optionally linked to each other to form 4- to 7-membered saturated heterocyclyl together with the nitrogen atom to which $R^c$ and $R^d$ are attached" is a 4- to 7-membered saturated hydrocarbon ring which has at least one nitrogen atom instead of the carbon atoms among the above described "4- to 7-membered saturated heterocyclyl", for example, azetidinyl, pyrrolidinyl, piperidinyl, morpholinyl, piperazinyl, or thiomorpholinyl. The "4- to 7-membered saturated heterocyclyl" in "$R^c$ and $R^d$ may be optionally linked to each other to form 4- to 7-membered saturated heterocyclyl together with the nitrogen atom to which $R^c$ and $R^d$ are attached" is piperidinyl or morpholinyl in an embodiment.

The "4- to 7-membered saturated heterocyclyl" in "$R^1$ and $R^2$ are linked to each other to form 4- to 7-membered saturated heterocyclyl together with the nitrogen atom to which $R^1$ and $R^2$ are attached, wherein the heterocyclyl may be optionally fused with phenyl" is a 4- to 7-membered saturated hydrocarbon ring which has at least one nitrogen atom instead of the carbon atoms among the above described "4- to 7-membered saturated heterocyclyl", for example, azetidinyl, pyrrolidinyl, piperidinyl, morpholinyl, piperazinyl, thiomorpholinyl or 2,6-diazaspiro[3.3]heptyl. "The heterocyclyl may be optionally fused with phenyl" means that the heterocyclyl is not fused with a phenyl ring or the heterocyclyl is fused with a phenyl ring to form a bicyclic ring, for example, indolinyl, isoindolinyl, tetrahydroquinolinyl or tetrahydroisoquinolinyl. The examples of "$R^1$ and $R^2$ are linked to each other to form 4- to 7-membered saturated heterocyclyl together with the nitrogen atom to which $R^1$ and $R^2$ are attached, wherein the heterocyclyl may be optionally fused with phenyl" are azetidinyl, pyrrolidinyl, piperidinyl or thiomorpholinyl in an embodiment; azetidinyl, pyrrolidinyl, or piperidinyl in another embodiment; pyrrolidinyl in still another embodiment; thiomorpholinyl in another embodiment; or indolinyl in another embodiment.

The "5-membered heterocyclyl" in the "phenyl which may be optionally fused with 5-membered heterocyclyl" is a 5-membered unsaturated hydrocarbon ring which has one or more heteroatoms instead of the carbon atoms, especially oxygen atoms, nitrogen atoms or sulfur atoms, as the constituting atoms of the ring. Examples of the "5-membered heterocyclyl" include, but are not limited to, dihydrofuranyl, furanyl, dihydropyrrolyl, pyrrolyl, dihydrothiophenyl, thiophenyl, dihydrooxazolyl, oxazolyl, dihydroimidazolyl, imidazolyl, dihydrothiazolyl, thiazolyl, dioxolyl or 2-oxodihydropyrrolyl. "Phenyl which may be optionally fused with 5-membered heterocyclyl" is a phenyl or a phenyl fused with the "5-membered heterocyclyl" by sharing its double bond to form a bicyclic ring. Examples of the "phenyl which may be optionally fused with 5-membered heterocyclyl" include, but are not limited to, phenyl, indolyl, benzofuranyl, benzothiophenyl, indazolyl, benzimdazolyl, benzoisoxazolyl, benzoxazolyl, benzoisothiazolyl, benzothiazolyl, 1,3-benzodioxolyl or 1-oxoisoindolynyl. The "phenyl which may be optionally fused with 5-membered heterocyclyl" is phenyl in an embodiment.

"Phenyl which may be optionally fused with phenyl or 6-membered heteroaryl containing one or two nitrogen atoms" is a phenyl or a phenyl fused with another phenyl or 6-membered heteroaryl having one or two nitrogen atoms. Examples of "phenyl which may be optionally fused with phenyl or 6-membered heteroaryl containing one or two nitrogen atoms" include, but are not limited to, naphthyl, quinolyl, quinazolyl or quinoxalyl. The "phenyl which may be optionally fused with phenyl or 6-membered heteroaryl containing one or two nitrogen atoms" is phenyl or quinolyl in an embodiment; phenyl in another embodiment; or quinolyl in still another embodiment.

In the present specification, the expression "optionally substituted" includes "which is not substituted" or "which is substituted with one or more substituents" (for example, substituents which are defined hereinafter.).

Substitution may be occurred wherever a hydrogen atom is normally present on the group.

In one embodiment, "optionally substituted" is "optionally substituted with 1 to 5 substituents", in another embodiment, "optionally substituted with 1 to 3 substituents".

In case of multiple substitutions, substituents can be the same or different from each other.

Examples of substituents of "optionally substituted phenyl", "optionally substituted heteroaryl", "optionally substituted $C_{1-6}$ alkyl", "optionally substituted $C_{3-8}$ cycloalkyl" and "optionally substituted 4- to 7-membered saturated heterocyclyl" include, but are not limited to, the substituents described in $R^3$, $R^4$, $R^5$, $R^6$ or $R^7$.

The "optionally substituted with one or two $R^e$" means unsubstituted or substituted with one or two $R^e$. The "optionally substituted with one or two $R^e$" is substituted with two $R^e$ in an embodiment; substituted with one $R^e$ in another embodiment; or unsubstituted in another embodiment. In case substituted with two $R^e$, the two $R^e$ may be the same or different from each other.

The "substituted with one or two $R^y$", wherein $R^y$ represents $R^3$, $R^4$, $R^5$ or $R^6$, means substituted with one or two $R^y$. The "substituted with one or two $R^y$" is substituted with two $R^y$ in an embodiment; substituted with one $R^y$ in another embodiment. In case substituted with two $R^y$, the two $R^y$ may be the same or different from each other.

The "optionally substituted with one to three $R^7$" means unsubstituted or substituted with one to three $R^7$. The "optionally substituted with one to three $R^7$" is optionally substituted with one or two $R^7$ in an embodiment; substituted with three $R^7$ in another embodiment; substituted with two $R^7$ in another embodiment; substituted with one $R^7$ in still another embodiment; or unsubstituted in yet another embodiment. In case substituted with two or three $R^7$, the two or three $R^7$ may be the same or different from each other.

One or more embodiments can be combined with a different embodiment, even if the combination is not specifically described. That is, all embodiments can be combined in any way.

In the present specification, "treatment" includes both "therapeutic treatment" and "prophylactic treatment". "Therapeutic treatment" means alleviating symptoms, altering the disease course, increasing longevity, etc., and "prophylactic treatment" means reducing the likelihood of contracting the disease in subjects at risk of developing the disease. The "subjects at risk of developing the disease" means individuals with known risk factors that make them more likely to develop the disease than those in the general population.

The "autoimmune disease" herein refers to a disease group including systemic lupus erythematosus, Sjogren's syndrome, rheumatoid arthritis, Crohn's disease, ulcerative colitis, type 1 diabetes, vasculitis, antiphospholipid syndrome, systemic sclerosis, polymyositis, dermatomyositis, mixed connective tissue disease, IgG4-related disease, microscopic polyangiitis, granulomatosis with polyangiitis, eosinophilic granulomatosis with polyangiitis, rapidly progressive glomerulonephritis, Behcet's disease, adult-onset Still's disease, ankylosing spondylitis, autoimmune hepatitis, primary biliary cholangitis, pemphigus, pemphigoid, Hashimoto's disease, Basedow's disease, primary immune thrombocytopenia, autoimmune pulmonary alveolar proteinosis, autoimmune hemolytic anemia, Goodpasture's syndrome, myasthenia gravis, celiac disease and psoriasis, but the "autoimmune disease" is not limited to these diseases. The "autoimmune disease" is systemic lupus erythematosus, Sjogren's syndrome, rheumatoid arthritis, Crohn's disease, ulcerative colitis, type 1 diabetes, vasculitis, systemic sclerosis, dermatomyositis, myasthenia gravis, or psoriasis in an embodiment; systemic lupus erythematosus and Sjogren's syndrome in other embodiment; systemic lupus erythematosus in another embodiment; or Sjogren's syndrome in still another embodiment. The "systemic lupus erythematosus" herein includes several subtypes of lupus erythematosus comprising, but are not limited to, lupus nephritis, neuropsychiatric lupus erythematosus and cutaneous lupus erythematosus. The "systemic lupus erythematosus" is lupus nephritis in an embodiment; neuropsychiatric lupus in another embodiment; or cutaneous lupus erythematosus in still another embodiment. The "systemic lupus erythematosus" is systemic lupus erythematosus which does not have symptoms of lupus nephritis in further embodiment; systemic lupus erythematosus which does not have symptoms of neuropsychiatric lupus in further embodiment; systemic lupus erythematosus which does not have symptoms of lupus nephritis or neuropsychiatric lupus in further embodiment. Further, the "systemic lupus erythematosus" herein includes systemic lupus erythematosus intercurrent with Sjogren's syndrome.

The "neurodegenerative disease" herein refers to a disease group including multiple sclerosis, amyotrophic lateral sclerosis, frontotemporal lobar degeneration, Alzheimer's disease, Parkinson's disease, multiple system atrophy, Lewy body dementia, Huntington's disease, age-dependent macular degeneration, stroke and traumatic brain injury, but the "neurodegenerative disease" is not limited to these diseases. The "neurodegenerative disease" is multiple sclerosis in an embodiment; amyotrophic lateral sclerosis in another embodiment; Parkinson's disease, multiple system atrophy or Lewy body dementia in other embodiment; frontotemporal lobar degeneration in still another embodiment; Huntington's disease in yet another embodiment; stroke in other embodiment; or traumatic brain injury in other embodiment.

The "type I interferonopathy" herein refers to a disease group including Aicardi-Goutieres syndrome (AGS), STING-associated vasculopathy with onset in infancy (SAVI), COPA syndrome, spondyloenchondrodysplasia, ataxia telangiectasia and familial chilblain lupus, but the "type I interferonopathy" is not limited to these diseases. The "type I interferonopathy" is Aicardi-Goutieres syndrome (AGS) or STING-associated vasculopathy with onset in infancy (SAVI) in an embodiment; Aicardi-Goutieres syndrome (AGS) in another embodiment; or STING-associated vasculopathy with onset in infancy (SAVI) in still another embodiment.

The "other STING-mediated disease" herein refers to a disease group including non-alcoholic steatohepatitis (NASH), alcoholic liver disease, acute pancreatitis, acute kidney injury, sepsis, myocardial infarction and chronic heart failure, but the "other STING-mediated disease" is not limited to these diseases. The "other STING-mediated disease" is non-alcoholic steatohepatitis (NASH) or alcoholic liver disease in an embodiment; acute pancreatitis in another embodiment; acute kidney injury in still another embodiment; sepsis in yet another embodiment; or myocardial infarction or chronic heart failure in further embodiment.

Some embodiments including the embodiments described in (1-1) to (14-8) of the compound of formula (I) or a salt thereof in the present invention is shown below, provided that the compound of formula (I) or a salt thereof is not the compound of formula (II), (III), (IV) or (IVa) or a salt thereof.

(II)

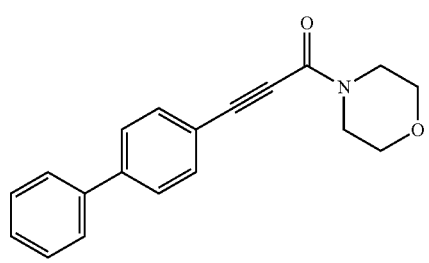

(III)

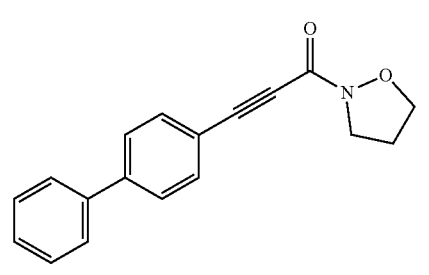

(IV)

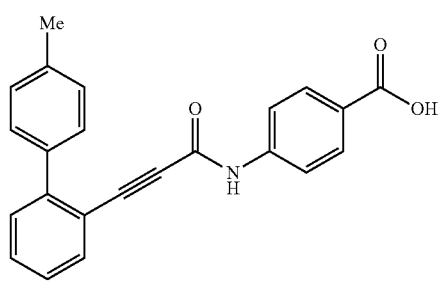

(IVa)

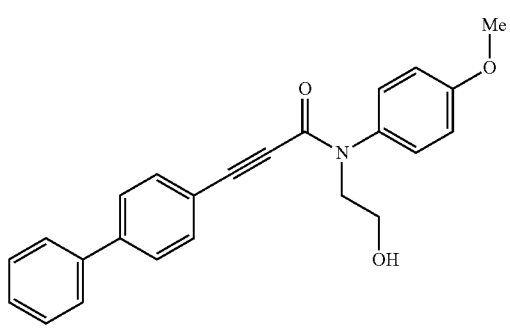

(1-1) A compound or a salt thereof in which Ring A is phenyl which may be optionally fused with 5-membered heterocyclyl, 6-membered heteroaryl containing one or two nitrogen atoms, pyrazolyl or 6-membered saturated or partially unsaturated heterocyclyl.

(1-2) A compound or a salt thereof in which Ring A is phenyl, 6-membered heteroaryl containing one or two nitrogen atoms, pyrazolyl or 6-membered saturated or partially unsaturated heterocyclyl.

(1-3) A compound or a salt thereof in which Ring A is phenyl, pyrazolyl or 6-membered saturated or partially unsaturated heterocyclyl.

(1-4) A compound or a salt thereof in which Ring A is phenyl.

(2-1) A compound or a salt thereof in which Ring B is phenyl which may be optionally fused with phenyl or 6-membered heteroaryl containing one or two nitrogen atoms, 6-membered heteroaryl containing one or two nitrogen atoms, pyrazolyl or imidazolyl.

(2-2) A compound or a salt thereof in which Ring B is phenyl, 6-membered heteroaryl containing one or two nitrogen atoms or pyrazolyl.

(2-3) A compound or a salt thereof in which Ring B is phenyl or 6-membered heteroaryl containing one or two nitrogen atoms.

(2-4) A compound or a salt thereof in which Ring B is the formula (V), wherein X is CH or N.

(V)

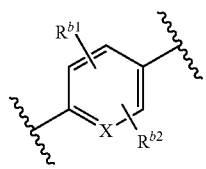

(2-5) A compound or a salt thereof in which Ring B is the formula (V), wherein X is CH.

(2-6) A compound or a salt thereof in which Ring B is the formula (V), wherein X is N.

(2-7) A compound or a salt thereof in which Ring B is the formula (Va).

(Va)

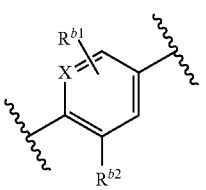

(2-8) A compound or a salt thereof in which Ring B is the formula (Vb).

(Vb)

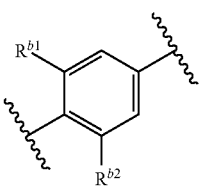

(3-1) A compound or a salt thereof in which $R^{a1}$ and $R^{a2}$ are independently H, $C_{1-6}$ alkyl, —O—$C_{1-6}$ alkyl, —O—$C_{1-6}$ alkylene-$C_{2-6}$ alkenyl, —O—$C_{1-6}$ alkylene-$C_{2-6}$ alkynyl, halogen, halogeno-$C_{1-6}$ alkyl, —O-halogeno-$C_{1-6}$ alkyl or —OH.

(3-2) A compound or a salt thereof in which $R^{a1}$ and $R^{a2}$ are independently H, $C_{1-6}$ alkyl, halogen, halogeno-$C_{1-6}$ alkyl or —O-halogeno-$C_{1-6}$ alkyl.

(3-3) A compound or a salt thereof in which $R^{a1}$ and $R^{a2}$ are independently H, halogen, halogeno-$C_{1-6}$ alkyl or —O-halogeno-$C_{1-6}$ alkyl.

(3-4) A compound or a salt thereof in which $R^{a1}$ and $R^{a2}$ are independently H, halogeno-$C_{1-6}$ alkyl or —O-halogeno-$C_{1-6}$ alkyl.

(3-5) A compound or a salt thereof in which $R^{a1}$ and $R^{a2}$ are independently H or —O-halogeno-$C_{1-6}$ alkyl.

(3-6) A compound or a salt thereof in which $R^{a1}$ is H and $R^{a2}$ is —O-halogeno-$C_{1-6}$ alkyl.

(3-7) A compound or a salt thereof in which $R^{a1}$ and $R^{a2}$ are H.

(4-1) A compound or a salt thereof in which $R^{b1}$ and $R^{b2}$ are independently H, $C_{1-6}$ alkyl, —O—$C_{1-6}$ alkyl, halogeno-$C_{1-6}$ alkyl, —O-halogeno-$C_{1-6}$ alkyl, halogen, —$C_{1-6}$ alkylene-OH, —$C_{1-6}$ alkylene-$NR^cR^d$, —C(=O)—$NR^cR^d$, —$NR^cR^d$, —CN or —OH.

(4-2) A compound or a salt thereof in which $R^{b1}$ and $R^{b2}$ are independently H, halogeno-$C_{1-6}$ alkyl or —$C_{1-6}$ alkylene-$NR^cR^d$.

(4-3) A compound or a salt thereof in which $R^{b1}$ and $R^{b2}$ are independently H or halogeno-$C_{1-6}$ alkyl.

(4-4) A compound or a salt thereof in which $R^{b1}$ is H and $R^{b2}$ is halogeno-$C_{1-6}$ alkyl.

(5) A compound or a salt thereof in which at least one of $R^{a1}$, $R^{a2}$, $R^{b1}$ or $R^{b2}$ are not H.

(6-1) A compound or a salt thereof in which $R^c$ and $R^d$ are independently H, $C_{1-6}$ alkyl, $C_{3-8}$ cycloalkyl, —C(=O)—$C_{1-6}$ alkyl, or —S(=O)$_2$—$C_{1-6}$ alkyl, or, $R^c$ and $R^d$ may be optionally linked to each other to form 4- to 7-membered saturated heterocyclyl together with the nitrogen atom to which $R^c$ and $R^d$ are attached, wherein the heterocyclyl may be optionally substituted with one or two $R^e$.

(6-2) A compound or a salt thereof in which $R^c$ and $R^d$ are independently H or $C_{1-6}$ alkyl, or, $R^c$ and $R^d$ may be optionally linked to each other to form 4- to 7-membered saturated heterocyclyl together with the nitrogen atom to which $R^c$ and $R^d$ are attached, wherein the heterocyclyl may be optionally substituted with one or two $R^e$.

(6-3) A compound or a salt thereof in which $R^c$ and $R^d$ are independently H or $C_{1-6}$ alkyl.

(6-4) A compound or a salt thereof in which $R^c$ and $R^d$ are linked to each other to form 4- to 7-membered saturated heterocyclyl together with the nitrogen atom to which $R^c$ and $R^d$ are attached, wherein the heterocyclyl may be optionally substituted with one or two $R^e$.

(7-1) A compound or a salt thereof in which $R^c$ is $C_{1-6}$ alkyl, —O—$C_{1-6}$ alkyl or halogen.

(7-2) A compound or a salt thereof in which $R^c$ is —O—$C_{1-6}$ alkyl.

(8-1) A compound or a salt thereof in which $R^1$ is H, optionally substituted $C_{1-6}$ alkyl, optionally substituted $C_{3-8}$ cycloalkyl, optionally substituted 4- to 7-membered saturated heterocyclyl, optionally substituted phenyl or optionally substituted heteroaryl, $R^2$ is $C_{1-6}$ alkyl which is substituted with one or two $R^3$, $C_{3-8}$ cycloalkyl which is substituted with one or two $R^4$, 4- to 7-membered saturated heterocyclyl which is substituted with one or two $R^5$, or phenyl which is substituted with one or two $R^6$, or, $R^1$ and $R^2$ are linked to each other to form 4- to 7-membered saturated heterocyclyl together with the nitrogen atom to which $R^1$ and $R^2$ are attached, wherein the heterocyclyl may be optionally fused with phenyl, and the heterocyclyl and/or the fused phenyl may be optionally substituted with one to three $R^7$.

(8-2) A compound or a salt thereof in which $R^1$ is H, $C_{1-6}$ alkyl, $C_{3-8}$ cycloalkyl, 4- to 7-membered saturated heterocyclyl, optionally substituted phenyl or optionally substituted heteroaryl, $R^2$ is $C_{1-6}$ alkyl which is substituted with one or two $R^3$, $C_{3-8}$ cycloalkyl which is substituted with one or two $R^4$, 4- to 7-membered saturated heterocyclyl which is substituted with one or two $R^5$, or phenyl which is substituted with one or two $R^6$, or, $R^1$ and $R^2$ are linked to each other to form 4- to 7-membered saturated heterocyclyl together with the nitrogen atom to which $R^1$ and $R^2$ are attached, wherein the heterocyclyl may be optionally fused with phenyl, and the heterocyclyl and/or the fused phenyl may be optionally substituted with one or two $R^7$.

(8-3) A compound or a salt thereof in which $R^1$ is H, $C_{1-6}$ alkyl, $C_{3-8}$ cycloalkyl, 4- to 7-membered saturated heterocyclyl, phenyl or optionally substituted heteroaryl, $R^2$ is $C_{1-6}$ alkyl which is substituted with one or two $R^3$, $C_{3-8}$ cycloalkyl which is substituted with one or two $R^4$ or 4- to 7-membered saturated heterocyclyl which is substituted with one or two $R^5$, or, $R^1$ and $R^2$ are linked to each other to form 4- to 7-membered saturated heterocyclyl together with the nitrogen atom to which $R^1$ and $R^2$ are attached, wherein the heterocyclyl may be optionally substituted with one or two $R^7$.

(8-4) A compound or a salt thereof in which $R^1$ and $R^2$ are linked to each other to form 4- to 7-membered saturated heterocyclyl together with the nitrogen atom to which $R^1$ and $R^2$ are attached, wherein the heterocyclyl may be optionally substituted with one or two $R^7$.

(8-5) A compound or a salt thereof in which $R^1$ is H, $R^2$ is $C_{1-6}$ alkyl which is substituted by one or two $R^3$, or, $R^1$ and $R^2$ are linked to each other to form azetidinyl, pyrrolidinyl, or piperidinyl or thiomorpholinyl together with the nitrogen atom to which $R^1$ and $R^2$ are attached, wherein the azetidinyl, pyrrolidinyl, piperidinyl or thiomorpholinyl may be optionally substituted with one or two $R^7$.

(8-6) A compound or a salt thereof in which $R^1$ and $R^2$ are linked to each other to form azetidinyl, pyrrolidinyl, piperidinyl or thiomorpholinyl together with the nitrogen atom to which $R^1$ and $R^2$ are attached, wherein the azetidinyl, pyrrolidinyl, piperidinyl or thiomorpholinyl may be optionally substituted with one or two $R^7$.

(8-7) A compound or a salt thereof in which $R^1$ and $R^2$ are linked to each other to form pyrrolidinyl together with the nitrogen atom to which $R^1$ and $R^2$ are attached, wherein the pyrrolidinyl may be optionally substituted with one or two $R^7$.

(8-8) A compound or a salt thereof in which $R^1$ and $R^2$ are linked to each other to form pyrrolidinyl together with the nitrogen atom to which $R^1$ and $R^2$ are attached, wherein the pyrrolidinyl is substituted with two $R^7$.

(8-9) A compound or a salt thereof in which $R^1$ is H, $C_{1-6}$ alkyl, $C_{3-8}$ cycloalkyl, 4- to 7-membered saturated heterocyclyl, optionally substituted phenyl or optionally substituted heteroaryl, $R^2$ is $C_{1-6}$ alkyl which is substituted with one or two $R^3$, $C_{3-8}$ cycloalkyl which is substituted with one or two $R^4$, 4- to 7-membered saturated heterocyclyl which is substituted with one or two $R^5$, or phenyl which is substituted with one or two $R^6$, or, $R^1$ and $R^2$ are linked to each other to form 4- to 7-membered saturated heterocyclyl together with the nitrogen atom to which $R^1$ and $R^2$ are attached, wherein the heterocyclyl may be optionally fused with phenyl, and the heterocyclyl may be optionally substituted with one or two $R^7$.

(9-1) A compound or a salt thereof in which each $R^3$ is independently —OH, —O—$C_{1-6}$ alkyl, —C(=O)—$NH_2$, —C(=O)—NH—$C_{1-6}$ alkyl, —C(=O)—N($C_{1-6}$ alkyl)$_2$, —$NH_2$, —NH—$C_{1-6}$ alkyl, —N($C_{1-6}$ alkyl)$_2$, —NH—C (=O)—C$_{1-6}$ alkyl, —NH—S(=O)$_2$—C$_{1-6}$ alkyl, —NH—S(=O)$_2$—C$_{1-6}$ alkylene-OH, —NH—S(=O)$_2$—C$_{1-6}$ alkylene-C(=O)—OH, —S(=O)$_2$—NH$_2$, —S(=O)$_2$—C$_{1-6}$ alkyl or —S(=O)(=NH)—C$_{1-6}$ alkyl.

(9-2) A compound or a salt thereof in which each R$^3$ is independently —OH, —C(=O)—NH$_2$, —NH—C(=O)—C$_{1-6}$ alkyl, —NH—S(=O)$_2$—C$_{1-6}$ alkyl or —S(=O)$_2$—NH$_2$.

(9-3) A compound or a salt thereof in which each R$^3$ is independently —OH or —C(=O)—NH$_2$.

(10-1) A compound or a salt thereof in which each R$^4$ is independently —OH, —O—C$_{1-6}$ alkyl, —C(=O)—NH$_2$, —C(=O)—NH—C$_{1-6}$ alkyl, —C(=O)—N(C$_{1-6}$ alkyl)$_2$, —NH$_2$, —NH—C$_{1-6}$ alkyl, —N(C$_{1-6}$ alkyl)$_2$, —NH—C(=O)—C$_{1-6}$ alkyl, —NH—S(=O)$_2$—C$_{1-6}$ alkyl, —S(=O)$_2$—NH$_2$, —S(=O)$_2$—C$_{1-6}$ alkyl or —S(=O)(=NH)—C$_{1-6}$ alkyl.

(10-2) A compound or a salt thereof in which each R$^4$ is independently —OH, —C(=O)—NH$_2$, —NH—C(=O)—C$_{1-6}$ alkyl, —NH—S(=O)$_2$—C$_{1-6}$ alkyl or —S(=O)$_2$—NH$_2$.

(10-3) A compound or a salt thereof in which R$^4$ is —OH.

(11-1) A compound or a salt thereof in which each R$^5$ is independently —OH, oxo or imino.

(11-2) A compound or a salt thereof in which each R$^5$ is independently —OH or oxo.

(11-3) A compound or a salt thereof in which R$^5$ is —OH.

(11-4) A compound or a salt thereof in which R$^5$ is oxo.

(11-5) A compound or a salt thereof in which each R$^5$ is independently oxo or imino.

(12-1) A compound or a salt thereof in which each R$^6$ is independently —C(=O)—OH, —S(=O)$_2$—NH$_2$, —S(=O)$_2$—C$_{1-6}$ alkyl, —S(=O)(=NH)—C$_{1-6}$ alkyl or —NH—S(=O)$_2$—C$_{1-6}$ alkyl.

(12-2) A compound or a salt thereof in which each R$^6$ is independently —C(=O)—OH or —S(=O)$_2$—NH$_2$.

(12-3) A compound or a salt thereof in which R$^6$ is —C(=O)—OH.

(12-4) A compound or a salt thereof in which each R$^6$ is —S(=O)$_2$—NH$_2$.

(13-1) A compound or a salt thereof in which each R$^7$ is independently C$_{1-6}$ alkyl, —C$_{1-6}$ alkylene-OH, —C$_{1-6}$ alkylene-C(=O)—OH, C$_{3-8}$ cycloalkyl, —OH, —O—C$_{1-6}$ alkyl, —NH$_2$, —NH—C$_{1-6}$ alkyl, —N(C$_{1-6}$ alkyl)$_2$, —NH—C(=O)—C$_{1-6}$ alkyl, —NH—S(=O)$_2$—C$_{1-6}$ alkyl, —S(=O)$_2$—C$_{1-6}$ alkyl, —S(=O)(=NH)—C$_{1-6}$ alkyl, —C(=O)—OH, —C(=O)—NH$_2$, —C(=O)—NH—C$_{1-6}$ alkyl, —C(=O)—N(C$_{1-6}$ alkyl)$_2$, oxo, imino or 4- to 7-membered saturated heterocyclyl which may be optionally substituted with one or two oxo.

(13-2) A compound or a salt thereof in which each R$^7$ is independently C$_{1-6}$ alkyl, —C$_{1-6}$ alkylene-OH, —C$_{1-6}$ alkylene-C(=O)—OH, C$_{3-8}$ cycloalkyl, —OH, —NH$_2$, —C(=O)—OH, —C(=O)—NH$_2$, oxo, imino or 4- to 7-membered saturated heterocyclyl which may be optionally substituted with one or two oxo.

(13-3) A compound or a salt thereof in which each R$^7$ is independently —C$_{1-6}$ alkylene-OH, —OH, —C(=O)—NH$_2$, oxo or imino.

(13-4) A compound or a salt thereof in which each R$^7$ is independently —C$_{1-6}$ alkylene-OH, —OH or —C(=O)—NH$_2$.

(13-5) A compound or a salt thereof in which R$^7$ is —OH.

(14) A compound or a salt thereof which is a combination of two or more embodiments that are not mutually contradictory, among the embodiments of the groups described in (1-1) to (13-5). Examples thereof include, but are not limited to, the following combinations.

(14-1) A compound or a salt thereof which is a combination of (1-1), (2-1), (3-1), (4-1), (6-1), (7-1), (8-1), (9-1), (10-1), (11-1), (12-1) and (13-1).

(14-2) A compound or a salt thereof which is a combination of (1-1), (2-2), (3-2), (4-2), (6-2), (7-1), (8-2), (9-2), (10-2), (11-2), (12-2) and (13-2).

(14-3) A compound or a salt thereof which is a combination of (1-2), (2-4), (3-2), (4-2), (5), (6-2), (7-1), (8-3), (9-2), (10-3), (11-2) and (13-2).

(14-4) A compound or a salt thereof which is a combination of (1-2), (2-4), (3-2), (4-4), (8-4) and (13-2).

(14-5) A compound or a salt thereof which is a combination of (1-4), (2-4), (3-7), (4-4), (8-5), (9-3) and (13-3).

(14-6) A compound or a salt thereof which is a combination of (1-4), (2-4), (3-7), (4-4), (8-6) and (13-3).

(14-7) A compound or a salt thereof which is a combination of (1-4), (2-5), (3-7), (4-4), (8-8) and (13-5).

(14-8) A compound or a salt thereof which is a combination of (1-1), (2-2), (3-2), (4-2), (6-2), (7-1), (8-9), (9-2), (10-2), (11-2), (12-2) and (13-2).

Examples of the specific compounds included in the present invention include the following compounds or salts thereof:

N$^2$-{3-[2-(trifluoromethyl)[1,1'-biphenyl]-4-yl]prop-2-ynoyl}-L-serinamide,

1-[(3R,4R)-3,4-dihydroxypyrrolidin-1-yl]-3-[2-(trifluoromethyl)[1,1'-biphenyl]-4-yl]prop-2-yn-1-one, 1-{3-[2-(trifluoromethyl)[1,1'-biphenyl]-4-yl]prop-2-ynoyl}piperidine-4-carboxamide, 1-[(3R,4S)-3,4-dihydroxypyrrolidin-1-yl]-3-[2-(trifluoromethyl)[1,1'-biphenyl]-4-yl]prop-2-yn-1-one, 1-[3,3-bis(hydroxymethyl)azetidin-1-yl]-3-[2-(trifluoromethyl)[1,1'-biphenyl]-4-yl]prop-2-yn-1-one, N-[(2R)-2,3-dihydroxypropyl]-3-[2-(trifluoromethyl)[1,1'-biphenyl]-4-yl]prop-2-ynamide, N-[(2S)-2,3-dihydroxypropyl]-3-[2-(trifluoromethyl)[1,1'-biphenyl]-4-yl]prop-2-ynamide, 1-[(3S,4S)-3,4-dihydroxypyrrolidin-1-yl]-3-[2-(trifluoromethyl)[1,1'-biphenyl]-4-yl]prop-2-yn-1-one, (3R)-1-{3-[2-(trifluoromethyl)[1,1'-biphenyl]-4-yl]prop-2-ynoyl}pyrrolidine-3-carboxamide, 1-[(3R,4S)-3,4-dihydroxypyrrolidin-1-yl]-3-[6-phenyl-5-(trifluoromethyl)pyridin-3-yl]prop-2-yn-1-one, and 1-imino-4-{3-[2-(trifluoromethyl)[1,1'-biphenyl]-4-yl]prop-2-ynoyl}-1λ$^6$-thiomorpholin-1-one.

Examples of the specific compounds included in the present invention also include the compounds listed in Tables 13-20 either in free base form or salts thereof.

With regard to the compound of formula (I), tautomers or geometrical isomers thereof may exist, depending on the kinds of the substituents. In the present specification, the compound of formula (I) and salts thereof may be described in only one form of isomers in some cases, but the present invention includes other isomers, isolated forms of the isomers, or a mixture thereof.

Furthermore, some of the compounds of formula (I) may have asymmetric carbon atoms or axial chirality in some cases, and correspondingly, enantiomers (optical isomers) thereof can exist. The present invention includes isolated form of individual enantiomer of the compound of formula (I) or a mixture thereof, including racemic mixture or otherwise.

In one embodiment, an enantiomer is "stereochemically pure". "Stereochemically pure" refers to a level of stereochemical purity that would be recognized as essentially "pure" by those of skill in the art. In another embodiments, an enantiomer is a compound having stereochemical purity of more than 90% e.e (enantiomeric excess), more than 95% e.e, more than 98% e.e., more than 99% e.e, or more than 99.5% e.e.

Moreover, the salt of the compound of formula (I) is a pharmaceutically acceptable salt of the compound of formula (I), and the compounds of formula (I) may form an acid addition salt or a salt with a base, depending on the kinds of the substituents in some cases. Specifically, examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propanoic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, and glutamic acid, and salts with metal anions such as sodium, potassium, magnesium, calcium, and aluminum, and with organic bases such as methylamine, ethylamine, ethanolamine, lysine, and ornithine, salts with various amino acids such as acetyl leucine, or derivatives of amino acids, ammonium salts, and others.

In addition, the present invention also includes various hydrates or solvates, and crystal polymorph substances of the compound of formula (I) and a salt thereof.

The present invention includes all pharmaceutically acceptable, isotopically-labelled compounds of the invention with one or more radioactive or non-radioactive isotopes.

Examples of isotopes suitable for isotopically-labeling compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of the invention, for example, those incorporating a radioactive isotope, can be useful in drug and/or substrate tissue distribution studies. The radioactive isotopes tritium, i.e., $^3$H, and carbon-14, i.e., $^{14}$C, can be used for this purpose in view of their ease of incorporation and ready means of detection.

Substitution with heavier isotopes, for example substitution hydrogen with deuterium, i.e., 2H, may afford certain therapeutic advantages resulting from greater metabolic stability, for example, increased in vivo half-life or reduced dosage requirements, reduced drug-drug interference, and hence can be used in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

(Production Process)

The compound of formula (I) or a salt thereof can be prepared by applying various known synthetic methods, using the characteristics based on their basic structures or the kinds of the substituents. At this time, depending on the types of the functional groups, it is in some cases effective from the viewpoint of the preparation techniques to protect the functional group with an appropriate protective group (a group which is capable of being easily converted into the functional group), during the steps from starting materials to intermediates. Examples of the protective group include the protective groups as described in "Greene's Protective Groups in Organic Synthesis (4th edition, 2006)", edited by P. G. M. Wuts and T. W. Greene, and the like, which may be appropriately selected and used depending on the reaction conditions. In these methods, a desired compound can be obtained by introducing the protective group to carry out the reaction, and then, if desired, removing the protective group.

The pharmaceutically acceptable prodrug refers to a compound having a group which can be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. In addition, the prodrug of the compound of the formula (I) can be prepared by introducing a specific group during the steps from starting materials to intermediates, in the same manner as for the above protective groups, or by further carrying out the reaction using the obtained compound of the formula (I). The reaction can be carried out by applying a method known to a person skilled in the art, such as common esterification, amidation, and dehydration.

Hereinbelow, typical preparation methods of the compound of formula (I) will be described. Each of the production processes can also be carried out with reference to the documents appended to the description herein. Further, the preparation methods of the present invention are not limited to the examples as shown below.

The following abbreviations may be used herein.

AcOH: acetic acid, BOC: t-butoxycarbonyl, CHCl$_3$: chloroform, CH$_2$Cl$_2$: dichloromethane, CH$_3$CN: acetonitrile, COMU: (1-cyano-2-ethoxy-2-oxoethylidenaminooxy)dimethylamino-morpholino-carbenium hexafluorophosphate, (COCl)$_2$: oxalyl chloride, CuI: copper (I) iodide, Cu(OAc)$_2$: copper (II) acetate, DBU: 1,8-diazabicyclo[5.4.0]undec-7-ene, DIBAL-H: diisobutylalminium hydride, DMF: N,N-dimethylformamide, DMSO: dimethylsulfoxide, DIPEA: N,N-diisopropylethylamine, Et$_3$N: triethylamine, EtOH: ethanol, Et$_2$O: diethyl ether, EtOAc: ethyl acetate, HATU: 1-[bis(dimethylamino)methylene]-1H-1,2,3-triazolo[4,5-b]pyridinium 3-oxide hexafluorophosphate, (HCHO)n: paraformaldehyde, HCl: hydrochloric acid, HOBt: 1-hydroxybenzotriazole, IPA: isopropyl alcohol, IPE: diisopropyl ether, K$_2$CO$_3$: potassium carbonate, K$_3$PO$_4$: potassium phosphate, LiBH$_4$: lithium borohydride, LiCl: lithium chloride, LiOH·H$_2$O: lithium hydroxide monohydrate, Me: methyl, MeOH: methanol, MgSO$_4$: magnesium sulfate, MnO$_2$: manganese (IV) oxide, NaBH$_4$: sodium borohydride, NaBH$_3$CN: sodium cyanoborohydride, Na$_2$CO$_3$: sodium carbonate, NaHCO$_3$: sodium bicarbonate, NaNO$_2$: sodium nitrite, NaOH: sodium hydroxide, nBuLi: n-butyllithium, m-CPBA: m-chloroperoxybenzoic acid, NH$_4$HCO$_3$: ammonium bicarbonate, NIS: N-iodosuccinimide, NMP: 1-methylpyrrolidine-2-one, P(t-Bu)$_3$·HBF$_4$: tri-t-butylphosphonium tetrafluoroborate, Pd/C: palladium on carbon, PdCl$_2$(PPh$_3$)$_2$: bis(triphenylphosphine)palladium (II) dichloride, PdCl$_2$ (dppf)/CH$_2$Cl$_2$: [1,1'-bis(diphenylphosphino)ferrocene]palladium (II) dichloride/dichloromethane adduct, Pd$_2$(dba)$_3$: (1E,4E)-1,5-diphenylpenta-1,4-dien-3-one/palladium (3:2), Pd(OAc)$_2$: palladium (II) acetate, Pd(PPh$_3$)$_4$: tetrakis (triphenylphosphine)palladium, PyBOP: (benzotriazole-1-yloxy)tripyrrolidinophosphonium hexafluorophosphate, SPhos: 2-dicyclohexylphosphino-2',6'-dimethoxybiphenyl, TBAF: tetra-n-butylammonium fluoride, TBS: tert-butyldi(methyl)silyl, tBu: tert-butyl, Tf: trifluoromethanesulfonyl, THF: tetrahydrofuran, TFA: trifluoroacetic acid, TMS: trimethylsilyl, T3P (registered trademark): 2,4,6-Tripropyl-1,3,5,2,4,6-trioxatriphosphorinane-2,4,6-trioxide, EDC: 1-ethyl-3-(3-dimethylaminopropyl)carbodiimide, EDC·HCl: 1-ethyl-3-(3-dimethylaminopropyl)carbodiimide hydrochloride, XPhos: 2-dicyclohexylphosphino-2',4',6'-triisopropylbiphenyl (Production Process 1)

[Chem 17]

to 190° C., in the presence of a catalyst, a co-catalyst and a base in a solvent inactive to the reaction or without solvent, typically for 0.1 hours to 5 days. Examples of the catalyst used here include, but are not limited to $Pd(PPh_3)_4$, $PdCl_2(PPh_3)_2$, $PdCl_2(dppf)/CH_2Cl_2$, $Pd_2(dba)_3$, $Pd(OAc)_2$ and a combination thereof. Examples of the co-catalyst used here include, but are not limited to, CuI. Examples of the base include, but are not limited to, DBU, $Et_3N$ and DIPEA. Examples of the solvent include, but are not limited to, ethers such as THF, 2-methyltetrahydrofuran, 1,4-dioxane and 1,2-dimethoxyethane, $CH_3CN$, NMP, DMF, DMSO and mixtures thereof. It may be advantageous in some cases, for the smooth progress of the reaction, to carry out the reaction

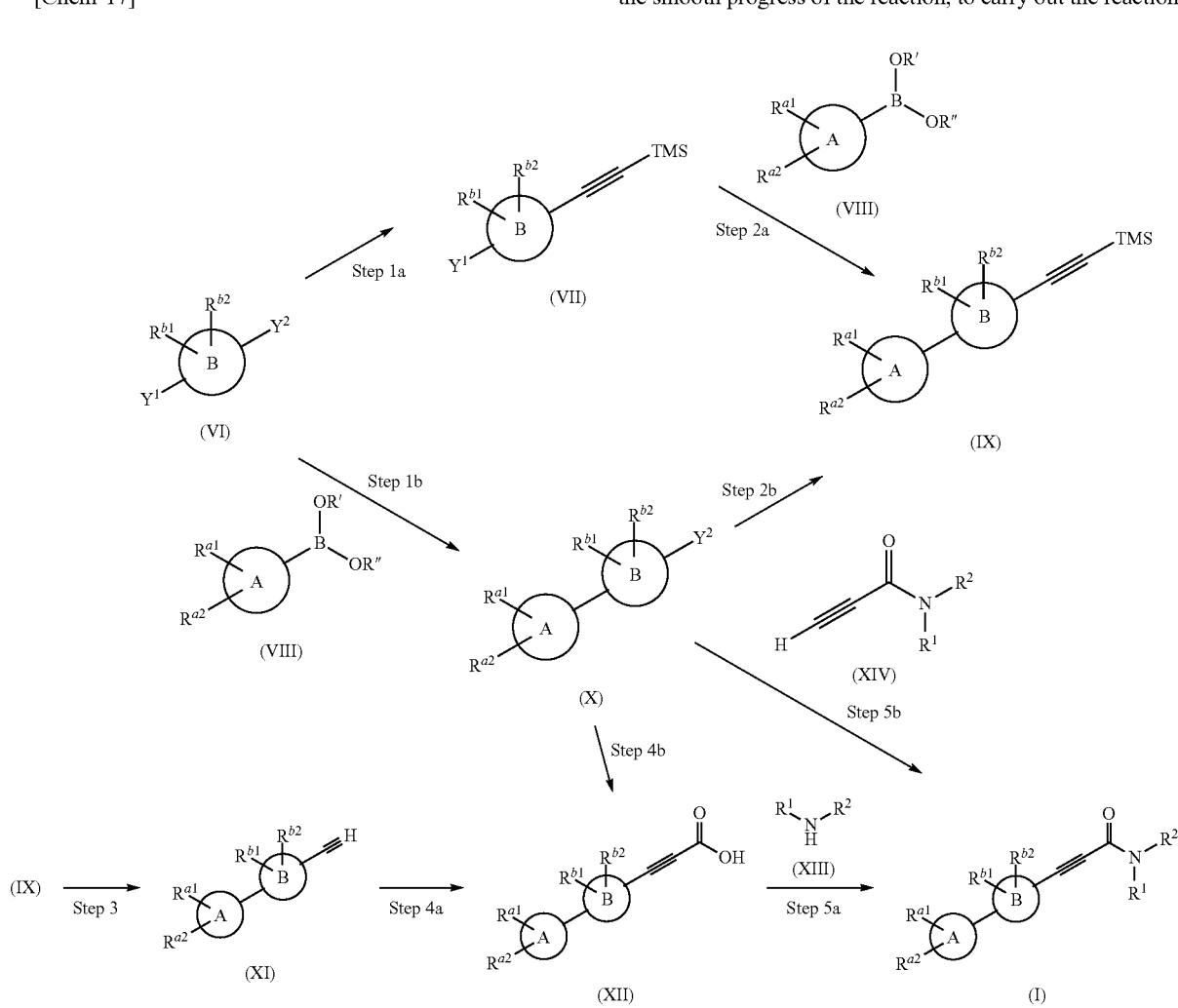

(in which, $Y^1$ and $Y^2$ are independently Cl, Br, I or OTf. Both R' and R" are H, or R' and R" are linked to each other to form 4,4,5,5-tetramethyl-1,3,2-dioxaborane together with the boronic acid residue to which R and R are attached. The same applies hereinafter).

(Step 1a)

This step is a step of preparing a compound of formula (VII) by reaction of a compound of formula (VI) and trimethylsilylacetylene. In this reaction, the compound of formula (VI) and trimethylsilylacetylene are used in equivalent amount, or one of the compounds is used in excessive amount. A mixture of these compounds is stirred under cooling or heating to reflux, preferably at room temperature in the presence of sodium iodide. This reaction may be carried out under microwave irradiation.

REFERENCE

Tetrahedron Letters, 50, pp 4467-4470 (1975)

(Step 2a)

This step is a step of preparing a compound of formula (IX) by reaction of a compound of formula (VII) and (VIII). In this reaction, the compound of formula (VII) and the compound of formula (VIII) are used in equivalent amount, or one of the compounds is used in excessive amount. A mixture of these compounds is stirred under cooling or heating to reflux, preferably at room temperature to 190° C., in the presence of a catalyst and a base in a solvent inactive to the reaction or without solvent, typically for 0.1 hours to 5 days. Examples of the catalyst used here include, but are not limited to, Pd(PPh$_3$)$_4$, PdCl$_2$(PPh$_3$)$_2$, PdCl$_2$(dppf)/CH$_2$Cl$_2$, Pd$_2$(dba)$_3$ and Pd(OAc)$_2$. Examples of the base include, but are not limited to, K$_3$PO$_4$, Na$_2$CO$_3$, K$_2$CO$_3$, cesium carbonate (Cs$_2$CO$_3$), NaOH and sodium t-butoxide. Examples of the solvent include, but are not limited to, ethers such as diethyl ether, THF, 1,4-dioxane and 1,2-dimethoxyethane, aromatic hydrocarbons such as benzene, toluene and xylene, and water, pyridine, CH$_3$CN, NMP, DMF, DMSO and mixtures thereof. It may be advantageous in some cases, for the smooth progress of the reaction, to carry out the reaction in the presence of a phosphine ligand such as SPhos, XPhos, dicyclohexyl(2',6'-diisopropoxy-[1, 1'-biphenyl]-2-yl)phosphine (RuPhos), 4,5-bis(diphenylphosphino)-9,9-dimethylxanthene (XantPhos), P(t-Bu)$_3$·HBF$_4$ and the like. This reaction may be carried out under microwave irradiation.

REFERENCE

Journal of the American Chemical Society, 127, pp 4685-4696 (2005)

The compound of the formula (IX) is also obtained from the compound of the formula (VI) via Step 1b and Step 2b.

(Step 1b)

This step is a step of preparing a compound of formula (X) by reaction of a compound of formula (VI) and (VIII). This reaction is carried out in the same condition as the Step 2a, by using the compound of the formula (VI) instead of the compound of the formula (VII).

(Step 2b)

This step is a step of preparing a compound of formula (IX) by reaction of a compound of formula (X) and trimethylsilylacetylene. This reaction is carried out in the same condition as the Step 1a, by using the compound of the formula (X) instead of the compound of the formula (VI).

(Step 3)

This step is a step of preparing a compound of formula (XI) by deprotecting a compound of formula (IX). This reaction is carried out by using the compound of the formula (IX) and a deprotecting reagent by stirring the mixture in a solvent which is inactive to the reaction, under cooling or heating to reflux, preferably at room temperature to 100° C., typically for 0.1 hours to 5 days. Examples of the deprotecting reagent include, but are not limited to, bases such as potassium carbonate and the like, and fluorides such as tetrabutylammonium fluoride and the like. Examples of the solvent include, but are not limited to, alcohols such as MeOH and EtOH, and ethers such as THF or 1,4-dioxane.

(Step 4a)

This step is a step of preparing a compound of formula (XII) by reaction of a compound of formula (XI) and carbon dioxide. This reaction is carried out to obtain a lithium acetylide intermediate at first, by using the compound of the formula (XI) and an organolithium reagent in a solvent which is inactive to the reaction, under cooling or at room temperature. Then the lithium acetylide intermediate is added to an excessive amount of dry ice under cooling or at room temperature to obtain the compound of the formula (XII). The entire reactions are typically carried out for 0.1 hours to 1 day. Examples of the organolithium reagent include, but are not limited to, n-butyllithium, t-butyllithium and lithium diisopropylamide. Examples of the solvent include, but are not limited to, hydrocarbons such as n-hexane or n-pentane, and ethers such as THF or 1,4-dioxane.

(Step 4b)

The compound of the formula (XII) is also obtained from the compound of the formula (X) via Step 4b. This step is a step of preparing a compound of formula (XII) by reaction of a compound of formula (X) and propiolic acid. This reaction is carried out in the same condition as the Step 1a, by using propiolic acid instead of trimethylsilylacetylene.

(Step 5a)

This step is a step of preparing a compound of formula (I) by reaction of a compound of formula (XII) and (XIII). In this reaction, the compound of formula (XII) and the compound of formula (XIII) are used in equivalent amount, or one of the compounds is used in excessive amount. A mixture of these compounds is stirred under cooling or heating to reflux, preferably at room temperature to 100° C., in the presence of a condensation agent and a base in a solvent inactive to the reaction or without solvent, typically for 0.1 hours to 5 days. Examples of the condensation agent include, but are not limited to, T3P (registered trademark), HATU, EDC, EDC·HCl, COMU, 2-chloro-1-methylpyridinium iodide and the like. Examples of the base include, but are not limited to, Et$_3$N and DIPEA. Examples of the solvent include, but are not limited to, ethers such as THF, 2-methyltetrahydrofuran, 1,4-dioxane and 1,2-dimethoxyethane, halocarbons such as CH$_2$Cl$_2$ and CHCl$_3$, acetonitrile, NMP, DMF, DMSO and mixtures thereof. It may be advantageous in some cases, for the smooth progress of the reaction, to carry out the reaction in the presence of HOBt.

This step can also be conducted by using a chlorinating agent as the condensation agent. This reaction is carried out to obtain an acyl chloride intermediate at first, by using the compound of formula (XII) and the chlorinating agent in a solvent which is inactive to the reaction or without solvent, under cooling or heating to reflux, preferably at 0° C. to room temperature. Then the acyl chloride intermediate is added to a mixture of a base and the compound of formula (XIII) in a solvent which is inactive to the reaction, under cooling or heating to reflux, preferably at 0° C. to room temperature. The entire reactions are typically carried out for 0.1 hours to 1 day. Examples of the chlorinating agent include, but are not limited to, (COCl)$_2$, phosphoryl chloride (POCl$_3$), and thionyl chloride (SOCl$_2$). Examples of the base include, but are not limited to, Na$_2$CO$_3$, NaHCO$_3$, K$_2$CO$_3$, Et$_3$N, DIPEA and pyridine. Examples of the solvent include, but are not limited to, haloalkanes such as CH$_2$Cl$_2$ or CHCl$_3$, and ethers such as THF or 1,4-dioxane. Water can be added as a co-solvent.

(Step 5b)

The compound of the formula (I) is also obtained from the compound of the formula (X) via Step 5b. This step is a step of preparing a compound of formula (I) by reaction of a compound of formula (X) and a compound of formula (XIV). This reaction is carried out in the same condition as the Step 1a, by using the compound of the formula (XIV) instead of trimethylsilylacetylene.

(Production Process 2)
[Chem 18]

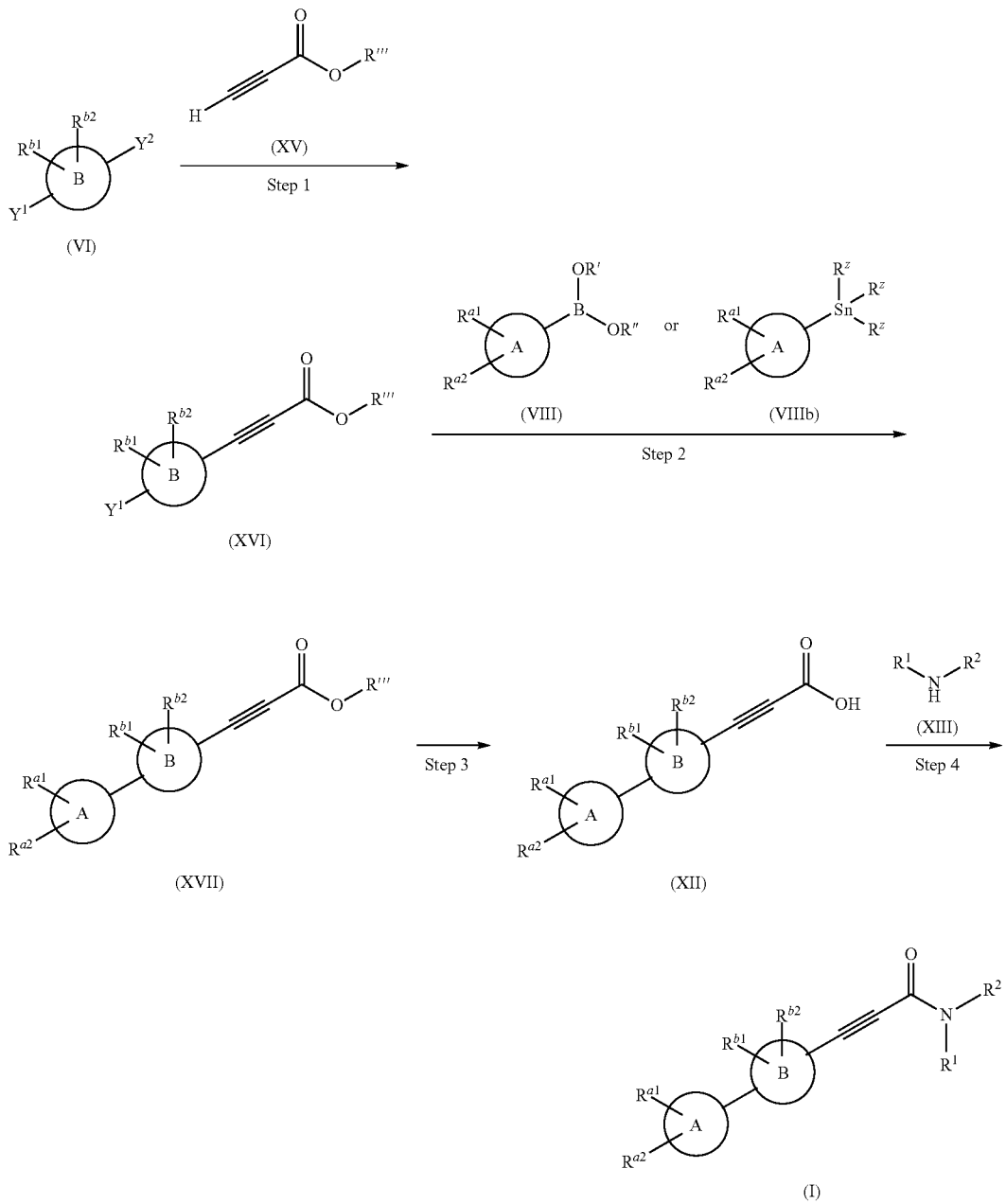

(in which, R''' and $R^z$ are $C_{1-6}$ alkyl. The same applies hereinafter).

(Step 1)

This step is a step of preparing a compound of formula (XVI) by reaction of a compound of formula (VI) and a compound of formula (XV). This reaction is carried out in the same condition as the Step 1a of the Production Process 1, by using the compound of the formula (XV) instead of trimethylsilylacetylene.

(Step 2)

This step is a step of preparing a compound of formula (XVII) by reaction of a compound of formula (XVI) and a compound of formula (VIII). This reaction is carried out in the same condition as the Step 2a of the Production Process 1, by using the compound of the formula (XVI) instead of the compound of the formula (VII).

Or, in this step, the compound of the formula (XVII) can also be obtained by using a stannyl compound of formula (VIIIb) instead of the corresponding boronate compound of the formula (VIII).

(Step 3)

This step is a step of preparing a compound of formula (XII) by hydrolyzing an ester group of a compound of formula (XVII). This reaction is carried out by using the compound of the formula (XVII) and an aqueous solution of a base by stirring the mixture in a solvent which is inactive to the reaction, under cooling or heating to reflux, preferably at room temperature to 100° C., typically for 0.1 hours to 5 days. Examples of the base include, but are not limited to, LiOH·H$_2$O, NaOH, KOH, K$_2$CO$_3$ and the like. Examples of the solvent include, but are not limited to, alcohols such as MeOH or EtOH, ethers such as THF or 1,4-dioxane and a mixture thereof.

(Step 4)

This step is a step of preparing a compound of formula (I) by reaction of a compound of formula (XII) and a compound of formula (XIII). This reaction is carried out in the same condition as the Step 5a of the Production Process 1.

(Production Process 3)

(Step 3)

This step is a step of preparing a compound of formula (I) by reaction of a compound of formula (XIX) and a compound of formula (VIII). This reaction is carried out in the same condition as the Step 2a of the Production Process 1, by using the compound of the formula (XIX) instead of the compound of the formula (VII).

Or, in this step, the compound of the formula (I) can also be obtained by using a stannyl compound of formula (VIIIb) instead of the corresponding boronate compound of the formula (VIII).

[Chem 19]

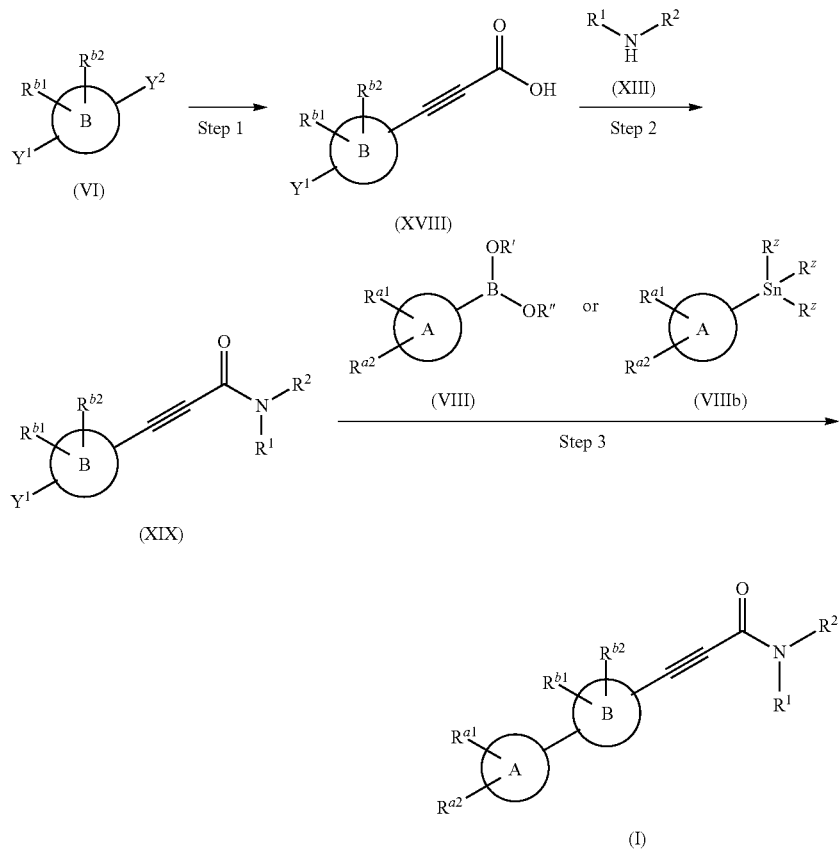

(Step 1)

This step is a step of preparing a compound of formula (XVIII) by reaction of a compound of formula (VI) and propiolic acid. This reaction is carried out in the same condition as the Step 1a of the Production Process 1, by using propiolic acid instead of trimethylsilylacetylene.

(Step 2)

This step is a step of preparing a compound of formula (XIX) by reaction of a compound of formula (XVIII) and a compound of formula (XIII). This reaction is carried out in the same condition as the Step 5a of the Production Process 1, by using the compound of the formula (XVIII) instead of the compound of the formula (XII).

(Starting Compound Synthetic Process 1)

[Chem 20]

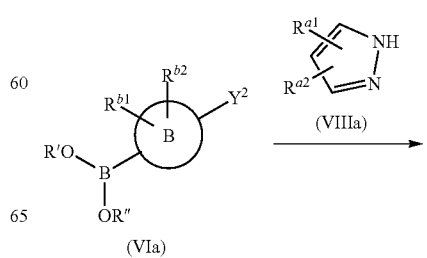

-continued

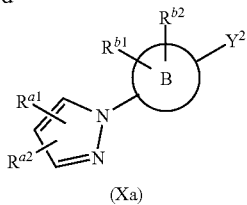

(Xa)

This Process is a process of preparing a compound of formula (Xa) which has pyrazol-1-yl group as the Ring A among the compound of formula (X), by a reaction of a compound of formula (VIa) and a compound of formula (VIIIa). In this reaction, the compound of formula (VIa) and the compound of formula (VIIIa) are used in equivalent amount, or one of the compounds is used in excessive amount. A mixture of these compounds is stirred under cooling or heating to reflux, preferably at room temperature to 190° C., in the presence of a catalyst and a base in a solvent inactive to the reaction or without solvent, typically for 0.1 hours to 5 days. Examples of the catalyst used here include, but are not limited to, $Cu(OAc)_2$, copper (I) oxide ($Cu_2O$), copper (I) chloride (CuCl), copper (II) bromide ($CuBr_2$), CuI and the like. Examples of the base used here include, but are not limited to, $Et_3N$, DIPEA, pyridine and the like. Examples of the solvent include, but are not limited to, $CH_2Cl_2$, $CH_3CN$, DMF, DMSO, MeOH, EtOH, toluene and the like. It may be advantageous in some cases, for the smooth progress of the reaction, to carry out the reaction in the presence of a bidentate ligand such as 1,10-phenanthroline or N,N,N',N'-tetramethylethylenediamine, and/or molecular sieve.

(Starting Compound Synthetic Process 2)

[Chem 21]

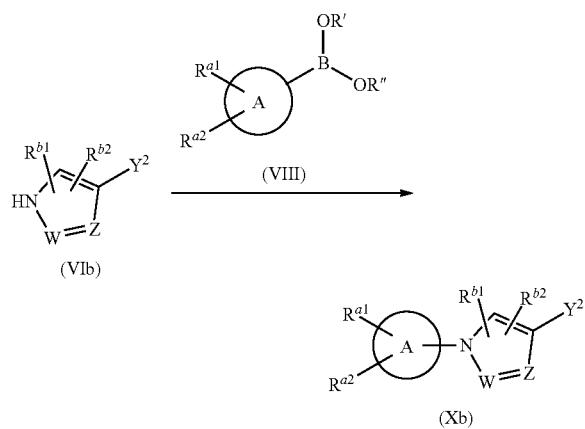

(in which, one of W or Z is N and the other is CH. The same applies hereinafter).

This Process is a process of preparing a compound of formula (Xb) which has pyrazol-1-yl group or imidazole-1-yl group as the Ring B among the compound of formula (X), by a reaction of a compound of formula (VIb) and a compound of formula (VIII). This reaction is carried out in the same conditions as the Starting Compound Synthetic Process 1, by using the compound of formula (VIb) and the compound of formula (VIII) instead of the compound of formula (VIa) and the compound of formula (VIIIa).

(Starting Compound Synthetic Process 3)

[Chem 22]

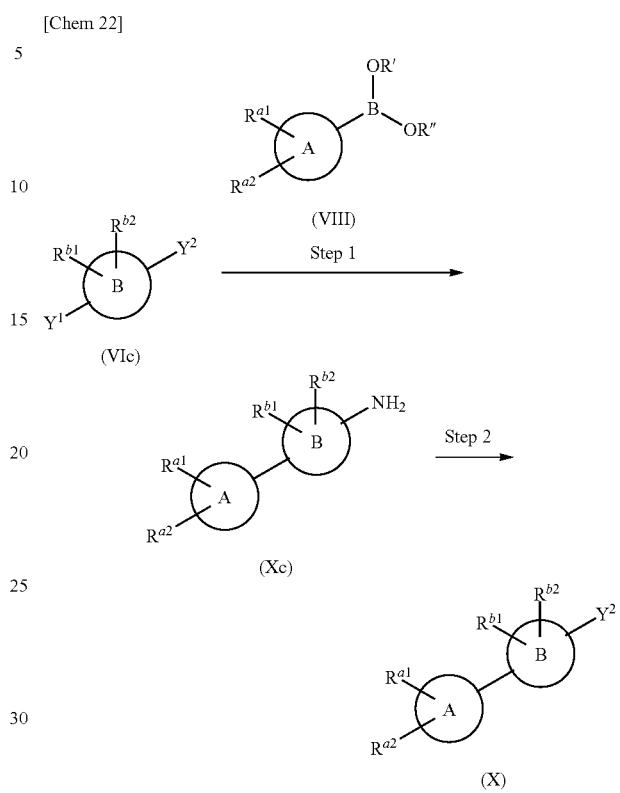

This Process is a process of preparing a compound of formula (X) by a reaction between a compound of formula (VIc) and a compound of formula (VIII) to obtain a compound of formula (Xc), followed by the conversion of the amino group to halogen by the Sandmeyer reaction.

(Step 1)

This step is a step of preparing a compound of formula (Xc) by reaction of a compound of formula (VIc) and a compound of formula (VIII). This reaction is carried out in the same condition as the Step 2a of the Production Process 1, by using the compound of formula (VIc) instead of the compound of formula (VII).

(Step 2)

This step is a step of preparing a compound of formula (X) by conversion of the amino group of a compound of formula (Xc) to a halogen by Sandmeyer reaction. This reaction is carried out by adding a diazotizing reagent to a mixture of the compound of formula (Xc) and an acid in a solvent which is inactive to the reaction under cooling, preferably at 0° C., followed by addition of halogenating reagent under cooling, preferably at 0° C. and stirring at 0° C. to room temperature, typically for 0.1 hours to 5 days. Examples of the diazotizing reagent include, but not limited to, $NaNO_2$, t-butyl nitrite, isoamyl nitrite and the like. Examples of the acid include, but are not limited to, hydrochloric acid, sulfuric acid and the like. Examples of the halogenating reagent include, but are not limited to, CuCl, CuBr, KI and the like. Examples of the solvent include, but are not limited to, water, EtOH, MeOH, THF, 1,4-dioxane, $CH_3CN$, acetone and a mixture thereof. It may be advantageous in some cases, for the smooth progress of the reaction, to carry out the reaction in the presence of urea.

(Other Production Processes)

By using a compound of formula (I) or synthetic intermediates thereof prepared by any of the above-described Production Processes as a starting material, and carrying out further chemical modification reactions typically employed by a person skilled in the art such as alkylation, amidation, acylation, sulfonylation, oxidation, reduction, reductive amination, NH-sulfoximination (Chemical Communications, 53, pp348-351, 2017), protection or deprotection, another compound of formula (I) or synthetic intermediates thereof can be prepared.

The compound of formula (I) is isolated and purified as its free compound, or a salt, a hydrate, a solvate, or crystal polymorph substance thereof. The salt of the compound of formula (I) can also be prepared by a conventional method.

Isolation and purification are carried out by employing general chemical operations such as extraction, fractional crystallization, and various types of fractional chromatography.

Various isomers can be prepared by selecting appropriate starting compound, or separated by separation using differences in the physicochemical properties among the isomers. For example, the optical isomers can be obtained by means of general optical resolution methods of racemic compounds (for example, fractional crystallization introducing the compound into a diastereomer salt with an optically active base or acid; chromatography using a chiral column or the like; and others), or can also be prepared from appropriate optically active starting compound.

The pharmacological activity of the compound of formula (I) can be confirmed by the following test or its modified test which is apparent to the person skilled in the art.

Test Example 1: Test on the Activity of IRF Pathway of THP-1

0.3 uM of PMA (phorbol myristate acetate, SIGMA, P1585) was added to THP1-Dual™ cells (NF-κB-SEAP IRF-Luc Reporter Monocytes, Invivogen, thpd-nfis), and the cells were cultured at 37° C. for 1 day in RPMI1640 with 10% Fetal Bovine Serum (FBS). A compound with a known concentration was added, and the cells were incubated at room temperature for 1 hour. Mammalian (non-canonical) CDN, cyclic [G(2',5')pA(3',5')p] (2'3'-cGAMP, Invivogen, tlrl-nacga23) was added to a final concentration of 5 ug/mL, and the cells were cultured at 37° C. On the following day, QUANTI-Luc™ (Secreted luciferase detection medium, Invivogen, rep-qlc) was added to the culture solution and the activity of IRF pathway was measured using a microplate reader. The inhibition ratio at each concentration was determined, where the activity of IRF pathway with no addition of the test compound or 2'3'-cGAMP was defined as 100% inhibition and the activity of IRF pathway with no addition of the test compound and with addition of 2'3'-cGAMP was defined as 0% inhibition. The $IC_{50}$ value was calculated by sigmoid Exam model non-linear regression analysis.

Table 1 and Table 2 show the results. It was confirmed that the example compounds inhibited the activity of IRF pathway.

TABLE 1

| Ex | $IC_{50}$ (nM) |
|---|---|
| 1 | 13413 |
| 2 | 1090 |
| 3 | 155 |
| 4 | 236 |
| 5 | 950 |
| 6 | 4823 |
| 7 | 2061 |
| 8 | 7752 |
| 9 | 116 |
| 10 | 182 |
| 11 | 146 |
| 12 | 385 |
| 13 | 1545 |
| 14 | 374 |
| 15 | 237 |
| 16 | 229 |
| 17 | 233 |
| 18 | 1407 |
| 19 | 1390 |
| 20 | 244 |
| 21 | 295 |
| 22 | 210 |
| 23 | 91 |
| 24 | 121 |
| 25 | 158 |
| 26 | 299 |
| 27 | 216 |
| 28 | 95 |
| 29 | 153 |
| 30 | 159 |
| 31 | 115 |
| 32 | 178 |
| 33 | 136 |
| 34 | 230 |
| 35 | 466 |
| 36 | 615 |
| 37 | 195 |
| 38 | 88 |
| 39 | 351 |
| 40 | 422 |
| 41 | 792 |
| 42 | 158 |
| 43 | 201 |
| 44 | 174 |
| 45 | 89 |
| 46 | 150 |
| 47 | 277 |
| 48 | 91 |
| 49 | 231 |
| 50 | 48 |
| 51 | 184 |
| 52 | 442 |
| 53 | 550 |
| 54 | 66 |
| 55 | 83 |
| 56 | 256 |
| 57 | 381 |
| 58 | 441 |
| 59 | 444 |
| 60 | 528 |
| 61 | 611 |
| 62 | 594 |
| 63 | 422 |
| 64 | 448 |
| 65 | 340 |
| 66 | 48 |
| 67 | 38 |
| 68 | 64 |
| 69 | 190 |
| 70 | 35 |
| 71 | 43 |
| 72 | 1212 |
| 73 | 99 |
| 74 | 48 |
| 75 | 73 |
| 76 | 76 |
| 77 | 91 |
| 78 | 51 |
| 79 | 185 |
| 80 | 539 |
| 81 | 37 |

TABLE 1-continued

| Ex | IC$_{50}$ (nM) |
|---|---|
| 82 | 239 |
| 83 | 430 |
| 84 | 435 |
| 85 | 224 |
| 86 | 8038 |
| 87 | 1611 |
| 88 | 5550 |
| 89 | 1692 |
| 90 | 471 |
| 91 | 600 |
| 92 | 767 |
| 93 | 919 |
| 94 | 11774 |
| 95 | 1442 |
| 96 | 80 |
| 97 | 4611 |
| 98 | 2566 |
| 99 | 102 |
| 100 | 125 |
| 101 | 190 |
| 102 | 842 |
| 103 | 402 |
| 104 | 1789 |
| 105 | 620 |
| 106 | 358 |
| 107 | 489 |
| 108 | 263 |

TABLE 2

| Ex | IC$_{50}$ (nM) |
|---|---|
| 109 | 112 |
| 110 | 1214 |
| 111 | 1051 |
| 112 | 887 |
| 113 | 698 |
| 114 | 339 |
| 115 | 4937 |
| 116 | 428 |
| 117 | 2831 |
| 118 | 838 |
| 119 | 5255 |
| 120 | 324 |
| 121 | 7776 |
| 122 | 3099 |
| 123 | 143 |
| 124 | 2001 |
| 125 | 322 |
| 126 | 372 |
| 127 | 529 |
| 128 | 70 |
| 129 | 242 |
| 130 | 427 |
| 131 | 578 |
| 132 | 179 |
| 133 | 731 |

Test Example 2: Test on IFNβ Production in Mice Plasma

Male C57BL/6J mice (8-12-weeks-old) were administered orally either vehicle or 1 mg/kg of test compounds. After 1 hour, 5,6-Dimethylxanthenone-4-acetic acid (DMXAA) (BLD Pharmatech Ltd, BD126695) was administered intraperitoneally at a dose of 20 mg/kg. Four hours later, the mice were euthanized, and the plasma was collected. Plasma concentration of IFNβ was measured by an enzyme-linked immunosorbent assay method using an AlphaLISA Mouse IFNβ Detection Kit (Parkin Elmer, AL586C), and the inhibition ratio to the vehicle administration group was calculated.

Table 3 shows the inhibition ratio of the production of IFNβ to the vehicle administration group. It was confirmed that these compounds inhibit the production of IFNβ in vivo.

TABLE 3

| Ex | Inh (%) |
|---|---|
| 33 | 92 |
| 34 | 90 |
| 35 | 83 |
| 36 | 85 |
| 43 | 87 |
| 44 | 82 |
| 46 | 69 |
| 99 | 68 |

Test Example 3: Test on Drug-Induced Sjogren's Syndrome-Like Salivary Dysfunction in Mice Female C57BL/6J mice (8-10-weeks-old) were injected subcutaneously with 20 mg/kg of DMXAA or its vehicle, 5% NaHCO$_3$, four times at weekly intervals. From the day after the last DMXAA challenge, mice were orally administered the test compound or its vehicle once a day for 8 days. On the following day, saliva was collected from mice using a cotton swab under awake conditions, and saliva weight during 15 min was measured and evaluated as an indicator of salivary gland function.

The results of the evaluation of the Example 33, 34 and 99 are shown in FIGS. 1-3. These compounds significantly improved saliva production in mice drug-induced Sjogren's syndrome-like model. From this, it was confirmed that these compounds showed an improving effect on salivary disfunction.

Test Example 4: Trex1 KO Mice Model of Autoimmune Disease

C57BL/6N-Trex1$^{em1Aiwsk}$/J mice (Trex1 KO mice: strain number 032213) were purchased from The Jackson Laboratory. Male Trex1 KO mice and their wild-type (WT) littermates (4-6-weeks-old) were orally administered the test compound or its vehicle once daily for 4 to 9 weeks. Blood, kidneys and other affected tissues were collected for further analysis. Kidneys were stored in RNA protect Tissue Reagent (Qiagen, 76106) and RNA purified using RNeasy Plus Mini Kit (Qiagen, 74134). Reverse transcription and real-time PCR reactions were performed using SuperScript VILO cDNA Synthesis Kit (Life Technologies, 11754250) and TaqMan Gene Expression Master Mix (Life Technologies, 4369016), respectively. Real-time PCR reactions were performed using the equipment in Quant Studio12K Flex (Thermo Fisher Scientific). Probes used were Cxcl10 (Mm00445235_m1), Cd68 (Mm03047343_m1) and Gapdh (Mm99999915_g1), and relative quantification was performed using the ΔΔCT method with Gapdh as the housekeeping gene. A specific compound of formula (I) or a salt thereof significantly reduced Cxcl10 and Cd68 gene expression, which were elevated in the kidneys of Trex1 KO mice.

As a result of the tests above, it was confirmed that some compounds of the formula (I) shown in Table 1 have STING inhibitory action. Moreover, some compounds of formula (I) were demonstrated to inhibit the production of IFNβ induced by DMXAA in mice (Test Example 2). Accordingly, the compound of formula (I) can be used for treating an autoimmune disease, a neurodegenerative disease, a type I interferonopathy and/or other STING-mediated disease.

A pharmaceutical composition comprising one or two or more kinds of the compound of formula (I) as an active ingredient can be prepared using an excipient which is usually used in the art, that is, an excipient for a pharmaceutical preparation, a carrier for a pharmaceutical preparation, and the like, according to a method usually used.

Administration can be accomplished either by oral administration via tablets, pills, capsules, granules, powders, solutions, and the like, or parenteral administration via injections, such as intraarticular, intravenous, and intramuscular injections, suppositories, ophthalmic solution, ophthalmic ointments, transdermal liquid preparations, ointments, transdermal patches, transmucosal liquid preparations, transmucosal patches, inhalers, and the like.

As a solid composition for oral administration, tablets, powders, granules, and the like are used. In such a solid composition, one kind or two or more kinds of the active ingredients are mixed with at least one excipient. In a conventional method, the composition may contain excipients such as a lubricant, a disintegrating agent, a stabilizer, or a solubilization assisting agent. If necessary, tablets, powders and granule may be coated with a wax, a sugar or with a film of a gastric or enteric coating substance.

The liquid composition for oral administration includes pharmaceutically acceptable emulsions, solutions, suspensions, syrups, elixirs, or the like, and also includes generally used diluents, for example, purified water or ethanol. The liquid composition may also include excipients such as a solubilization assisting agent, a moistening agent, a suspending agent, sweeteners, flavors, aromatics, and antiseptics.

The injections for parenteral administration include sterile aqueous or non-aqueous solution preparations, suspensions, or emulsions. The aqueous solvent includes, for example, distilled water for injection and saline. Examples of the non-aqueous solvent include alcohols such as ethanol. Such a composition may further include a tonicity agent, an antiseptic, a moistening agent, an emulsifying agent, a dispersing agent, a stabilizing agent, or a solubilizing assisting agent. These are sterilized, for example, by filtration through a bacteria retaining filter, blending of a bactericide, or irradiation. In addition, these can also be used by preparing a sterile solid composition and dissolving or suspending it in sterile water or a sterile solvent for injection prior to its use.

Examples of the vehicle for external use include ointments, hard plasters, creams, jellies, cataplasms, sprays, lotions, ophthalmic solution, ophthalmic ointments, and the like. The vehicle further contains generally used ointment bases, lotion bases, aqueous or non-aqueous liquid preparations, suspensions, emulsions, and the like.

As the transmucosal agents such as an inhaler and a transnasal agent, those in the form of a solid, liquid, or semi-solid state are used, and can be prepared in accordance with a method known in the related art. For example, a known excipient, and also a pH adjusting agent, an antiseptic, a surfactant, a lubricant, a stabilizing agent, a thickening agent, and the like may be appropriately added thereto. For the administration, an appropriate device for inhalation or blowing can be used. For example, a compound may be administered alone or as a powder of formulated mixture, or as a solution or suspension in combination with a pharmaceutically acceptable carrier, using a known device or sprayer such as a metered administration inhalation device. A dry powder inhaler and the like may be for single or multiple administration use, and a dry powder or a powder-containing capsule may be used. Alternatively, this may be in a form such as a pressurized aerosol spray that uses an appropriate propellant agent, for example, a suitable gas such as chlorofluoroalkanes, carbon dioxide, or other forms.

Usually, in the case of oral administration, the daily dose is from about 0.001 mg/kg to 100 mg/kg, as an embodiment from 0.1 mg/kg to 30 mg/kg, and as another embodiment from 0.1 mg/kg to 10 mg/kg, per body weight, administered in one portion or in 2 to 4 divided portions. In the case of intravenous administration, the daily dose is suitably administered from about 0.0001 mg/kg to 10 mg/kg per body weight, once a day or two or more times a day. In addition, a transmucosal agent is administered at a dose from about 0.001 mg/kg to 100 mg/kg per body weight, once or plural times a day. The dose is appropriately decided in response to the individual case by taking the symptoms, the age, and the gender, and the like into consideration.

Although there are differences depending on a route of administration, a dosage form, an administration site, and a type of the excipient or additive, a pharmaceutical composition of the present invention comprises 0.01% by weight to 100% by weight of, as an embodiment, 0.01% by weight to 50% by weight of, one or more of the compound of formula (I) or a salt thereof which is the active ingredient.

The compound of formula (I) may be used in combination with various agents for treating diseases on which the compound of formula (I) is considered to show the effect. Such combined preparations may be administered simultaneously, or separately and consecutively, or at a desired time interval. The preparations to be co-administered may be a blend, or may be prepared individually.

EXAMPLES

Hereinbelow, the production process for the compound of formula (I) will be described in more detail with reference to Examples. The present invention is not limited to the compounds described in the Examples below. Further, the production processes for the starting compounds will be described in Preparation Examples, and the production processes for the known compounds will be described in Reference Examples. In addition, the production processes for the compound of formula (I) are not limited to the production processes of the specific Examples shown below, but the compound of formula (I) can be prepared by a combination of these production processes or a method that is apparent to a person skilled in the art.

The onset temperatures of endothermic peak and exothermic peak were measured using DSC Q2000 (manufactured by TA Instruments) with an open aluminum sample pan under the following conditions, temperature range: 25° C. to 300° C., heating rate: 10° C./min, nitrogen flow rate: 50 mL/min.

Powder X-ray diffraction was measured using Empyrean (manufactured by Malvern Panalytical) under the following conditions, tube: Cu, tube current: 40 mA, tube voltage: 45 kV, step width: 0.013°, wavelength: 1.5418 Å, measurement diffraction angle range (2θ): 2.5-40°. Due to the nature of the data, the crystal lattice spacing and overall pattern of the powder X-ray diffraction are important in determining crystal identity. The error range of the diffraction angle (2θ (°)) in powder X-ray diffraction is usually ±0.2°, but the diffraction angle and diffraction intensity should not be strictly understood, which may vary to some extent depending on direction of crystal growth, particle size, and measurement conditions.

Moreover, the following abbreviations may be used in Examples, Preparation Examples, and Tables below in some cases.

PEx: Production Example No., Ex: Example No., PSyn: Production Example No. where compounds are produced by the same method (In the case that the number in the PSyn column has E as an initial letter, the compound was produced by using the corresponding starting material in the same manner as the compound having the number of Example compound. For example, the compound in which the PSyn column is E95 means that it was prepared in the same manner as the compound of Example 95. And in the case that the Production Example compound forms a salt, the salt can be formed by a conventional method), Syn: Example No. where compounds are produced by the same method (In the case that the number in the Syn column has P as an initial letter, the compound was produced by using the corresponding starting material in the same manner as the compound having the number of Production Example compound. For example, the compound in which the Syn column is P10 means that it was prepared in the same manner as the compound of Production Example 10. And in the case that the Example compound forms a salt, the salt can be formed by a conventional method), Str: chemical structural formula, DAT: physicochemical data, CI+: m/z value in mass spectrometry (ionization method CI, [M+H]+ unless otherwise specified), EI+: m/z value in mass spectrometry (ionization method EI, M+ unless otherwise specified), ESI+: m/z value in mass spectrometry (ionization method ESI, [M+H]+ unless otherwise specified), ESI−: m/z value in mass spectrometry (ionization method ESI, [M−H]− unless otherwise specified), $^1$H-NMR (CDCl$_3$, 400 MHz): δ (ppm) of signals in $^1$H NMR in CDCl$_3$, $^1$H-NMR (CDCl$_3$, 500 MHz): δ (ppm) of signals in $^1$H NMR in CDCl$_3$, $^1$H-NMR (DMSO-d$_6$, 400 MHz): δ (ppm) of signals in $^1$H NMR in DMSO-d$_6$, $^1$H-NMR (DMSO-d$_6$, 500 MHz): δ (ppm) of signals in $^1$H NMR in DMSO-d$_6$, $^1$H-NMR (CD$_3$OD, 400 MHz): δ (ppm) of signals in $^1$H NMR in CD$_3$OD, J: coupling constant, s: singlet, d: doublet, t: triplet, q: quartet, dd: double doublet, dt: double triplet, dq: double quartet, ddd: double double doublet, br: broad (e.g. br s), m: multiplet, aq.: aqueous solution, sat.: saturated, rt: room temperature, DSC$^1$: onset temperatures of endothermic peaks in DSC measurement, DSC$^2$: onset temperatures of exothermic peaks in DSC measurement, 2θ: diffraction angle of peaks in powder X-ray diffraction.

In the present specification, a naming software such as ACD/Name (registered trademark; Advanced Chemistry Development, Inc.) may be used in some cases.

Compounds whose names are preceded by "rac" are racemates.

In addition, for the sake of convenience, a concentration of mol/L is represented by M. For example, a 1 M aqueous sodium hydroxide solution means a 1 mol/L aqueous sodium hydroxide solution.

Preparation Example 1

Under an argon flow, to a solution of 1-bromo-4-iodo-2-(trifluoromethyl)benzene (1 g) in THF (5 mL) were added CuI (55 mg), PdCl$_2$(PPh$_3$)$_2$ (201 mg), Et$_3$N (4 mL) and trimethylsilylacetylene (0.47 mL) at rt and the mixture was stirred at rt for 1 hour 15 min. The mixture was treated with water at rt, then extracted with CH$_2$Cl$_2$. The organic layer was dried over anhydrous MgSO$_4$, filtered and concentrated under reduced pressure. The residue was purified by silica gel column chromatography (hexane/EtOAc=100/0 to 90/10) to give {[4-bromo-3-(trifluoromethyl)phenyl]ethynyl}(trimethyl)silane (936 mg) as oil.

Preparation Example 6

To a mixture of 4-iodo[1,1'-biphenyl]-2-carbaldehyde (11.2 g) and Pd(PPh$_3$)$_4$ (2.11 g) in DMSO (150 mL) were added prop-2-ynoic acid (3.08 g) and DBU (14.9 g) dropwise at 25-35° C. under nitrogen. The mixture was stirred at 40° C. for 1.5 hours under nitrogen. The mixture was diluted with NaHCO$_3$ aq., extracted with EtOAc. The separated aqueous phase was adjusted pH to 2-3 with cold 1 M HCl aq. to give the suspension. The suspension was filtered and the filtered cake was concentrated to give 3-(2-formyl[1,1'-biphenyl]-4-yl)prop-2-ynoic acid (7.2 g) as a solid.

Preparation Example 7

Under an argon flow, to a solution of 4-bromo-1-(4-fluorophenyl)-5-(trifluoromethyl)-1H-pyrazole (760 mg) in DMF (16 mL) were added Pd(OAc)$_2$ (30 mg), XPhos (122 mg), Et$_3$N (1.1 mL) and trimethylsilylacetylene (0.52 mL) at rt, and the mixture was stirred at 100° C. for 3 hours, then cooled to rt. The mixture was treated with water and brine at rt, then extracted with EtOAc. The organic layer was washed with brine, dried over anhydrous MgSO$_4$, filtered and concentrated under reduced pressure. The residue was purified by silica gel column chromatography (hexane/EtOAc=100/0 to 90/10) to give 1-(4-fluorophenyl)-5-(trifluoromethyl)-4-[(trimethylsilyl)ethynyl]-1H-pyrazole (723 mg) as oil.

Preparation Example 10

A mixture of {[4-bromo-3-(trifluoromethyl)phenyl]ethynyl}(trimethyl)silane (100 mg), phenylboronic acid (57 mg), SPhos (13 mg), Pd(OAc)$_2$ (4 mg), K$_3$PO$_4$ (200 mg), toluene (2 mL) and water (0.5 mL) was stirred at 130° C. for 1 hour under microwave irradiation, then cooled to rt. The mixture was treated with water (10 mL) and EtOAc (10 mL) at rt and extracted with EtOAc. The organic layer was dried over anhydrous MgSO$_4$ (activated carbon powder was added), then filtered and concentrated under reduced pressure. The residue was purified by silica gel column chromatography (hexane/EtOAc=100/0 to 90/10) to give trimethyl{[2-(trifluoromethyl)[1,1'-biphenyl]-4-yl]ethynyl}silane (87 mg) as oil.

Preparation Example 11

Under an argon flow, a mixture of 2-chloro-3-(trifluoromethyl)-5-[(trimethylsilyl)ethynyl]pyridine (862 mg), phenylboronic acid (568 mg), Pd(OAc)$_2$ (35 mg), SPhos (128 mg), K$_3$PO$_4$ (1.98 g), toluene (16 mL) and water (3.5 mL) was stirred at 100° C. for 1 hour, then cooled to rt. The mixture was treated with water and EtOAc at rt and extracted with EtOAc. The organic layer was dried over anhydrous MgSO$_4$ (activated carbon powder was added), then filtered and concentrated under reduced pressure. The residue was purified by silica gel column chromatography (hexane/EtOAc=100/0 to 75/25) to give 2-phenyl-3-(trifluoromethyl)-5-[(trimethylsilyl)ethynyl]pyridine (890 mg) as oil.

Preparation Example 21

To a solution of trimethyl{[2-(trifluoromethyl)[1,1'-biphenyl]-4-yl]ethynyl}silane (9.19 g) in MeOH (150 mL)

was added K$_2$CO$_3$ (6 g) at rt, and the mixture was stirred at rt for 1.5 hours. The mixture was treated with water at rt and extracted with CH$_2$Cl$_2$. The organic layer was dried over anhydrous MgSO$_4$, filtered and concentrated under reduced pressure. The residue was purified by silica gel column chromatography (hexane) to give 4-ethynyl-2-(trifluoromethyl)-1,1'-biphenyl (7.1 g) as oil.

Preparation Example 22

To a solution of 2-phenyl-3-(trifluoromethyl)-5-[(trimethylsilyl)ethynyl]pyridine (887 mg) in MeOH (14 mL) was added K$_2$CO$_3$ (580 mg) at rt, and the mixture was stirred at rt for 1 hour. The mixture was treated with water at rt and extracted with CHCl$_3$. The organic layer was washed with brine, dried over anhydrous MgSO$_4$, filtered and concentrated under reduced pressure. The residue was purified by silica gel column chromatography (hexane/EtOAc=100/0 to 75/25) to give 5-ethynyl-2-phenyl-3-(trifluoromethyl)pyridine (493 mg) as oil.

Preparation Example 23

To a mixture of 1-phenyl-5-(trifluoromethyl)-4-[(trimethylsilyl)ethynyl]-1H-pyrazole (980 mg) in THF (10 mL) was added TBAF (1 M in THF, 4.9 mL). The mixture was stirred at 25-30° C. for 4 hours. The reaction mixture was concentrated and the residue was diluted with water, extracted with EtOAc. The organic layer was washed with brine, dried over anhydrous sodium sulfate, filtered and concentrated to give crude product. The crude product was purified by silica gel column chromatography (2.5% EtOAc in petroleum ether) to give 4-ethynyl-1-phenyl-5-(trifluoromethyl)-1H-pyrazole (750 mg) as oil.

Preparation Example 31

Under an argon flow, to an ice-water-bath cooled solution of 4-ethynyl-2-(trifluoromethyl)-1,1'-biphenyl (7.1 g) in THF (100 mL) was added nBuLi (26 mL, 1.57M in hexane) dropwise, and the mixture was stirred at rt for 0.5 hours. The mixture was poured into dry-ice in a 1000 mL beaker quickly, then stirred at rt in water bath for 0.5 hours. To the mixture was added 0.5 M HCl aq. (150 mL) slowly at rt, then stirred at rt for 10 min. The mixture was extracted with EtOAc. The organic layer was dried over anhydrous MgSO$_4$, filtered and concentrated under reduced pressure to give the crude product as a solid. The obtained solid was treated with IPE and hexane at rt. The solution was extracted with 0.5 M NaOH aq. solution. The aqueous layer was treated with 1 M HCl aq. at rt, then extracted with EtOAc. The organic layer was dried over anhydrous MgSO$_4$, filtered and concentrated under reduced pressure to give the product. The obtained solid was treated with hexane and IPE at rt, then stirred at rt for 5 min. The solid was collected by filtration, washed with hexane and dried in vacuo to give 3-[2-(trifluoromethyl)[1,1'-biphenyl]-4-yl]prop-2-ynoic acid (3.35 g) as a solid. The filtrate was concentrated under reduced pressure. The residue was purified by silica gel column chromatography (CHCl$_3$/MeOH=100/0 to 70/30) to give 3-[2-(trifluoromethyl)[1,1'-biphenyl]-4-yl]prop-2-ynoic acid (2.81 g) as a solid.

Preparation Example 32

Under an argon flow, to a dry-ice-acetone-bath cooled solution of 5-ethynyl-2-phenyl-3-(trifluoromethyl)pyridine (582 mg) in THF (10 mL) was added nBuLi (1.8 mL, 1.57 M in hexane) dropwise, and the mixture was stirred at the same temperature for 20 minutes. To the mixture was added dry-ice, then the mixture was warmed up to rt for 0.5 hours. To the mixture were added 1M NaOH aq. and water at rt, then the mixture was washed with Et$_2$O. The organic layer was extracted with water twice. The combined aqueous layer was treated with 10% citric acid aq. at rt, then extracted with CHCl$_3$—IPA (5:1, v/v). The organic layer was dried over anhydrous MgSO$_4$, filtered and concentrated under reduced pressure to give 3-[6-phenyl-5-(trifluoromethyl)pyridin-3-yl]prop-2-ynoic acid (544 mg) as a solid.

In Preparation Examples 33-36, a reaction was conducted in the similar manner to that of Preparation Example 31. The reaction mixture was concentrated after the stirring with dry-ice, and no further treatment was conducted to give a lithium salt of a target carboxylic acid.

Preparation Example 43

To a mixture of 3-(4-bromophenyl)prop-2-ynoic acid (500 mg) and 1-methylpiperazine (267 mg) in THF (10 mL) were added DIPEA (1.2 mL) and T3P (registered trademark) (1.70 g, 50% in EtOAc). The mixture was stirred at 20° C. for 16 hours. The mixture was combined with another batch. The combined mixture was treated with water and extracted with EtOAc three times. The combined organic phase was washed with brine, dried over anhydrous sodium sulfate, filtered and the filtrate was concentrated to dryness. The residue was purified by reversed phase column chromatography [C18, 10-20% CH$_3$CN in water (0.05% NH$_3$·H$_2$O)]. The combined flows were concentrated to remove CH$_3$CN, and the aqueous phase was extracted with EtOAc three times. The combined organic phase was washed with brine, dried over anhydrous sodium sulfate, filtered and the filtrate was concentrated to dryness to give 3-(4-bromophenyl)-1-(4-methylpiperazin-1-yl)prop-2-yn-1-one (970 mg) as a solid.

Preparation Example 45

To a solution of tert-butyl 4-(3-{1-[4-(trifluoromethyl)phenyl]-1H-pyrazol-4-yl}prop-2-ynoyl)piperazine-1-carboxylate (108 mg) in CH$_2$Cl$_2$ (2 mL) was added TFA (100 uL). The mixture was stirred at 28-32° C. for 1 hour. The reaction mixture was concentrated to give 1-(piperazin-1-yl)-3-{1-[4-(trifluoromethyl)phenyl]-1H-pyrazol-4-yl}prop-2-yn-1-one monotrifluoroacetate (157 mg) as a solid.

Preparation Example 47

A mixture of methyl 3-aminobenzoate (102 mg), 3-[2-(trifluoromethyl)[1,1'-biphenyl]-4-yl]prop-2-ynoic acid (150 mg), DIPEA (242 mg) and HATU (491 mg) in DMF (3 mL) was stirred at rt for 13 hours. The mixture was treated with EtOAc and water at rt, then extracted with EtOAc. The organic layer was washed with 10% citric acid aq., sat. NaHCO$_3$ aq. and brine, and dried over anhydrous MgSO$_4$, filtered and concentrated under reduced pressure. The residue was purified by silica gel column chromatography twice (hexane/EtOAc=90/10 to 50/50) to give methyl 3-({3-[2-(trifluoromethyl)[1,1'-biphenyl]-4-yl]prop-2-ynoyl}amino)benzoate (47 mg) as a solid.

Preparation Example 48

To a mixture of 3-(4-bromophenyl)prop-2-ynoic acid (2 g) in DMF (20 mL) were added 2-anilinoethan-1-ol (1.34 mL), 2-chloro-1-methylpyridinium iodide (3.4 g) and DIPEA (2.28 mL). The mixture was stirred at rt for 1 hour. After addition of water, the mixture was extracted with EtOAc. The organic layer was washed with brine, dried over anhydrous $MgSO_4$, filtered and concentrated in vacuo. The residue was purified by silica gel column chromatography twice (hexane/EtOAc=75/25 to 0/100) to give 3-(4-bromophenyl)-N-(2-hydroxyethyl)-N-phenylprop-2-ynamide (2.72 g) as a solid.

Preparation Example 50

To a solution of 4-iodo-3-(trifluoromethyl)-1H-pyrazole (1 g) in $CH_2Cl_2$ (20 mL) were added phenylboronic acid (1 g), $Cu(OAc)_2$ (600 mg) and pyridine (600 uL), then the reaction mixture was stirred at 25-30° C. for 12 hours under oxygen atmosphere. The mixture was concentrated, and the residue was diluted with water, extracted with EtOAc. The organic layer was washed with brine, dried over anhydrous sodium sulfate, filtered and concentrated to give crude product. The crude product was purified by silica gel column chromatography (0.9% EtOAc in petroleum ether) to give 4-iodo-1-phenyl-3-(trifluoromethyl)-1H-pyrazole (1.28 g) as oil.

Preparation Example 51

To a mixture of 1-(piperazin-1-yl)-3-[2-(trifluoromethyl)[1,1'-biphenyl]-4-yl]prop-2-yn-1-one monotrifluoroacetate (480 mg) in DMF (10 mL) was added $K_2CO_3$ (336 mg) and ethyl 4-bromobutanoate (239 mg), then the reaction mixture was stirred at 25-35° C. for 48 hours. This mixture was combined with another batch, diluted with water, extracted with EtOAc. The organic layer was washed with brine, dried over anhydrous sodium sulfate, filtered and concentrated to give the crude. The crude was purified by reversed phase column chromatography (C18, 50-60% $CH_3CN$ in water/0.05% HCl) and lyophilized to give ethyl 4-(4-{3-[2-(trifluoromethyl)[1,1'-biphenyl]-4-yl]prop-2-ynoyl}piperazin-1-yl)butanoate monohydrochloride (260 mg) as a solid.

Preparation Example 52

To a mixture of methyl 3-[3'-(difluoromethoxy)-2-(trifluoromethyl)[1,1'-biphenyl]-4-yl]prop-2-ynoate (1.2 g), THF (5 mL) and MeOH (5 mL) was added 1 M NaOH aq. (5 mL) at rt. The mixture was stirred at rt for 1 hour and washed with $Et_2O$. To the separated aqueous extract was added 1 M HCl aq. (5 mL) and EtOH. The mixture was concentrated in vacuo. To the residue was added EtOH and then the mixture was filtered to remove the insoluble material. The filtrate was concentrated in vacuo to give 3-[3'-(difluoromethoxy)-2-(trifluoromethyl)[1,1'-biphenyl]-4-yl]prop-2-ynoic acid (1.15 g) as a solid.

Preparation Example 56

To a solution of methyl 4-iodo[1,1'-biphenyl]-2-carboxylate (14.7 g) in $CH_2Cl_2$ (150 mL) was added DIBAL-H (156 mL, 1.0 M in toluene) at −78° C. for 0.5 hours under nitrogen. The mixture was stirred at 25-30° C. for another 3 hours under nitrogen. The mixture was poured into water and diluted with 2 M HCl aq. until the mixture was turned to clear. The mixture was extracted with $CH_2Cl_2$. The organic layer was washed with brine, dried over anhydrous sodium sulfate, filtered and concentrated to give the crude. The crude was purified by silica gel column chromatography (8-15% EtOAc in petroleum ether) to give (4-iodo[1,1'-biphenyl]-2-yl)methanol (12.2 g) as oil.

Preparation Example 57

To a solution of (4-iodo[1,1'-biphenyl]-2-yl)methanol (12.2 g) in $CH_2Cl_2$ (150 mL) was added $MnO_2$ (30 g) and the reaction mixture was stirred at 50° C. for 12 hours. After cooled to room temperature, the reaction mixture was filtered through Celite (registered trademark). The filtrate was concentrated to give 4-iodo[1,1'-biphenyl]-2-carbaldehyde (11.2 g) as oil.

Preparation Example 58

To a solution of 3-(2-formyl[1,1'-biphenyl]-4-yl)prop-2-ynoic acid (1 g) in $CH_2Cl_2$ (15 mL) were added DMF (29.2 mg) and $(COCl)_2$ (420 uL) at 0° C. and stirred at 0° C. for 0.5 hours. The mixture was added to a mixture of (2S)-3-aminopropane-1,2-diol (728 mg) and $Na_2CO_3$ (1.69 g) in water (20 mL) and $CH_2Cl_2$ (20 mL). The reaction mixture was stirred at 0° C. for 1 hour, diluted with water, and extracted with $CHCl_3$/IPA (3/1, v/v). The organic layer was dried over anhydrous sodium sulfate, filtered and concentrated to give the crude. The crude was purified by silica gel column chromatography (5% MeOH in $CH_2Cl_2$) to give N-[(2S)-2,3-dihydroxypropyl]-3-(2-formyl[1,1'-biphenyl]-4-yl)prop-2-ynamide (738 mg) as a solid.

Preparation Example 59

A solution of 3-[2-(trifluoromethyl)[1,1'-biphenyl]-4-yl]prop-2-ynoic acid (100 mg) in $CH_2Cl_2$ (1.02 mL) were added $Et_3N$ (130 uL), rac-methyl (3R)-pyrrolidine-3-carboxylate monohydrochloride (68 mg) and COMU (192 mg) at 0° C. The mixture was stirred at rt for 1 hour. After addition of sat. $NaHCO_3$ aq., the mixture was extracted with EtOAc. The separated organic extracts were washed with sat. $NaHCO_3$ aq., 1 M HCl aq. and brine, filtered through a phase-separator and concentrated under reduced pressure. The residue was purified by silica gel column chromatography (EtOAc/hexane: 50/50 to 100/0, then $CHCl_3$/MeOH=90/10) to give rac-methyl 1-{3-[2-(trifluoromethyl)[1,1'-biphenyl]-4-yl]prop-2-ynoyl}-(3R)-pyrrolidine-3-carboxylate (96.6 mg) as oil.

Preparation Example 60

To a solution of 4-(3,6-dihydro-2H-pyran-4-yl)-3-(trifluoromethyl)phenol (2.6 g) in MeOH (25 mL) was added Pd/C (260 mg, 10%) under hydrogen atmosphere. The mixture was stirred at rt for 24 hours. The reaction mixture was filtered through a pad of Celite (registered trademark). The filtrate was concentrated under reduced pressure to give 4-(oxan-4-yl)-3-(trifluoromethyl)phenol (2.51 g) as a solid.

Preparation Example 61

To a solution of 4-(oxan-4-yl)-3-(trifluoromethyl)phenol (2.5 g) and 1,1,1-trifluoro-N-phenyl-N-((trifluoromethyl)sulfonyl) methanesulfonamide (7.26 g) in $CH_2Cl_2$ (30 mL) was added DIPEA (2.6 g). The mixture was stirred at rt for 3 hours. The reaction was concentrated under reduced pressure. The residue was purified by silica gel column chromatography (0-9% EtOAc in hexane) to afford 4-(oxan-4-yl)-3-(trifluoromethyl)phenyl trifluoromethanesulfonate (3.56 g) as oil.

Preparation Example 63

Under an argon flow, to a solution of 2-chloro-5-iodo-3-(trifluoromethyl)pyridine (1 g) in THF (10 mL) were added CuI (63 mg), $PdCl_2(PPh_3)_2$ (137 mg), $Et_3N$ (4.6 mL) and trimethylsilylacetylene (0.54 mL) at rt and the mixture was stirred at rt for 1 hour. The mixture was treated with water, then extracted with $CHCl_3$. The organic layer was dried over anhydrous $MgSO_4$, filtered and concentrated under reduced pressure. The residue was purified by silica gel column chromatography (hexane/EtOAc=100/0 to 95/5) to give 2-chloro-3-(trifluoromethyl)-5-[(trimethylsilyl)ethynyl]pyridine (867 mg) as oil.

Preparation Example 92

A mixture of 8-chloro-5-[(trimethylsilyl)ethynyl]quinoline (400 mg), [2-(trifluoromethyl)phenyl]boronic acid (460 mg), $Pd(OAc)_2$ (36 mg), $K_2CO_3$ (440 mg) and XPhos (148 mg) in dioxane (40 mL) and water (13.3 mL) was degassed and purged with nitrogen, and then the mixture was stirred at 90° C. for 2 hours under nitrogen atmosphere. The mixture was combined with another batch (the same reaction was conducted with 400 mg of 8-chloro-5-[(trimethylsilyl)ethynyl]quinoline). The mixture was treated with water, extracted with EtOAc, washed with brine, dried over anhydrous sodium sulfate and filtered. The filtrate was concentrated. The crude product was purified by silica gel column chromatography (EtOAc/petroleum ether=12/88 to 13/87) to give 5-ethynyl-8-[2-(trifluoromethyl)phenyl]quinoline (580 mg) as a solid.

Preparation Example 127

A mixture of $K_2CO_3$ (2.77 g) and 5-bromo-2-iodophenol (2 g) in DMF (10 mL) was stirred at 20° C. for 1 hour. To the mixture was added 2-iodopropane (3.41 g) and the mixture was stirred at 70° C. for 3 hours. The reaction mixture was diluted with water and extracted with EtOAc. The separated organic layer was washed with water, dried over anhydrous sodium sulfate, and concentrated under reduced pressure to give 4-bromo-1-iodo-2-[(propan-2-yl)oxy]benzene (2 g) as oil.

Preparation Example 135

To a solution of 3-[2-(trifluoromethyl)[1,1'-biphenyl]-4-yl]prop-2-ynoic acid (100 mg) in $CH_2Cl_2$ (3 mL) were added $Et_3N$ (120 uL), 2-(methylsulfanyl)ethan-1-amine (39 uL) and PyBOP (233 mg) in ice-water bath. The mixture was stirred at rt for 15 hours, treated with sat. $NaHCO_3$ aq., and extracted with $CHCl_3$. The organic layer was washed with sat. $NaHCO_3$ aq., 1 M HCl aq. and water, then concentrated under reduced pressure. The crude product was purified by silica gel column chromatography (EtOAc/hexane=10/90 to 50/50) to give N-[2-(methylsulfanyl)ethyl]-3-[2-(trifluoromethyl)[1,1'-biphenyl]-4-yl]prop-2-ynamide (103 mg) as a solid.

Preparation Example 136

A mixture of methyl 3-[4-bromo-3-(trifluoromethyl)phenyl]prop-2-ynoate (500 mg), 2-(tributylstannyl)pyridine (780 mg) and $Pd(PPh_3)_4$ (94 mg) in toluene (10 mL) was stirred at 150° C. for 3 hours under nitrogen on microwave. The mixture was combined with 4 other batches (the same reaction was conducted four times with 500 mg of 3-[4-bromo-3-(trifluoromethyl)phenyl]prop-2-ynoate for each batch) and concentrated. The crude product was purified by silica gel column chromatography (EtOAc/petroleum ether=15/85) to give methyl 3-[4-(pyridin-2-yl)-3-(trifluoromethyl)phenyl]prop-2-ynoate (1.43 g) as oil.

Preparation Example 137

A mixture of 3-[2'-(benzyloxy)-2-(trifluoromethyl)[1,1'-biphenyl]-4-yl]-1-[(3R,4S)-3,4-dihydroxypyrrolidin-1-yl]prop-2-yn-1-one (280 mg) in TFA (5 mL) was stirred at 80° C. for 16 hours and concentrated. The crude product was purified by reversed phase column (C18, 50-70% MeOH in water/0.05% TFA) to give 1-[(3R,4S)-3,4-dihydroxypyrrolidin-1-yl]-3-[2'-hydroxy-2-(trifluoromethyl)[1,1'-biphenyl]-4-yl]prop-2-yn-1-one as a solid.

Preparation Example 138

To a solution of 3-[2-(trifluoromethyl)[1,1'-biphenyl]-4-yl]prop-2-ynoic acid (155 mg) in $CH_2Cl_2$ (2 mL) was added 1-chloro-N,N,2-trimethylprop-1-en-1-amine (85 uL) in an ice-water bath and the mixture was stirred for 15 min. The above solution was added dropwise to a mixture of N-{3-[(2-{[tert-butyldi(methyl)silyl]oxy}ethyl)amino]propyl}methanesulfonamide (166 mg) and sat. $NaHCO_3$ aq. (2.0 mL) in an ice-water bath. The mixture was stirred at the same temperature for 45 min. The resultant mixture was treated with water and extracted with $CHCl_3$. The separated organic layer was concentrated under reduced pressure. The crude product was purified by silica gel column chromatography (EtOAc/hexane=20/80 to 67/33) to give N-(2-{[tert-butyldi(methyl)silyl]oxy}ethyl)-N-{3-[(methanesulfonyl)amino]propyl}-3-[2-(trifluoromethyl)[1,1'-biphenyl]-4-yl]prop-2-ynamide (322 mg) as oil.

Preparation Example 139

To a mixture of N-(3-aminopropyl)methanesulfonamide (100 mg) in MeOH (3 mL) was added {[tert-butyldi(methyl)silyl]oxy}acetaldehyde (126 mg) at rt. The mixture was stirred at rt for 1 hour. To the mixture was added $NaBH_4$ (27.1 mg) at rt. The mixture was stirred at rt for 2 hours, treated with water, $CHCl_3$ and $NH_4Cl$ aq., and extracted with $CHCl_3$. The organic layer was dried over anhydrous sodium sulfate, filtered and concentrated under reduced pressure. The crude product was purified by silica gel column chromatography ($CHCl_3$/MeOH=100/0 to 80/20) to give N-{3-[(2-{[tert-butyldi(methyl)silyl]oxy}ethyl)amino]propyl}methanesulfonamide (168 mg) as oil.

Preparation Example 141

A mixture of methyl 4-amino-2'-(trifluoromethyl)[1,1'-biphenyl]-2-carboxylate (11.4 g) and 3 M HCl aq. (39.2 mL) in acetone (300 mL) was cooled to 0° C. and a solution of $NaNO_2$ (2.94 g) in water (50 mL) was added dropwise. The mixture was stirred at 0° C. for 1 hour. Urea (881 mg) was added followed by a solution of KI (11.2 g) in water (50 mL) at 0° C. The mixture was stirred at 0° C. for 1 hour. The mixture was stirred at 15-20° C. for 1 hour. The mixture was diluted with water, extracted with EtOAc. The organic layer was washed with brine, dried over anhydrous sodium sulfate, filtered and concentrated. The crude product was purified by silica gel column chromatography (EtOAc/petroleum ether=5/95 to 10/90) to give methyl 4-iodo-2'-(trifluoromethyl)[1,1'-biphenyl]-2-carboxylate (8.2 g) as oil.

Preparation Example 142

To a mixture of tert-butyl (2-aminoethyl)carbamate (500 mg) in $CH_2Cl_2$ (15 mL) was added $Et_3N$ (1.30 mL) followed by methyl (chlorosulfonyl)acetate (648 mg) at 0° C. and stirred at 15-20° C. for 1 hour. The mixture was diluted with water and extracted with EtOAc. The organic layer was washed with brine, dried over anhydrous sodium sulfate, filtered and concentrated. The crude product was purified by silica gel column chromatography (EtOAc/petroleum ether=50/50 to 60/40) to give methyl 10,10-dimethyl-3,3,8-trioxo-9-oxa-3$\lambda^6$-thia-4,7-diazaundecan-1-oate (310 mg) as a gum.

Preparation Example 143

To a solution of methyl 10,10-dimethyl-3,3,8-trioxo-9-oxa-3$\lambda^6$-thia-4,7-diazaundecan-1-oate (310 mg) in THF (5 mL) was added $LiBH_4$ (46 mg) at 0-4° C. The mixture was stirred at 0-4° C. for 1.5 hours. The mixture was poured into sat. $NH_4Cl$ aq. and extracted with EtOAc, dried over anhydrous sodium sulfate, filtered, concentrated to give tert-butyl {2-[(2-hydroxyethanesulfonyl)amino]ethyl}carbamate (250 mg) as oil.

Preparation Example 144

To a solution of 1-(4-fluorophenyl)-2-(trifluoromethyl)-1H-imidazole (1.2 g) in $H_2SO_4$ (12 mL) and water (12 mL) was added NIS (7.0 g) at 0° C. The mixture was stirred for 10 min at 0° C., then the mixture was stirred at 70° C. for 16 hours. The reaction mixture was adjusted pH to 8-9 with 30% NaOH aq. and filtered. The filtrate was extracted with EtOAc. The organic layer was washed with brine, dried over anhydrous sodium sulfate, filtered and concentrated. The residue was purified by silica gel column chromatography (EtOAc/petroleum ether=20/80) to give 1-(4-fluorophenyl)-4,5-diiodo-2-(trifluoromethyl)-1H-imidazole (1.35 g) as a solid.

Preparation Example 145

To a solution of 1-(4-fluorophenyl)-4,5-diiodo-2-(trifluoromethyl)-1H-imidazole (1.35 g) in THF (14 mL) was added dropwise ethylmagnesium bromide (945 uL, 3 M in $Et_2O$) at −40° C. The mixture was stirred at −40° C. for 30 min. The reaction mixture was quickly poured into $NH_4Cl$ aq. and extracted with EtOAc. The organic phase was washed with brine, dried over anhydrous sodium sulfate, filtered and concentrated. The crude product was purified by silica gel column chromatography (EtOAc/petroleum ether=18/82) to give 1-(4-fluorophenyl)-4-iodo-2-(trifluoromethyl)-1H-imidazole (0.8 g) as a solid.

Example 1

To a solution of 1-methylpiperazine (180 uL), 3-([1,1'-biphenyl]-2-yl)prop-2-ynoic acid (300 mg), DIPEA (1.05 g) in THF (15 mL) was added T3P (registered trademark) (2.58 g, 50% in EtOAc) at 0° C. The mixture was stirred at rt for 16 hours. The mixture was concentrated under reduced pressure to give a residue. The crude product was purified by reversed phase column chromatography (C18, 5-55% $CH_3CN$ in water/0.1% $NH_3 \cdot H_2O$) to give 3-([1,1'-biphenyl]-2-yl)-1-(4-methylpiperazin-1-yl)prop-2-yn-1-one (110 mg) as a solid.

Example 20

To a solution of 3-[2-(trifluoromethyl)[1,1'-biphenyl]-4-yl]prop-2-ynoic acid (100 mg) in $CH_2Cl_2$ (1 mL) were added $Et_3N$ (130 uL), (3R)-pyrrolidine-3-carboxamide monohydrochloride (62 mg) and COMU (192 mg) at 0° C. The mixture was stirred at rt for 1 hour. To the mixture was added sat. $NaHCO_3$ aq. and the mixture was extracted with EtOAc. The separated organic extracts were washed with sat. $NaHCO_3$ aq., 1 M HCl aq. and brine, filtered through a phase separator and concentrated under reduced pressure. The residue was purified by silica gel column chromatography ($CHCl_3$/MeOH=100/0 to 90/10) to give (3R)-1-{3-[2-(trifluoromethyl)[1,1'-biphenyl]-4-yl]prop-2-ynoyl}pyrrolidine-3-carboxamide (98.3 mg) as a solid.

Example 33

A mixture of (3R,4S)-pyrrolidine-3,4-diol monohydrochloride (63 mg), 3-[2-(trifluoromethyl)[1,1'-biphenyl]-4-yl]prop-2-ynoic acid (99.7 mg), DIPEA (183 mg) and HATU (327 mg) in DMF (2 mL) was stirred at rt for 13 hours. The mixture was treated with EtOAc and water at rt, then extracted with EtOAc. The organic layer was washed with 10% aq. citric acid, sat. $NaHCO_3$ aq., brine, and dried over anhydrous $MgSO_4$, filtered and concentrated under reduced pressure. The residue was purified by silica gel column chromatography twice ($CHCl_3$/MeOH=100/0 to 90/10) to give 1-[(3R,4S)-3,4-dihydroxypyrrolidin-1-yl]-3-[2-(trifluoromethyl)[1,1'-biphenyl]-4-yl]prop-2-yn-1-one (42 mg) as a solid.

Example 34

A mixture of piperidine-4-carboxamide (61 mg), 3-[2-(trifluoromethyl)[1,1'-biphenyl]-4-yl]prop-2-ynoic acid (99.6 mg), DIPEA (93 mg) and HATU (196 mg) in DMF (2 mL) was stirred at rt for 4 hours. The mixture was treated with EtOAc and water at rt, then extracted with EtOAc. The organic layer was washed with sat. $NaHCO_3$ aq. and brine, dried over anhydrous $MgSO_4$, filtered and concentrated under reduced pressure. The residue was purified by silica gel column chromatography ($CHCl_3$/MeOH=100/0 to 90/10) to give the desired product. The obtained product was treated with IPE and hexane at rt, then triturated. The solid was collected by filtration, washed with hexane and dried in vacuo at 50° C. to give 1-{3-[2-(trifluoromethyl)[1,1'-biphenyl]-4-yl]prop-2-ynoyl}piperidine-4-carboxamide (76 mg) as a solid.

Example 35

A mixture of (2S)-3-aminopropane-1,2-diol (43 mg), 3-[2-(trifluoromethyl)[1,1'-biphenyl]-4-yl]prop-2-ynoic acid (99.8 mg), DIPEA (96 mg) and HATU (198 mg) in DMF (2 mL) was stirred at rt for 2 hours. The mixture was treated with EtOAc and water at rt, then extracted with EtOAc. The organic layer was washed with sat. $NaHCO_3$ aq. and brine, dried over anhydrous $MgSO_4$, filtered and concentrated under reduced pressure. The residue was purified by silica gel column chromatography twice ($CHCl_3$/

MeOH=100/0 to 90/10) to give N-[(2S)-2,3-dihydroxypropyl]-3-[2-(trifluoromethyl)[1,1'-biphenyl]-4-yl]prop-2-ynamide (29 mg) as syrup.

Example 36

A mixture of (2R)-3-aminopropane-1,2-diol (43 mg), 3-[2-(trifluoromethyl)[1,1'-biphenyl]-4-yl]prop-2-ynoic acid (99.8 mg), DIPEA (95 mg) and HATU (196 mg) in DMF (2 mL) was stirred at rt for 4 hours. The mixture was treated with EtOAc and water at rt, then extracted with EtOAc. The organic layer was washed with sat. $NaHCO_3$ aq. and brine, dried over anhydrous $MgSO_4$, filtered and concentrated under reduced pressure. The residue was purified by silica gel column chromatography twice ($CHCl_3$/MeOH=100/0 to 90/10) to give N-[(2R)-2,3-dihydroxypropyl]-3-[2-(trifluoromethyl)[1,1'-biphenyl]-4-yl]prop-2-ynamide (14 mg) as syrup.

Example 43

To a mixture of 3-[2-(trifluoromethyl)[1,1'-biphenyl]-4-yl]prop-2-ynoic acid (90 mg) and (3R,4R)-pyrrolidine-3,4-diol (39 mg) were added 2-chloro-1-methylpyridinium iodide (1.4 mL) (0.33 M in DMF) and DIPEA (64 mg), and the mixture was stirred at rt for 2 hours. The mixture was diluted with EtOAc and washed with sat. $NaHCO_3$ aq. and brine, dried over anhydrous $MgSO_4$, filtered and concentrated in vacuo. The residue was purified by preparative LC/MS (XBridge Prep C18 5 m OBD™ 30×150 mm Column: MeOH/10 mM $NH_4HCO_3$ aq. 10/90 to 95/5), and lyophilized to give 1-[(3R,4R)-3,4-dihydroxypyrrolidin-1-yl]-3-[2-(trifluoromethyl)[1,1'-biphenyl]-4-yl]prop-2-yn-1-one (48 mg) as a solid.

Example 44

To a mixture of 3-[2-(trifluoromethyl)[1,1'-biphenyl]-4-yl]prop-2-ynoic acid (100 mg) and (3S,4S)-pyrrolidine-3,4-diol (43 mg) were added 2-chloro-1-methylpyridinium iodide (1.5 mL) (0.35 M in DMF) and DIPEA (77 mg), and the mixture was stirred at rt for 2 hours. The mixture was diluted with EtOAc and washed with sat. $NaHCO_3$ aq. and brine, dried over anhydrous $MgSO_4$, filtered and concentrated in vacuo. The residue was purified by preparative LC/MS (XBridge Prep C18 5 m OBD™ 30×150 mm Column: MeOH/10 mM $NH_4HCO_3$ aq. 10/90 to 95/5), and MeOH was removed under reduced pressure. The residue was extracted with $CHCl_3$ and the organic layer was washed with water, dried over anhydrous $MgSO_4$, filtered and concentrated in vacuo to give a solid, which was treated with IPE and sonicated for a while. The mixture was concentrated in vacuo to give 1-[(3S,4S)-3,4-dihydroxypyrrolidin-1-yl]-3-[2-(trifluoromethyl)[1,1'-biphenyl]-4-yl]prop-2-yn-1-one (42 mg) as a solid.

Example 45

To a mixture of 3-[2-(trifluoromethyl)[1,1'-biphenyl]-4-yl]prop-2-ynoic acid (90 mg) and L-serinamide monohydrochloride (54 mg) were added 2-chloro-1-methylpyridinium iodide (1 mL) (0.45 M in DMF) and DIPEA (102 mg), and the mixture was stirred at rt for 2 hours. The mixture was diluted with EtOAc and washed with sat. $NaHCO_3$ aq. and brine, dried over anhydrous $MgSO_4$, filtered and concentrated in vacuo. The residue was purified by preparative LC/MS (XBridge Prep C18 5 m OBD™ 30×150 mm Column: MeOH/10 mM $NH_4HCO_3$ aq. 10/90 to 95/5), and lyophilized to give $N^2$-{3-[2-(trifluoromethyl)[1,1'-biphenyl]-4-yl]prop-2-ynoyl}-L-serinamide (16 mg) as a solid.

Example 46

To a mixture of 3-[2-(trifluoromethyl)[1,1'-biphenyl]-4-yl]prop-2-ynoic acid (90 mg) and (azetidine-3,3-diyl)dimethanol monohydrochloride (58 mg) were added 2-chloro-1-methylpyridinium iodide (1 mL) (0.45 M in DMF) and DIPEA (103 mg), and the mixture was stirred at rt for 2 hours. The mixture was diluted with EtOAc and washed with sat. $NaHCO_3$ aq. and brine, dried over anhydrous $MgSO_4$, filtered and concentrated in vacuo. The residue was purified by preparative LC/MS (XBridge Prep C18 5 m OBD™ 30×150 mm Column: MeOH/10 mM $NH_4HCO_3$ aq. 10/90 to 95/5) and lyophilized to give oil, which was treated with small amount of $CH_2Cl_2$. The mixture was concentrated in vacuo to give 1-[3,3-bis(hydroxymethyl)azetidin-1-yl]-3-[2-(trifluoromethyl)[1,1'-biphenyl]-4-yl]prop-2-yn-1-one (37 mg) as a solid.

Example 47

A mixture of (3R,4S)-pyrrolidine-3,4-diol monohydrochloride (226 mg), 3-[6-phenyl-5-(trifluoromethyl)pyridin-3-yl]prop-2-ynoic acid (235 mg), 2-chloro-1-methylpyridinium iodide (3.3 mL) (0.5 M in DMF), DIPEA (523 mg) and DMF (2 mL) was stirred at rt for 2 hours. The mixture was treated with EtOAc and water at rt, then extracted with EtOAc. The organic layer was washed with brine, dried over anhydrous $MgSO_4$, filtered and concentrated under reduced pressure. The residue was purified by silica gel column chromatography ($CHCl_3$/MeOH=100/0 to 90/10) to give the desired product as a solid. The obtained solid was treated with IPE (1 mL) and hexane (5 mL) at rt, then triturated. The solid was collected by filtration, washed with hexane and dried in vacuo to give 1-[(3R,4S)-3,4-dihydroxypyrrolidin-1-yl]-3-[6-phenyl-5-(trifluoromethyl)pyridin-3-yl]prop-2-yn-1-one (42 mg) as a solid.

Example 87

Under argon atmosphere, a mixture of 3-(4-bromophenyl)-N-(2-hydroxyethyl)-N-phenylprop-2-ynamide (100 mg), trimethyl(2-pyridyl)tin (75 uL) and $PdCl_2(PPh_3)_2$ (20 mg) in toluene (1 mL) was stirred for 2 hours at 100° C. under microwave irradiation. To the mixture was added potassium fluoride aq. and the resultant mixture was stirred and extracted with $CHCl_3$. The organic layer was concentrated in vacuo. The residue was purified by silica gel column chromatography (hexane/EtOAc=50/50 to 0/100) to give the desired product. The solid was triturated with EtOAc, filtered and dried in vacuo to give N-(2-hydroxyethyl)-N-phenyl-3-[4-(pyridin-2-yl)phenyl]prop-2-ynamide (18 mg) as a solid.

Example 88

A mixture of 3-(4-bromophenyl)-1-(4-methylpiperazin-1-yl)prop-2-yn-1-one (200 mg), 4-pyridylboronic acid (96.0 mg), $Na_2CO_3$ (138 mg) and $Pd(PPh_3)_4$ (76 mg) in 1,4-dioxane (4 mL) and water (0.8 mL) was degassed and purged with nitrogen gas, then the reaction mixture was stirred at 85° C. for 16 hours under nitrogen gas. The mixture was treated with water (30 mL) and extracted with EtOAc three times. The combined organic phase was washed with brine, dried over anhydrous sodium sulfate and filtered and the filtrate was concentrated to dryness. The residue was purified by silica gel column chromatography eluted with 0-10% EtOAc/petroleum ether followed by reversed phase column chromatography (C18, 0-50% $CH_3CN$ in water/0.05% $NH_3·H_2O$) to give the 1-(4-methylpiperazin-1-yl)-3-[4-(pyridin-4-yl)phenyl]prop-2-yn-1-one (67.9 mg) as a solid after lyophilization.

Example 90

A solution of methyl 3-({3-[2-(trifluoromethyl)[1,1'-biphenyl]-4-yl]prop-2-ynoyl}amino)benzoate (47 mg) in THF (1 mL) and MeOH (1 mL) was added 1 M NaOH aq. (0.5 mL) at rt, and the mixture was stirred at rt for 1.5 hours. To the mixture was added 1 M NaOH aq. (0.5 mL) at rt, and the mixture was stirred at rt for 5 hours. The mixture was treated with 1 M HCl aq. (1.0 mL) and water at rt, then extracted with $CHCl_3$. The organic layer was dried over anhydrous $MgSO_4$, filtered and concentrated under reduced pressure. The residue was purified by silica gel column chromatography ($CHCl_3$/MeOH=100/0 to 80/20) to give the desired product. The obtained solid was treated with IPE (1 mL) and hexane (5 mL) at rt, and triturated. The solid was collected by filtration, washed with hexane and dried in vacuo at 50° C. to give 3-({3-[2-(trifluoromethyl)[1,1'-biphenyl]-4-yl]prop-2-ynoyl}amino)benzoic acid (28 mg) as a solid.

Example 91

A mixture of ethyl 3-(piperazin-1-yl)propanoate dihydrochloride (175 mg), 3-[2-(trifluoromethyl)[1,1'-biphenyl]-4-yl]prop-2-ynoic acid (150 mg), DIPEA (0.32 mL), HOBt (7 mg) and EDC·HCl (297 mg) in DMF (3 mL) was stirred at rt for 15 hours. The mixture was treated with EtOAc and water at rt, then extracted with EtOAc. The organic layer was washed with sat. $NaHCO_3$ aq. and brine, dried over anhydrous $MgSO_4$, filtered and concentrated under reduced pressure. The residue was purified by silica gel column chromatography ($CHCl_3$/EtOAc=100/0 to 50/50) to give the desired intermediate as syrup. The obtained intermediate (114 mg) was dissolved with THF (1 mL) and MeOH (1 mL) at rt, then to the solution was added 1 M NaOH aq. (1 mL) at rt. The mixture was stirred at rt for 0.5 hours. The mixture was treated with 1 M HCl aq. (1 mL) and water (10 mL) at rt, then extracted with $CHCl_3$—IPA (5:1, v/v). The organic layer was dried over anhydrous $MgSO_4$, filtered and concentrated under reduced pressure to give the desired product as a solid. The obtained solid was dissolved with THF (3 mL) at rt, then 4 M HCl/dioxane (1 mL) was added to it. The mixture was concentrated under reduced pressure. The residue was treated with IPE (5 mL) at rt, and triturated. The solid was collected by filtration, washed with IPE and dried in vacuo at 50° C. to give 3-(4-{3-[2-(trifluoromethyl)[1,1'-biphenyl]-4-yl]prop-2-ynoyl}piperazin-1-yl)propanoic acid monohydrochloride (79 mg) as a solid.

Example 92

A mixture of methyl 2,3-dihydro-1H-indole-6-carboxylate (120 mg), 3-[2-(trifluoromethyl)[1,1'-biphenyl]-4-yl]prop-2-ynoic acid (150 mg), DIPEA (0.32 mL) and HATU (393 mg) in DMF (3 mL) was stirred at rt for 3 hours. The mixture was treated with EtOAc and water at rt, then extracted with EtOAc. The organic layer was washed with sat. $NaHCO_3$ aq. and brine and dried over anhydrous $MgSO_4$, filtered and concentrated under reduced pressure. The residue was purified by silica gel column chromatography (hexane/EtOAc=95/5 to 50/50) to give the desired intermediate. The intermediate was treated with concentrated HCl aq. (2 mL) and dioxane (2 mL) at rt, and the mixture was stirred at 100° C. for 0.5 hours, then cooled to rt. Since the reaction did not proceed, it was decided to stop the reaction and recover the intermediate. The mixture was treated with water and extracted with $CHCl_3$. The organic layer was dried over anhydrous $MgSO_4$, filtered and concentrated under reduced pressure. The residue was purified by silica gel column chromatography ($CHCl_3$/MeOH=100/0 to 90/10) to give the recovered intermediate. The intermediate was dissolved with THF (4 mL) and $H_2O$ (2 mL) at rt, then LiOH·$H_2O$ (100 mg) was added to the solution. The mixture was stirred at rt for 4 hours and at 50° C. (oil bath temperature) for 6 hours. The mixture was treated with 1 M HCl aq. (5 mL) at rt and extracted with $CHCl_3$. The organic layer was dried over anhydrous $MgSO_4$, filtered and concentrated under reduced pressure. The residue was purified by silica gel column chromatography ($CHCl_3$/MeOH=100/0 to 90/10) to give the desired product, which was treated with IPE and hexane at rt, then triturated. The solid was collected by filtration, washed with hexane and dried in vacuo at 50° C. to give 1-{3-[2-(trifluoromethyl)[1,1'-biphenyl]-4-yl]prop-2-ynoyl}-2,3-dihydro-1H-indole-6-carboxylic acid (10 mg) as a solid.

Example 95

To a mixture of 1-(piperazin-1-yl)-3-{1-[4-(trifluoromethyl)phenyl]-1H-pyrazol-4-yl}prop-2-yn-1-one monotrifluoroacetate (157 mg) in MeOH (10 mL) were added (HCHO)n (37 mg), $Et_3N$ (34 uL) and AcOH (28 uL). The mixture was stirred at 25-30° C. for 0.5 hours, then $NaBH_3CN$ (31 mg) was added and the resulting mixture was stirred for 0.5 hours. The mixture was heated to 50° C. and stirred for 12 hours. The mixture was concentrated in vacuo. The crude product was purified by preparative HPLC (column: Phenomenex (registered trademark)C18 80*40 mm*3 um; mobile phase: water ($NH_3H_2O$)/$CH_3CN$=58/42 to 28/72). Fractions containing the desired compounds were lyophilized to give 1-(4-methylpiperazin-1-yl)-3-{1-[4-(trifluoromethyl)phenyl]-1H-pyrazol-4-yl}prop-2-yn-1-one (40.4 mg) as a solid.

Example 96

To a mixture of N-[(2R)-2,3-dihydroxypropyl]-3-(2-formyl[1,1'-biphenyl]-4-yl)-N-phenylprop-2-ynamide (95 mg) and piperidine (0.05 mL) in MeOH (2 mL) was added AcOH (30 uL). The reaction mixture was stirred at 60° C. for 4 hours. Then to the above mixture was added $NaBH_3CN$ (41 mg) and stirred at 25° C. for another 3 hours. The mixture was combined with another batch and purified by reversed phase column chromatography (C18, 80-100% MeOH in water/0.1% $NH_3·H_2O$) to give N-[(2R)-2,3-dihydroxypropyl]-N-phenyl-3-{2-[(piperidin-1-yl)methyl][1,1'-biphenyl]-4-yl}prop-2-ynamide (64.5 mg) as a solid.

Example 99

To a solution of 1-(thiomorpholin-4-yl)-3-[2-(trifluoromethyl)[1,1'-biphenyl]-4-yl]prop-2-yn-1-one (137 mg) in MeOH (1 mL) and $CH_2Cl_2$ (0.25 mL) were added iodobenzene diacetate (295 mg) and ammonium carbamate (57 mg). The mixture was stirred at rt for 30 min and concentrated under reduced pressure. The resultant residue was purified by silica gel column chromatography (EtOAc/hexane: 30/70 to 100/0 then CHCl$_3$/MeOH=90/10) to give 1-imino-4-{3-[2-(trifluoromethyl)[1,1'-biphenyl]-4-yl]prop-2-ynoyl}-1λ$^6$-thiomorpholin-1-one (134 mg) as a solid.

Example 100

A mixture of tert-butyl (3S)-pyrrolidin-3-ylcarbamate (77 mg), 3-[2-(trifluoromethyl)[1,1'-biphenyl]-4-yl]prop-2-ynoic acid (99.8 mg), 2-chloro-1-methylpyridinium iodide (0.28 M in DMF, 2 mL) and DIPEA (95 mg) in DMF (2 mL) was stirred at rt for 12 hours. The mixture was treated with EtOAc and water at rt, then extracted with EtOAc. The organic layer was washed with sat. NaHCO$_3$ aq. and brine, and dried over anhydrous MgSO$_4$, filtered and concentrated under reduced pressure. The residue was purified by silica gel column chromatography (hexane/EtOAc=100/0 to 50/50) to give the intermediate as syrup. The obtained intermediate was dissolved with CH$_2$Cl$_2$ (2 mL) at rt and to the solution was added TFA (1 mL) at rt. The mixture was stirred at rt for 1 hour and concentrated under reduced pressure. The residue was treated with sat. NaHCO$_3$ aq. (10 mL) and water at rt, then extracted with CHCl$_3$—IPA (5:1, v/v). The organic layer was dried over anhydrous MgSO$_4$, filtered and concentrated under reduced pressure to give the desired product as syrup. The obtained product was dissolved with THF (2 mL), IPE (2 mL) and hexane (5 mL) at rt, then oxalic acid (17 mg) was added to it. The mixture was stirred at rt for 0.5 hours. The solid was collected by filtration, washed with hexane and dried in vacuo at 50° C. to give 1-[(3S)-3-aminopyrrolidin-1-yl]-3-[2-(trifluoromethyl)[1,1'-biphenyl]-4-yl]prop-2-yn-1-one monooxalate (54 mg) as a solid.

Example 106

To a solution of 3-[2-(trifluoromethyl)[1,1'-biphenyl]-4-yl]prop-2-ynoic acid (208 mg) in DMF (10 mL) were added EDC·HCl (187 mg), HOBt (163 mg) and DIPEA (244 mg) under nitrogen atmosphere at 0° C. The mixture was stirred for 1 hour followed by the addition of (1R,2S,4r)-4-aminocyclopentane-1,2-diol (100 mg). The reaction was stirred at rt for 16 hours and then concentrated under reduced pressure. The residue was purified by preparative TLC (CH$_2$Cl$_2$: MeOH=10:1) to give N-[(1r,3R,4S)-3,4-dihydroxycyclopentyl]-3-[2-(trifluoromethyl)[1,1'-biphenyl]-4-yl]prop-2-ynamide (64.6 mg) as a solid.

Example 119

To the mixture of 4-{3-[(3R,4S)-3,4-dihydroxypyrrolidin-1-yl]-3-oxoprop-1-yn-1-yl}-2'-(trifluoromethyl)[1,1'-biphenyl]-2-carboxylic acid (135 mg), NH$_4$Cl (21 mg) and HATU (245 mg) in DMF (3 mL) was added DIPEA (168 uL), and then the mixture was stirred at 50° C. for 16 hours. The mixture was combined with another batch (the same reaction was conducted with 20 mg of 4-{3-[(3R,4S)-3,4-dihydroxypyrrolidin-1-yl]-3-oxoprop-1-yn-1-yl}-2'-(trifluoromethyl)[1,1'-biphenyl]-2-carboxylic acid), diluted with 4% LiCl aq. and extracted with EtOAc. The organic layer was washed with brine, dried over anhydrous sodium sulfate, filtered and concentrated. The crude product was purified by reversed-phase column (C18, 50-60% MeOH in water/0.1% NH$_3$·H$_2$O). The obtained product was purified by reversed-phase column (C18, 45-55% MeOH in water/0.1% NH$_3$·H$_2$O). The crude product was purified by preparative HPLC (column: Phenomenex C18; mobile phase: 20-40% MeCN in water (HCl)) to give 4-{3-[(3R,4S)-3,4-dihydroxypyrrolidin-1-yl]-3-oxoprop-1-yn-1-yl}-2'-(trifluoromethyl)[1,1'-biphenyl]-2-carboxamide (45.7 mg) as a solid by lyophilization.

Example 127

A mixture of tert-butyl methyl[(3R)-1-{3-[4-(pyridin-2-yl)-3-(trifluoromethyl)phenyl]prop-2-ynoyl}pyrrolidin-3-yl]carbamate (257 mg) and TFA (1 mL) in CH$_2$Cl$_2$ (5 mL) was stirred at 10-20° C. for 2 hours. The mixture was concentrated to give the crude, which was purified by reversed-phase column (C18, 50-60% MeOH in water/0.1% NH$_3$·H$_2$O) to afford 1-[(3R)-3-(methylamino)pyrrolidin-1-yl]-3-[4-(pyridin-2-yl)-3-(trifluoromethyl)phenyl]prop-2-yn-1-one (128 mg) as a solid by lyophilization.

Example 128

To a mixture of rac-1-[(3R)-3-(hydroxymethyl)thiomorpholin-4-yl]-3-[2-(trifluoromethyl)[1,1'-biphenyl]-4-yl]prop-2-yn-1-one (308 mg) in CH$_2$Cl$_2$ (8 mL) was added m-CPBA (319 mg) and the reaction mixture was stirred at 10-15° C. for 12 hours. The reaction mixture was quenched by addition of sat. Na$_2$SO$_3$ aq., diluted with water, and extracted with EtOAc. The organic layer was washed with brine, dried over anhydrous sodium sulfate, filtered and concentrated under reduced pressure. The residue was purified by preparative HPLC (column: Phenomenex C18; mobile phase: water (NH$_3$·H$_2$O)/MeCN=60/40 to 30/70). Fractions containing the desired compounds were lyophilized to give rac-(3R)-3-(hydroxymethyl)-4-{3-[2-(trifluoromethyl)[1,1'-biphenyl]-4-yl]prop-2-ynoyl}-1λ$^6$-thiomorpholine-1,1-dione (107 mg) as a solid.

Example 129

To a mixture of 1-[(3R,4S)-3,4-dihydroxypyrrolidin-1-yl]-3-[2'-hydroxy-2-(trifluoromethyl)[1,1'-biphenyl]-4-yl]prop-2-yn-1-one (20 mg) and K$_2$CO$_3$ (22 mg) in DMF (1 mL) was added 3-bromoprop-1-yne (7 uL). The reaction mixture was stirred at 60° C. for 1.5 hours. The reaction mixture was combined with 2 batches (the same reaction was conducted with 30 mg and 85 mg of 1-[(3R,4S)-3,4-dihydroxypyrrolidin-1-yl]-3-[2'-hydroxy-2-(trifluoromethyl)[1,1'-biphenyl]-4-yl]prop-2-yn-1-one for each batch). The resultant mixture was purified by reversed phase column (C18, water (0.1% NH$_3$·H$_2$O)/MeCN=50/50 to 40/60) to give 1-[(3R,4S)-3,4-dihydroxypyrrolidin-1-yl]-3-{2'-[(prop-2-yn-1-yl)oxy]-2-(trifluoromethyl)[1,1'-biphenyl]-4-yl}prop-2-yn-1-one (85.2 mg) as a solid.

Example 130

To a mixture of N-(2-{[tert-butyldi(methyl)silyl]oxy}ethyl)-N-{3-[(methanesulfonyl)amino]propyl}-3-[2-(trifluoromethyl)[1,1'-biphenyl]-4-yl]prop-2-ynamide (317 mg) and THF (5 mL) was added TBAF (1 M in THF, 1 mL) in ice-water bath. The mixture was stirred at the same temperature for 1.5 hours. The mixture was treated with sat. NH$_4$Cl aq. and CHCl$_3$. The separated organic layer was concentrated under reduced pressure. The crude product was purified by silica gel column chromatography (CHCl$_3$/MeOH=100:0 to 92:8). The obtained oil was sonicated with a mixture of EtOAc, IPE and hexane. The resultant mixture was concentrated under reduced pressure. The obtained solid was dissolved with CH₂Cl₂. To the solution was added hexane, and the mixture was concentrated to give N-(2-hydroxyethyl)-N-{3-[(methanesulfonyl)amino]propyl}-3-[2-(trifluoromethyl)[1,1'-biphenyl]-4-yl]prop-2-ynamide (209 mg) as a solid.

Example 131

To a solution of 3-[2'-(trifluoromethyl)[1,1'-biphenyl]-4-yl]prop-2-ynoic acid (32 mg) in CH₂Cl₂ (1 mL) were added Et₃N (42 uL), (3R,4S)-pyrrolidine-3,4-diol monohydrochloride (23 mg) and PyBOP (74 mg). The mixture was stirred at rt for 4 hours, treated with 1 M HCl aq. and water, then extracted by EtOAc. The separated organic layer was concentrated under reduced pressure. The crude product was purified by silica gel column chromatography (CHCl₃/MeOH=100/0 to 90/10) to give 1-[(3R,4S)-3,4-dihydroxypyrrolidin-1-yl]-3-[2'-(trifluoromethyl)[1,1'-biphenyl]-4-yl]prop-2-yn-1-one (36.4 mg) as a solid.

Example 133

To a mixture of dimethylamine hydrochloride (37 mg) and MeOH (2 mL) was added Et₃N (52 uL) and the mixture was stirred at 30° C. for 10 min. To the mixture were added 4-{3-[(3R,4S)-3,4-dihydroxypyrrolidin-1-yl]-3-oxoprop-1-yn-1-yl}-2'-(trifluoromethyl)[1,1'-biphenyl]-2-carbaldehyde (150 mg) and AcOH (26 uL), and the resultant mixture was stirred at 60° C. for 3 hours. NaBH₃CN (39 mg) was added and stirred at 30° C. for 30 min. The mixture was concentrated to give the crude product, which was purified by reversed phase column (C18, 40-50% MeCN in water/0.1% NH₃·H₂O) to give 1-[(3R,4S)-3,4-dihydroxypyrrolidin-1-yl]-3-[2-(hydroxymethyl)-2'-(trifluoromethyl)[1,1'-biphenyl]-4-yl]prop-2-yn-1-one (82.2 mg) as a solid.

Example 134

A mixture of 1-[(3R,4S)-3,4-dihydroxypyrrolidin-1-yl]-3-[2-(trifluoromethyl)[1,1'-biphenyl]-4-yl]prop-2-yn-1-one (300 mg) and EtOAc (3 mL) was stirred at 60° C. for 20 min. The solution was cooled to rt and stirred overnight. The precipitates were collected by filtration and dried at 40° C. under reduced pressure to give 1-[(3R,4S)-3,4-dihydroxypyrrolidin-1-yl]-3-[2-(trifluoromethyl)[1,1'-biphenyl]-4-yl]prop-2-yn-1-one (145 mg) as a solid.

Example 135

A mixture of 1-{3-[2-(trifluoromethyl)[1,1'-biphenyl]-4-yl]prop-2-ynoyl}piperidine-4-carboxamide (100 mg) and EtOH (6 mL) was stirred at 50° C. for 2 hours. The solution was cooled to rt and the precipitates were collected by filtration. The obtained solid was dried at 50° C. under reduced pressure to give 1-{3-[2-(trifluoromethyl)[1,1'-biphenyl]-4-yl]prop-2-ynoyl}piperidine-4-carboxamide (22 mg) as a solid.

Example 136

A small vial containing 1-imino-4-{3-[2-(trifluoromethyl)[1,1'-biphenyl]-4-yl]prop-2-ynoyl}-1λ⁶-thiomorpholin-1-one (134 mg) and EtOAc (500-1000 uL) was placed in a lager vial containing hexane (5-10 mL). The outside vial was sealed and left to stand at rt overnight. The precipitates were collected by filtration and rinsed with EtOAc/hexane (1/1) to give 1-imino-4-{3-[2-(trifluoromethyl)[1,1'-biphenyl]-4-yl]prop-2-ynoyl}-1λ⁶-thiomorpholin-1-one (104 mg) as solid.

The compounds of Preparation Examples and Examples shown in Tables below were produced in the same manner as the methods in Preparation Examples or Examples as described above.

TABLE 4

| PEx | Str |
|---|---|
| 1 | (4-bromo-3-(trifluoromethyl)phenyl)ethynyl-TMS |
| 2 | 1-(4-(trifluoromethyl)phenyl)-1H-pyrazol-4-yl propynoyl piperazine-BOC |
| 3 | 5-(trifluoromethyl)-1-phenyl-1H-pyrazol-4-yl ethynyl-TMS |
| 4 | 3-(trifluoromethyl)-1-phenyl-1H-pyrazol-4-yl ethynyl-TMS |
| 5 | methyl 3-(4-bromo-3-(trifluoromethyl)phenyl)propiolate |
| 6 | 3-(2-formyl-[1,1'-biphenyl]-4-yl)propiolic acid |

TABLE 4-continued
| PEx | Str |
|---|---|
| 7 | 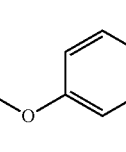 |
| 8 | 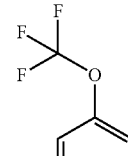 |
| 9 | 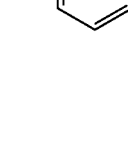 |
| 10 | 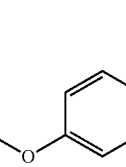 |
| 11 |  |
| 12 | 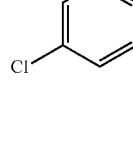 |
| 13 | 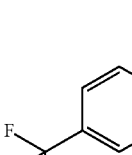 |
| 14 | 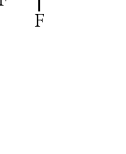 |
| 15 | 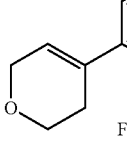 |
| 16 | |
| 17 | |
| 18 | |

TABLE 4-continued

| PEx | Str |
|---|---|
| 19 | 4-(3,6-dihydro-2H-pyran-4-yl)-3-(trifluoromethyl)phenol |
| 20 | 4-(1-tert-butyl-1H-pyrazol-4-yl)-3-(trifluoromethyl)phenol |

TABLE 5

| PEx | Str |
|---|---|
| 21 | 4-ethynyl-2-(trifluoromethyl)-1,1'-biphenyl |
| 22 | 5-ethynyl-2-phenyl-3-(trifluoromethyl)pyridine |
| 23 | 4-ethynyl-1-phenyl-5-(trifluoromethyl)-1H-pyrazole |
| 24 | 4-ethynyl-1-phenyl-3-(trifluoromethyl)-1H-pyrazole |

TABLE 5-continued

| PEx | Str |
|---|---|
| 25 | 4'-ethynyl-2'-(trifluoromethyl)-2-(trifluoromethoxy)-1,1'-biphenyl |
| 26 | 4'-chloro-4-ethynyl-2-(trifluoromethyl)-1,1'-biphenyl |
| 27 | 5-ethynyl-3-(trifluoromethyl)-2-[4-(trifluoromethyl)phenyl]pyridine |
| 28 | 4-ethynyl-1-(4-fluorophenyl)-5-(trifluoromethyl)-1H-pyrazole |
| 29 | 4-(4-ethynyl-2-(trifluoromethyl)phenyl)tetrahydro-2H-pyran |
| 30 | 1-tert-butyl-4-[4-ethynyl-2-(trifluoromethyl)phenyl]-1H-pyrazole |

TABLE 5-continued

| PEx | Str |
|---|---|
| 31 | 3-(4-phenyl-3-(trifluoromethyl)phenyl)propiolic acid |
| 32 | 3-(6-phenyl-5-(trifluoromethyl)pyridin-3-yl)propiolic acid |
| 33 | lithium 3-(5-phenylpyridin-2-yl)propiolate |
| 34 | lithium 3-(6-phenylpyridin-3-yl)propiolate |
| 35 | lithium 3-(1-phenyl-5-(trifluoromethyl)-1H-pyrazol-4-yl)propiolate |
| 36 | lithium 3-(1-phenyl-3-(trifluoromethyl)-1H-pyrazol-4-yl)propiolate |
| 37 | 3-(2'-(trifluoromethoxy)-3-(trifluoromethyl)-[1,1'-biphenyl]-4-yl)propiolic acid |
| 38 | 3-(4'-chloro-3-(trifluoromethyl)-[1,1'-biphenyl]-4-yl)propiolic acid |
| 39 | 3-(5-(trifluoromethyl)-6-(4-(trifluoromethyl)phenyl)pyridin-3-yl)propiolic acid |
| 40 | 3-(1-(4-fluorophenyl)-5-(trifluoromethyl)-1H-pyrazol-4-yl)propiolic acid |

TABLE 6

| PEx | Str |
|---|---|
| 41 | 3-(4-(tetrahydro-2H-pyran-4-yl)-3-(trifluoromethyl)phenyl)propiolic acid |

TABLE 6-continued

| PEx | Str |
|---|---|
| 42 | (structure) |
| 43 | (structure) |
| 44 | (structure) |
| 45 | (structure) |
| 46 | (structure) |
| 47 | (structure) |
| 48 | (structure) |
| 49 | (structure) |
| 50 | (structure) |
| 51 | (structure) |
| 52 | (structure) |
| 53 | (structure) |

TABLE 6-continued
| PEx | Str |
|---|---|
| 54 | 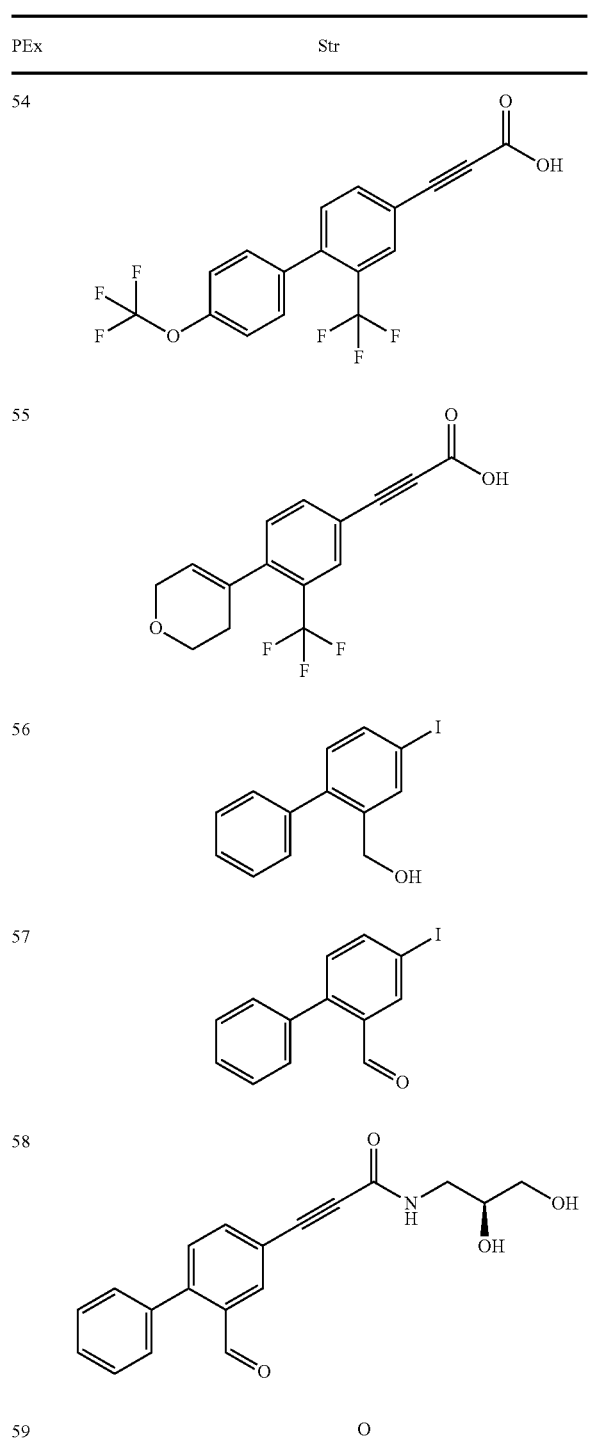 |
| 55 | |
| 56 | |
| 57 | |
| 58 | |
| 59 | |
TABLE 6-continued
| PEx | Str |
|---|---|
| 60 | 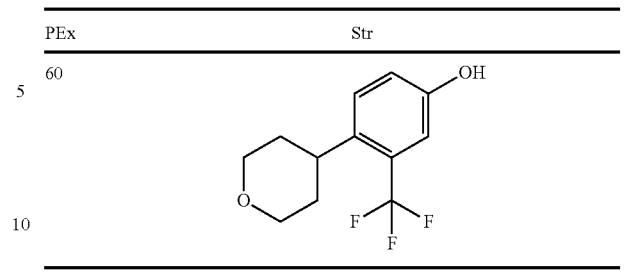 |
TABLE 7
| PEx | Str |
|---|---|
| 61 | 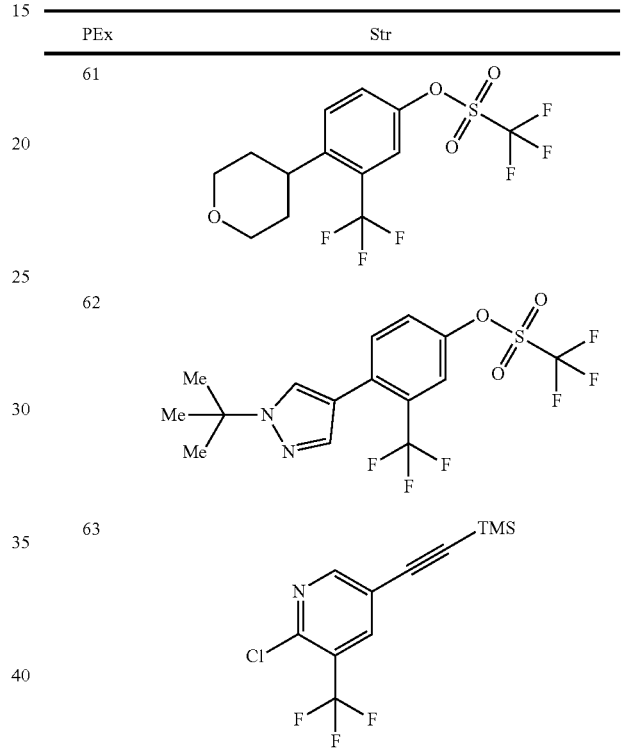 |
| 62 | |
| 63 | |
| 64 | |
TABLE 8
| PEX | Str |
|---|---|
| 65 | 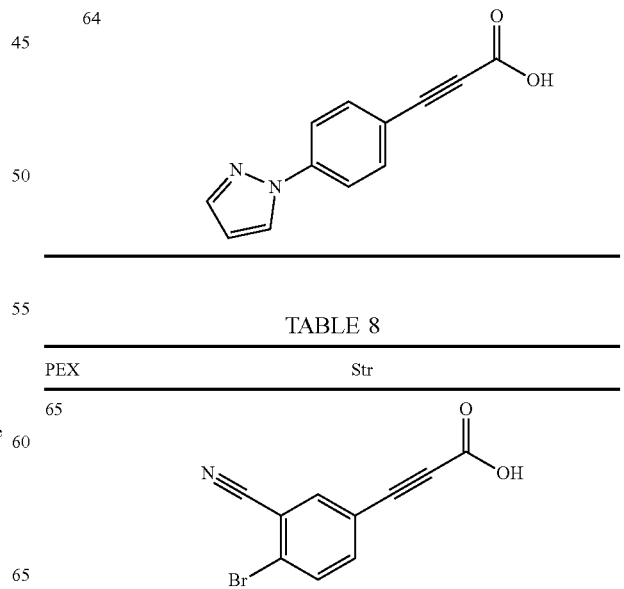 |

TABLE 8-continued
| PEX | Str |
|---|---|
| 66 | 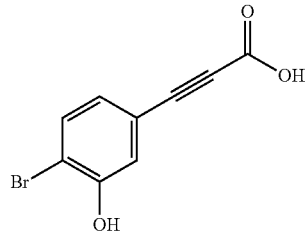 [SMILES: O=C(O)C#Cc1ccc(Br)c(O)c1] |
| 67 | 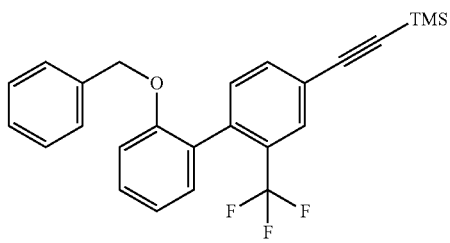 [SMILES: C[Si](C)(C)C#Cc1ccc(-c2ccccc2OCc2ccccc2)c(C(F)(F)F)c1] |
| 68 | 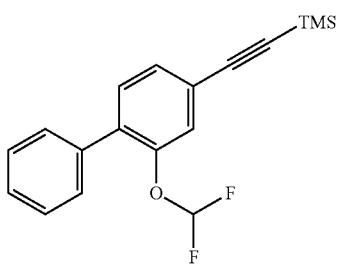 [SMILES: C[Si](C)(C)C#Cc1ccc(-c2ccccc2)c(OC(F)F)c1] |
| 69 | 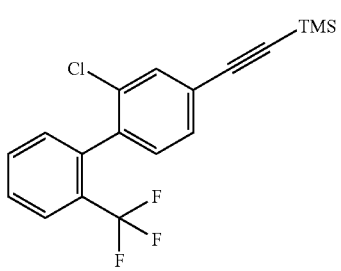 [SMILES: C[Si](C)(C)C#Cc1ccc(-c2ccccc2C(F)(F)F)c(Cl)c1] |
| 70 | 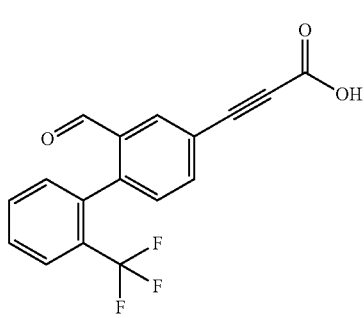 [SMILES: O=Cc1cc(C#CC(=O)O)ccc1-c1ccccc1C(F)(F)F] |
| 71 | 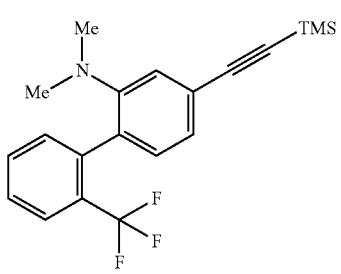 [SMILES: CN(C)c1cc(C#C[Si](C)(C)C)ccc1-c1ccccc1C(F)(F)F] |
| 72 | 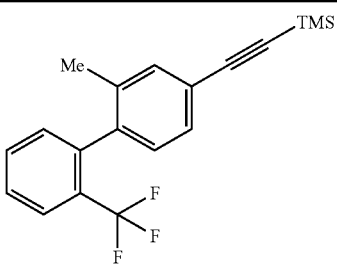 |
| 73 | 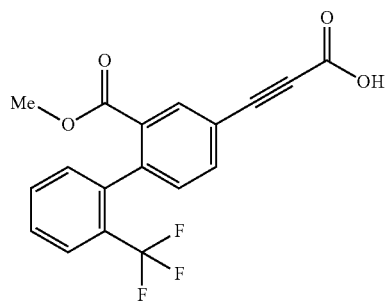 [SMILES: COC(=O)c1cc(C#CC(=O)O)ccc1-c1ccccc1C(F)(F)F] |
| 74 | 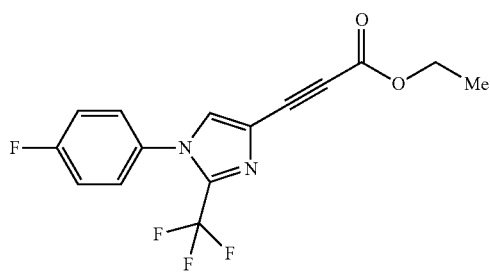 [SMILES: CCOC(=O)C#Cc1cn(-c2ccc(F)cc2)c(C(F)(F)F)n1] |
| 75 | 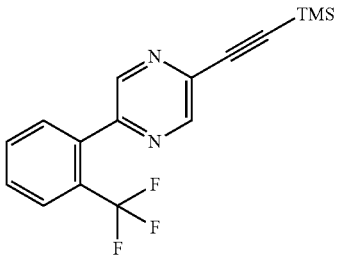 [SMILES: C[Si](C)(C)C#Cc1cnc(-c2ccccc2C(F)(F)F)cn1] |
| 76 | 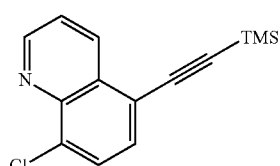 |
| 77 | 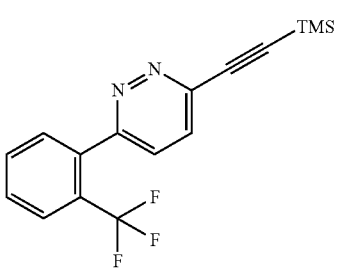 [SMILES: C[Si](C)(C)C#Cc1ccc(-c2ccccc2C(F)(F)F)nn1] |

TABLE 8-continued
| PEX | Str |
|---|---|
| 78 | 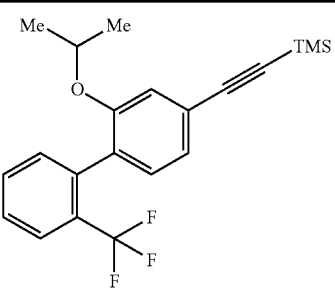 |
| 79 | 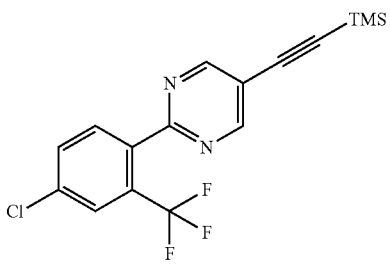 [SMILES: C[Si](C)(C)C#Cc1cnc(-c2ccc(Cl)cc2C(F)(F)F)nc1] |
| 80 | 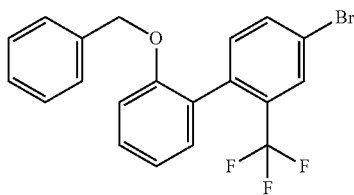 [SMILES: FC(F)(F)c1cc(Br)ccc1-c1ccccc1OCc1ccccc1] |
| 81 | 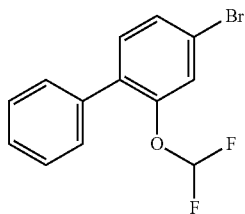 [SMILES: FC(F)Oc1cc(Br)ccc1-c1ccccc1] |
| 82 | 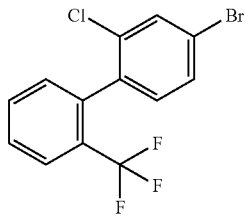 [SMILES: FC(F)(F)c1ccccc1-c1ccc(Br)cc1Cl] |
| 83 | 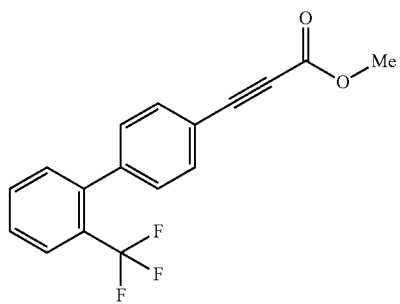 [SMILES: COC(=O)C#Cc1ccc(-c2ccccc2C(F)(F)F)cc1] |
| 84 | 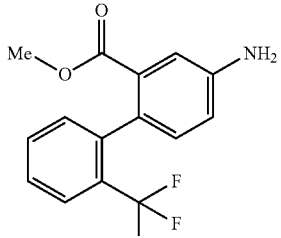 |
TABLE 9
| PEx | Str |
|---|---|
| 85 | 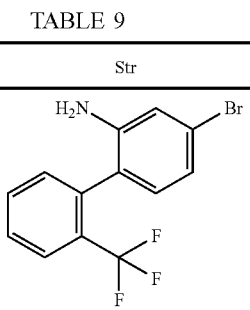 |
| 86 | 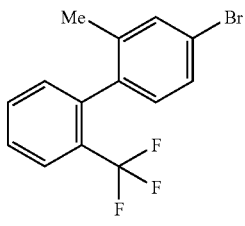 [SMILES: Cc1cc(Br)ccc1-c1ccccc1C(F)(F)F] |
| 87 | 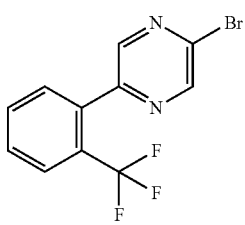 [SMILES: FC(F)(F)c1ccccc1-c1cnc(Br)cn1] |
| 88 | 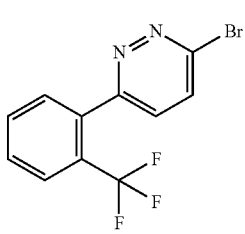 [SMILES: FC(F)(F)c1ccccc1-c1ccc(Br)nn1] |
| 89 | 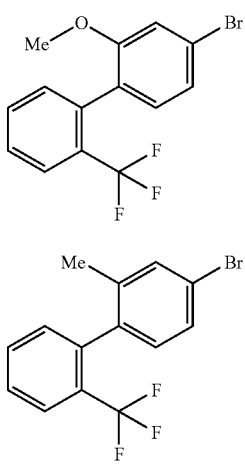 |

TABLE 9-continued
| PEx | Str |
|---|---|
| 90 | 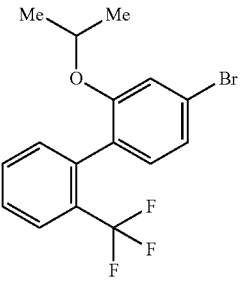 [SMILES: CC(C)Oc1cc(Br)ccc1-c1ccccc1C(F)(F)F] |
| 91 | 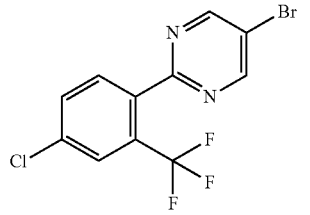 [SMILES: FC(F)(F)c1cc(Cl)ccc1-c1ncc(Br)cn1] |
| 92 | 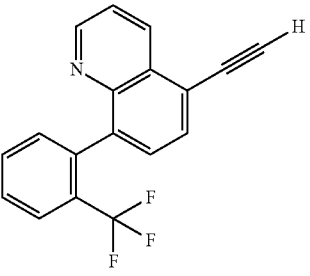 [SMILES: C#Cc1ccc(-c2ccccc2C(F)(F)F)c2ncccc12] |
| 93 | 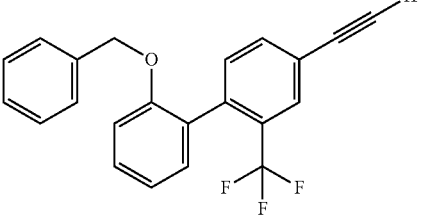 |
| 94 | 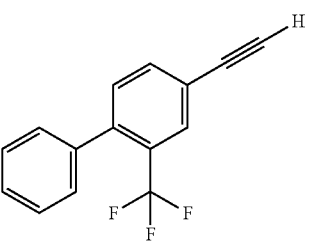 [SMILES: C#Cc1ccc(-c2ccccc2)c(C(F)(F)F)c1] |
| 95 | 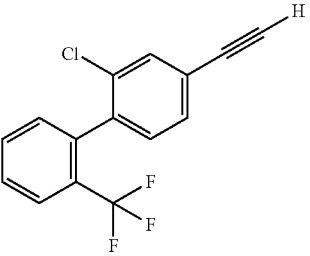 [SMILES: C#Cc1ccc(-c2ccccc2C(F)(F)F)c(Cl)c1] |
| 96 | 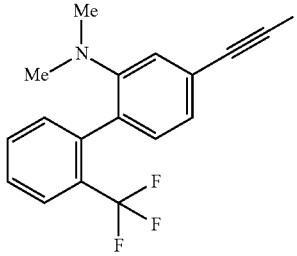 |
| 97 | 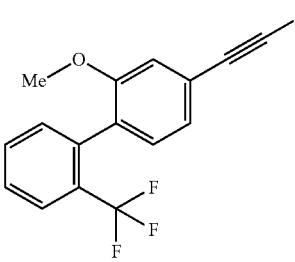 |
| 98 | 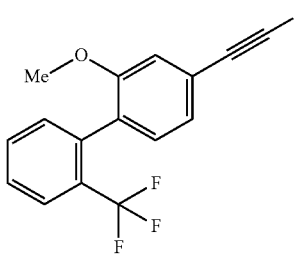 |
| 99 | 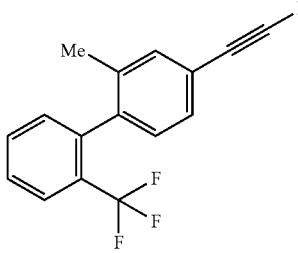 |
| 100 | 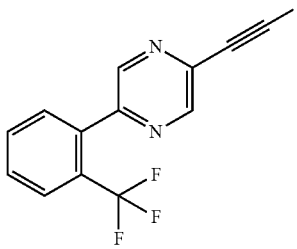 |
| 101 | 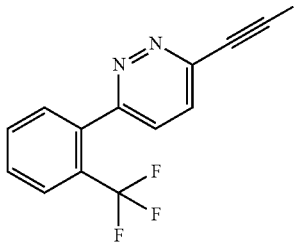 |

TABLE 9-continued

| PEx | Str |
|---|---|
| 102 | (structure) |
| 103 | (structure) |
| 104 | (structure) |

TABLE 10

| PEx | Str |
|---|---|
| 105 | (structure) |
| 106 | (structure) |
| 107 | (structure) |
| 108 | (structure) |
| 109 | (structure) |
| 110 | (structure) |
| 111 | (structure) |

TABLE 10-continued

| PEx | Str |
|---|---|
| 112 | 3-(6-(2-(trifluoromethyl)phenyl)pyridazin-3-yl)propiolic acid |
| 113 | 3-(3-isopropoxy-2'-(trifluoromethyl)-[1,1'-biphenyl]-4-yl)propiolic acid |
| 114 | 3-(2-(4-chloro-2-(trifluoromethyl)phenyl)pyrimidin-5-yl)propiolic acid |
| 115 | 3-(4-bromo-3-cyanophenyl)-1-((3R,4S)-3,4-dihydroxypyrrolidin-1-yl)prop-2-yn-1-one |
| 116 | 3-(4-bromo-3-hydroxyphenyl)-1-((3R,4S)-3,4-dihydroxypyrrolidin-1-yl)prop-2-yn-1-one |
| 117 | tert-butyl methyl((R)-1-(3-(4-(pyridin-2-yl)-3-(trifluoromethyl)phenyl)propioloyl)pyrrolidin-3-yl)carbamate |
| 118 | 1-((3R,4S)-3,4-dihydroxypyrrolidin-1-yl)-3-(2'-(benzyloxy)-3-(trifluoromethyl)-[1,1'-biphenyl]-4-yl)prop-2-yn-1-one |
| 119 | 4-(3-((3R,4S)-3,4-dihydroxypyrrolidin-1-yl)-3-oxoprop-1-yn-1-yl)-2'-(trifluoromethyl)-[1,1'-biphenyl]-2-carbaldehyde |
| 120 | methyl 4-(3-((3R,4S)-3,4-dihydroxypyrrolidin-1-yl)-3-oxoprop-1-yn-1-yl)-2'-(trifluoromethyl)-[1,1'-biphenyl]-2-carboxylate |
| 121 | (thiomorpholin-3-yl)methanol HCl |
| 122 | N-(2-aminoethyl)-2-hydroxyethane-1-sulfonamide HCl |
| 123 | thiomorpholine sulfoximine 2 HCl |

TABLE 10-continued

| PEx | Str |
|---|---|
| 124 | (3-(trifluoromethyl)biphenyl-4-yl)propynoyl-thiomorpholine with hydroxymethyl substituent |

TABLE 11

| PEx | Str |
|---|---|
| 125 | 1-(3-(4-bromo-3-(trifluoromethyl)phenyl)propynoyl)-pyrrolidine-3,4-diol |
| 126 | 1-(4-fluorophenyl)-2-(trifluoromethyl)-1H-imidazole |
| 127 | 4-bromo-1-iodo-2-(propan-2-yloxy)benzene |
| 128 | 3-(4-(pyridin-2-yl)-3-(trifluoromethyl)phenyl)propynoic acid |
| 129 | 3-(4-bromo-3-(trifluoromethyl)phenyl)propynoic acid |
| 130 | 3-(2'-(trifluoromethyl)biphenyl-4-yl)propynoic acid |
| 131 | 4-(3-(3,4-dihydroxypyrrolidin-1-yl)-3-oxoprop-1-yn-1-yl)-2'-(trifluoromethyl)biphenyl-2-carboxylic acid |
| 132 | 3-(1-(4-fluorophenyl)-2-(trifluoromethyl)-1H-imidazol-4-yl)propynoic acid |
| 133 | (4-iodo-2'-(trifluoromethyl)biphenyl-2-yl)methanol |

TABLE 11-continued

| PEx | Str |
|---|---|
| 134 | 2-iodo-6-(2-(trifluoromethyl)phenyl)benzaldehyde |
| 135 | N-(2-(methylthio)ethyl)-3-(6-phenyl-2-(trifluoromethyl)phenyl)propiolamide (biphenyl with propynamide and SMe ethyl) |
| 136 | methyl 3-(4-(pyridin-2-yl)-3-(trifluoromethyl)phenyl)propiolate |
| 137 | 1-((3R,4S)-3,4-dihydroxypyrrolidin-1-yl)-3-(2'-hydroxy-3-(trifluoromethyl)biphenyl-4-yl)prop-2-yn-1-one |
| 138 | N-(2-((tert-butyldimethylsilyl)oxy)ethyl)-N-(3-(methylsulfonamido)propyl)-3-(2'-(trifluoromethyl)biphenyl-4-yl)propiolamide |
| 139 | N-(3-((2-((tert-butyldimethylsilyl)oxy)ethyl)amino)propyl)methanesulfonamide |
| 140 | 4-bromo-N,N-dimethyl-2'-(trifluoromethyl)biphenyl-2-amine |
| 141 | methyl 4-iodo-2'-(trifluoromethyl)biphenyl-2-carboxylate |
| 142 | methyl 2-(N-(2-((tert-butoxycarbonyl)amino)ethyl)sulfamoyl)acetate |
| 143 | tert-butyl (2-(2-hydroxyethylsulfonamido)ethyl)carbamate |
| 144 | 1-(4-fluorophenyl)-4,5-diiodo-2-(trifluoromethyl)-1H-imidazole |

TABLE 12

| PEX | Str |
|---|---|
| 145 | 1-(4-fluorophenyl)-4-iodo-2-(trifluoromethyl)-1H-imidazole |

TABLE 13
| Ex | Str |
|----|-----|
| 1 | 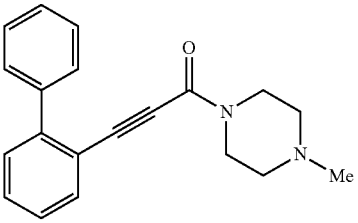 [SMILES: CN1CCN(C(=O)C#Cc2ccccc2-c2ccccc2)CC1] |
| 2 | 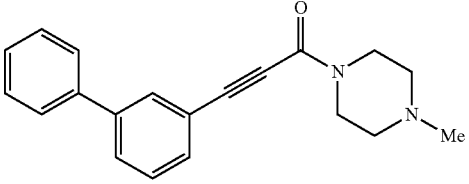 [SMILES: CN1CCN(C(=O)C#Cc2cccc(-c3ccccc3)c2)CC1] |
| 3 | 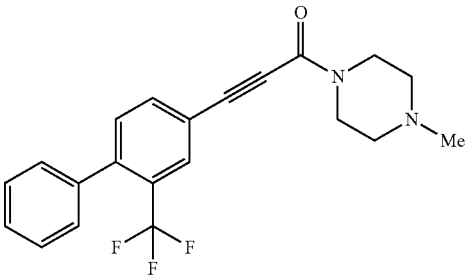 [SMILES: CN1CCN(C(=O)C#Cc2ccc(-c3ccccc3)c(C(F)(F)F)c2)CC1] |
| 4 | 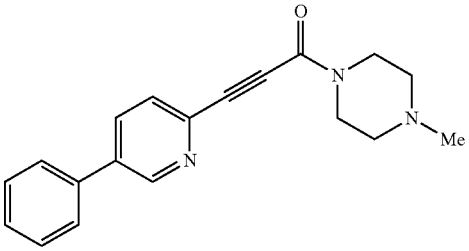 [SMILES: CN1CCN(C(=O)C#Cc2ccc(-c3ccccc3)cn2)CC1] |
| 5 | 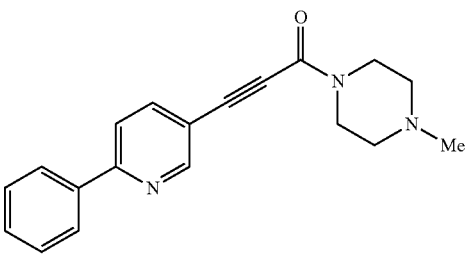 [SMILES: CN1CCN(C(=O)C#Cc2ccc(-c3ccccc3)nc2)CC1] |
| 6 | 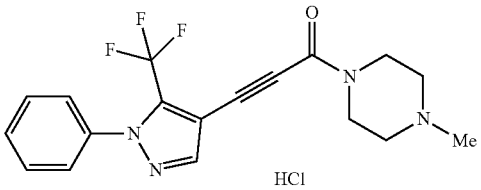 [SMILES: CN1CCN(C(=O)C#Cc2cnn(-c3ccccc3)c2C(F)(F)F)CC1 ; Cl] HCl |
| 7 | 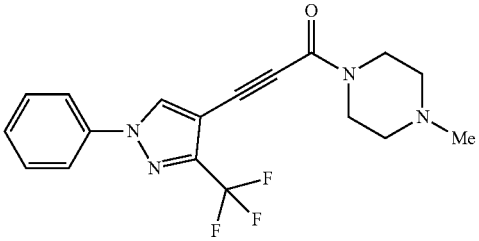 [SMILES: CN1CCN(C(=O)C#Cc2cn(-c3ccccc3)nc2C(F)(F)F)CC1] |
| 8 | 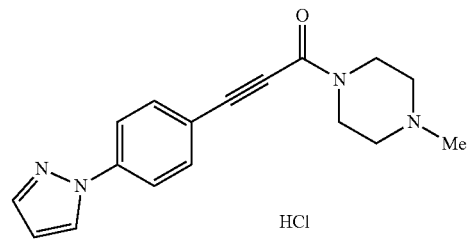 [SMILES: CN1CCN(C(=O)C#Cc2ccc(-n3cccn3)cc2)CC1 ; Cl] HCl |
| 9 | 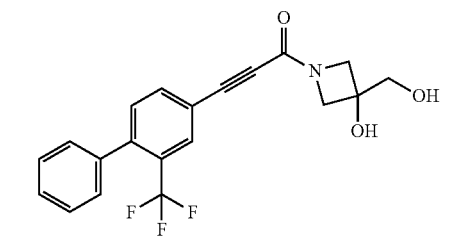 [SMILES: O=C(C#Cc1ccc(-c2ccccc2)c(C(F)(F)F)c1)N1CC(O)(CO)C1] |
| 10 | 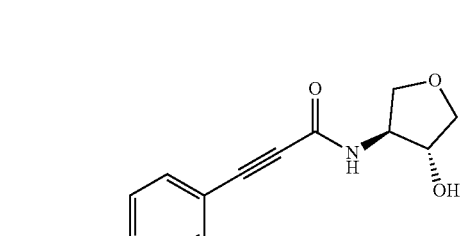 |
| 11 | 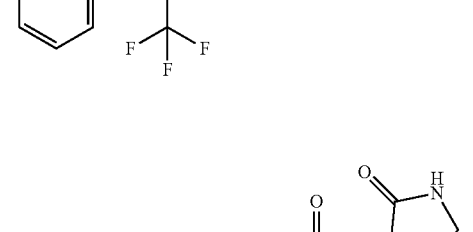 |

TABLE 13-continued
| Ex | Str |
|---|---|
| 12 | 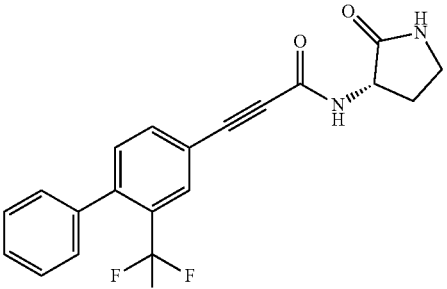 |
| 13 | 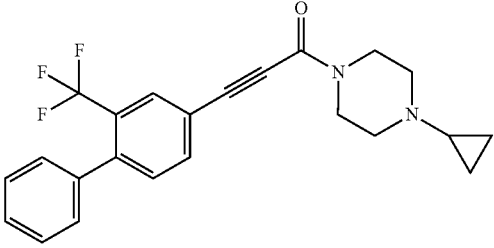 [SMILES: O=C(C#Cc1ccc(-c2ccccc2)c(C(F)(F)F)c1)N1CCN(C2CC2)CC1] |
| 14 | 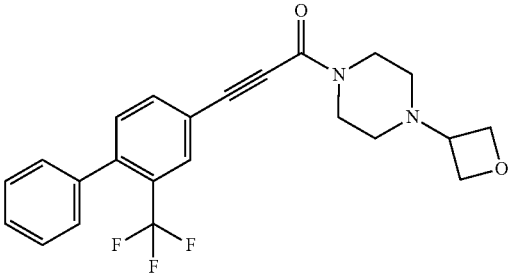 [SMILES: O=C(C#Cc1ccc(-c2ccccc2)c(C(F)(F)F)c1)N1CCN(C2COC2)CC1] |
| 15 | 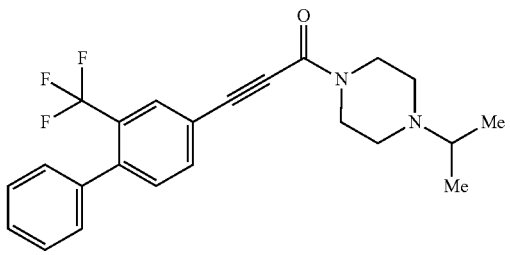 [SMILES: CC(C)N1CCN(C(=O)C#Cc2ccc(-c3ccccc3)c(C(F)(F)F)c2)CC1] |
| 16 | 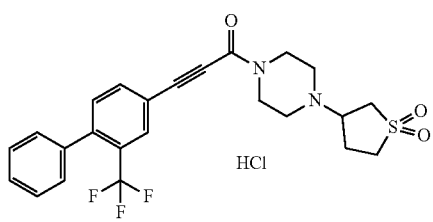 [SMILES: O=C(C#Cc1ccc(-c2ccccc2)c(C(F)(F)F)c1)N1CCN(C2CCS(=O)(=O)C2)CC1 ; Cl] |
| 17 | 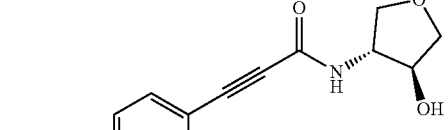 |
| 18 | 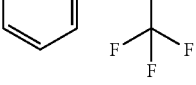 |
| 19 | 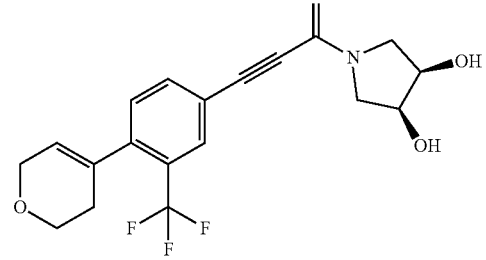 |
| 20 | 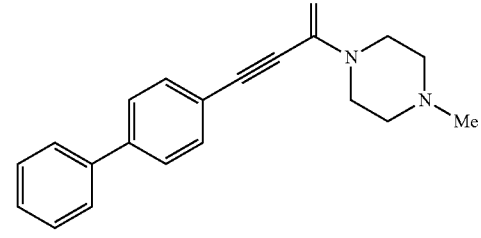 |
TABLE 14
| Ex | Str |
|---|---|
| 21 | 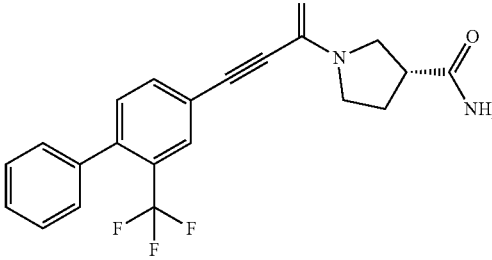 |

TABLE 14-continued

| Ex | Str |
|----|-----|
| 22 | *thiomorpholine amide of 4-phenyl-3-(trifluoromethyl)phenyl propiolic acid* |
| 23 | *(S)-prolinamide of 4-phenyl-3-(trifluoromethyl)phenyl propiolic acid* |
| 24 | *(R)-prolinamide of 4-phenyl-3-(trifluoromethyl)phenyl propiolic acid* |
| 25 | *3-hydroxy prolinamide of 4-phenyl-3-(trifluoromethyl)phenyl propiolic acid* |
| 26 | *4-hydroxy-4-(hydroxymethyl)piperidine amide of 4-phenyl-3-(trifluoromethyl)phenyl propiolic acid* |
| 27 | *(R)-3-carboxamide pyrrolidine amide of 4-phenyl-3-(trifluoromethyl)phenyl propiolic acid* |
| 28 | *4-hydroxy prolinamide of 4-phenyl-3-(trifluoromethyl)phenyl propiolic acid* |
| 29 | *N-methyl glycinamide of 4-phenyl-3-(trifluoromethyl)phenyl propiolic acid* |
| 30 | *taurinamide of 4-phenyl-3-(trifluoromethyl)phenyl propiolic acid* |
| 31 | *N-(2-methanesulfonamidoethyl)amide of 4-phenyl-3-(trifluoromethyl)phenyl propiolic acid* |

TABLE 14-continued
| Ex | Str |
|---|---|
| 32 | 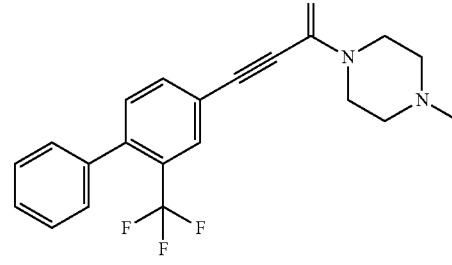 |
| 33 | |
| 34 | |
| 35 | |
| 36 | |
TABLE 14-continued
| Ex | Str |
|---|---|
| 37 | 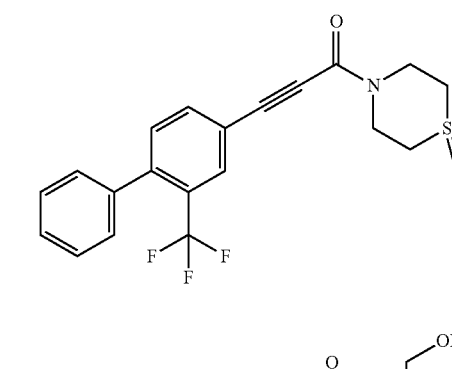 |
| 38 | |
| 39 | |
| 40 | |
TABLE 15
| Ex | Str |
|---|---|
| 41 | |

TABLE 15-continued
| Ex | Str |
|---|---|
| 42 | 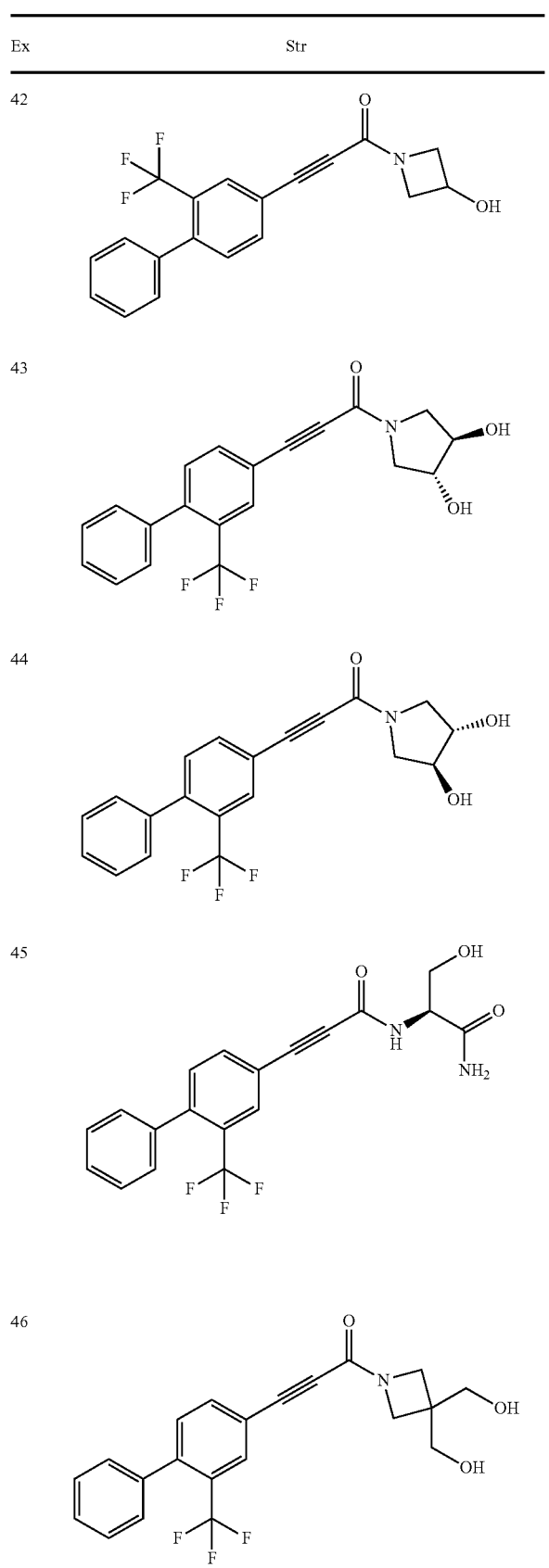 |
| 43 | |
| 44 | |
| 45 | |
| 46 | |
TABLE 15-continued
| Ex | Str |
|---|---|
| 47 | 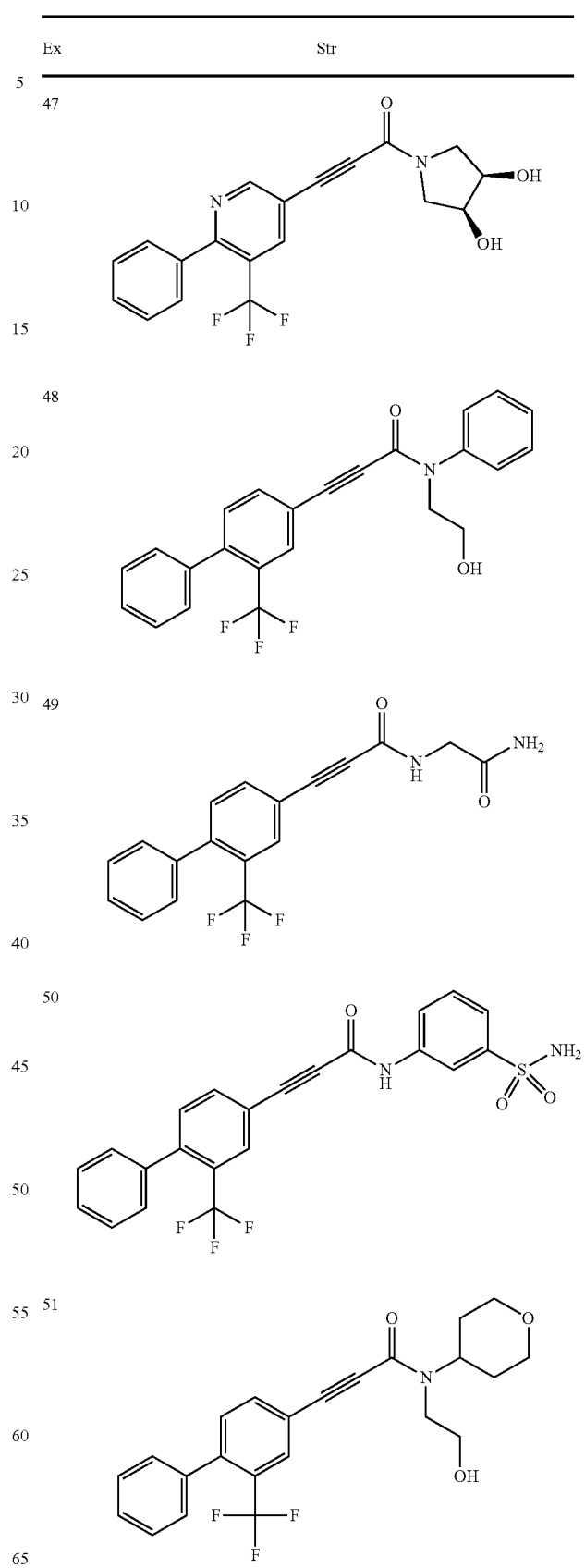 |
| 48 | |
| 49 | |
| 50 | |
| 51 | |

TABLE 15-continued

| Ex | Str |
|---|---|
| 52 | (structure) |
| 53 | (structure) |
| 54 | (structure) |
| 55 | (structure) |
| 56 | (structure) |
| 57 | (structure) |
| 58 | (structure) |
| 59 | (structure) |
| 60 | (structure) |

TABLE 16

| Ex | Str |
|---|---|
| 61 | (structure) |

TABLE 16-continued

| Ex | Str |
|---|---|
| 62 | |
| 63 | |
| 64 | |
| 65 | |
| 66 | |
| 67 | |
| 68 | |
| 69 | |
| 70 | |
| 71 | |
| 72 | |

TABLE 16-continued
| Ex | Str |
|---|---|
| 73 | |
| 74 | |
| 75 | |
| 76 | |
| 77 | |
TABLE 16-continued
| Ex | Str |
|---|---|
| 78 | |
| 79 | |
| 80 | |
TABLE 17
| Ex | Str |
|---|---|
| 81 | |
| 82 | |
| 83 | |
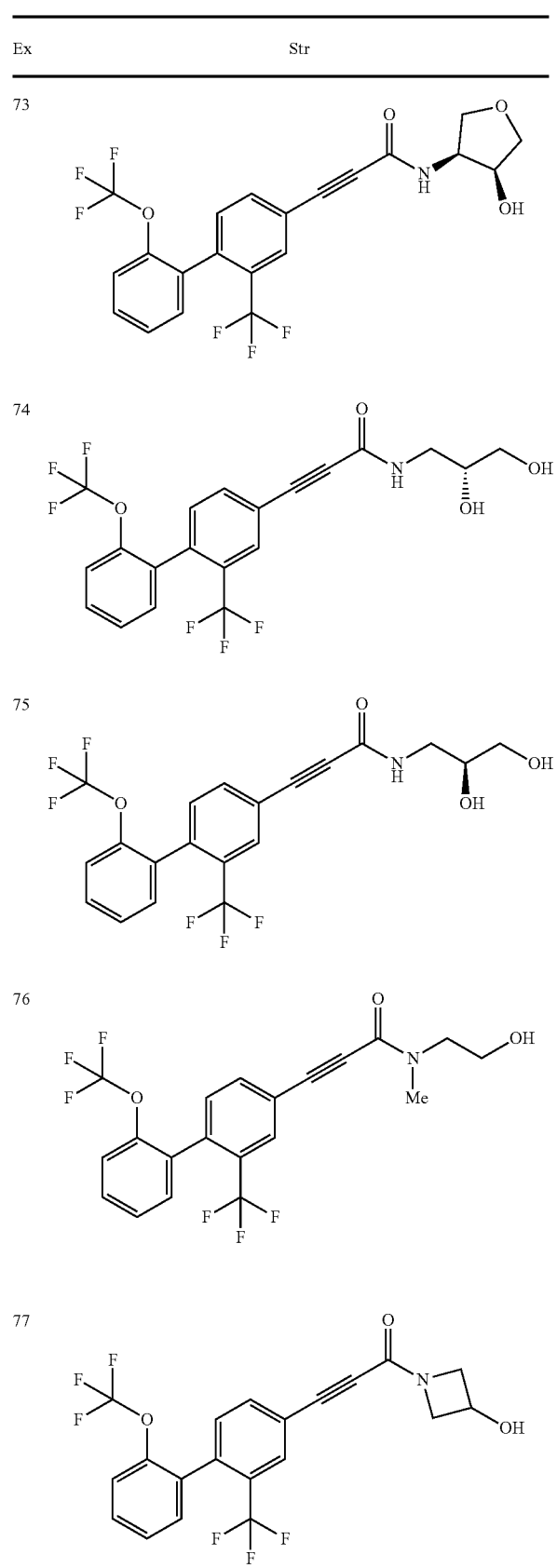
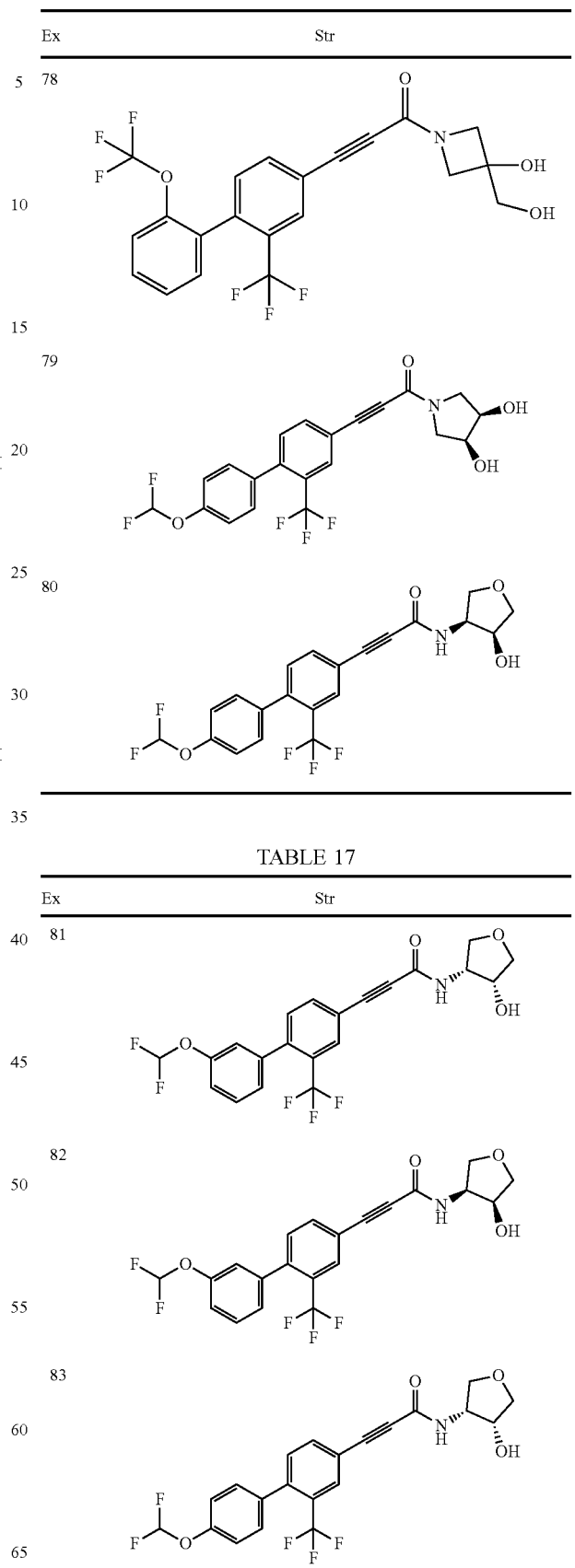

TABLE 17-continued
| Ex | Str |
|---|---|
| 84 |  |
| 85 | 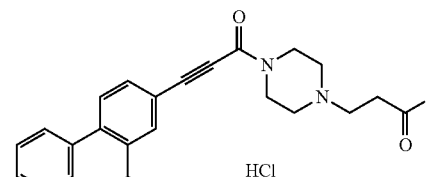 |
| 86 | 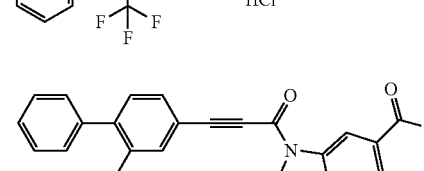 |
| 87 | 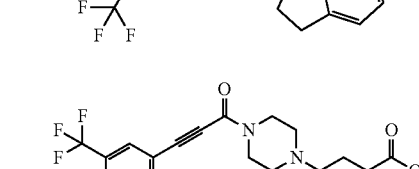 |
| 88 | 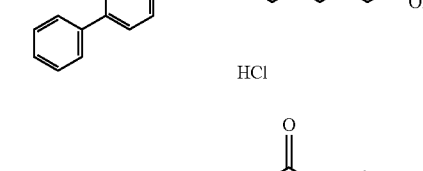 |
| 89 | 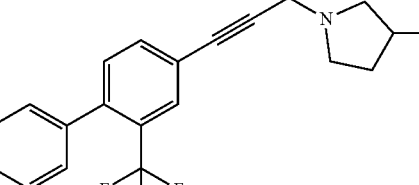 |
| 90 | |
| 91 | |
| 92 | |
| 93 | |
| 94 | |
| 95 | |
| 96 | |

TABLE 17-continued
| Ex | Str |
|---|---|
| 97 | 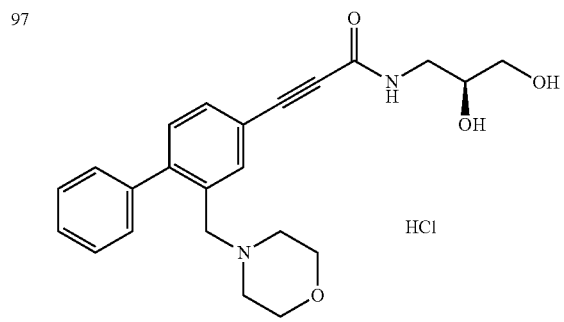 HCl |
| 98 | 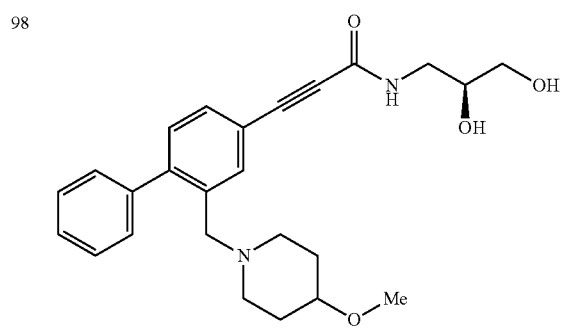 |
| 99 | 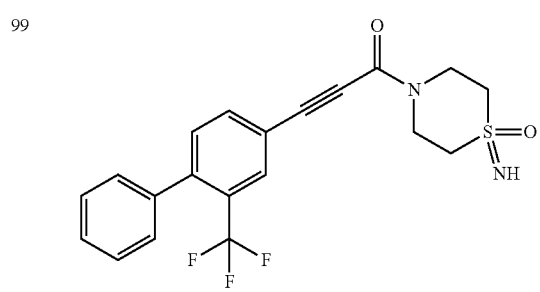 |
| 100 | 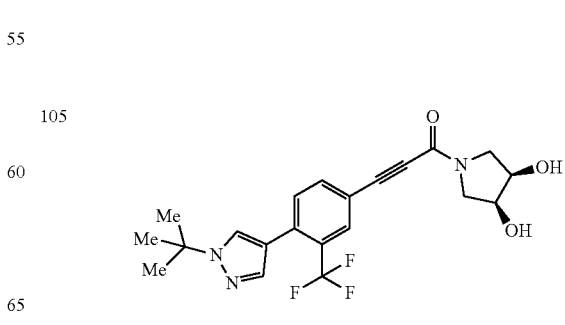 |
TABLE 18
| Ex | Str |
|---|---|
| 101 | 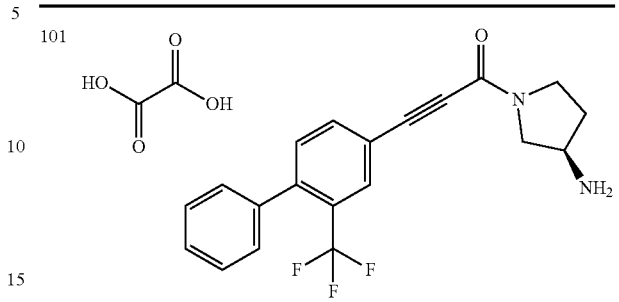 |
| 102 | 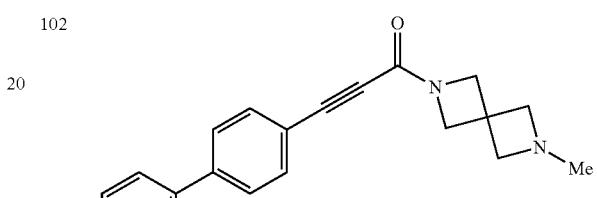 |
| 103 | 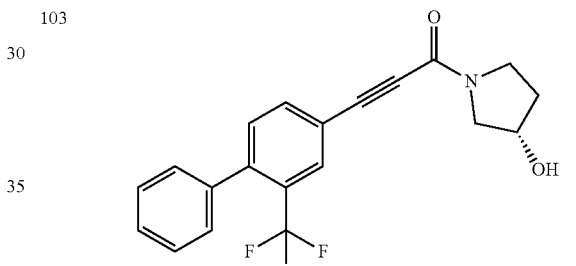 |
| 104 | 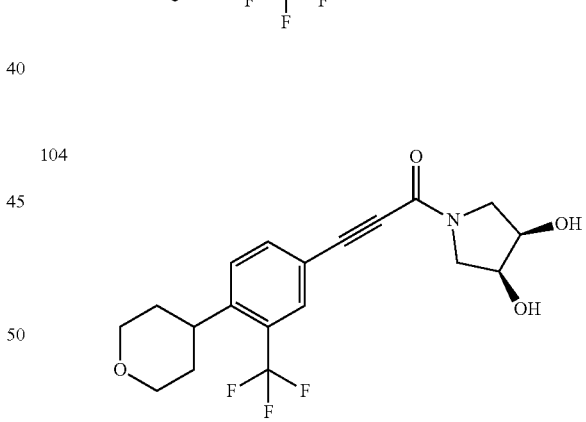 |
| 105 | 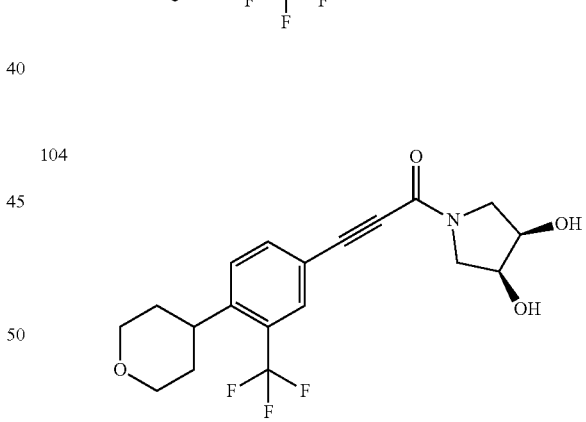 |

TABLE 18-continued

| Ex | Str |
|---|---|
| 106 | |
| 107 | |
| 108 | |

TABLE 19

| Ex | Str |
|---|---|
| 109 | |
| 110 | |
| 111 | |
| 112 | |
| 113 | |
| 114 | |

TABLE 19-continued

| Ex | Str |
|---|---|
| 115 | (structure) |
| 116 | (structure) |
| 117 | (structure) |
| 118 | (structure) |
| 119 | (structure) |
| 120 | (structure) |
| 121 | (structure) |
| 122 | (structure) |
| 123 | (structure) |
| 124 | (structure) |

TABLE 19-continued

| Ex | Str |
|---|---|
| 125 | |
| 126 | |
| 127 | |
| 128 | |

TABLE 20

| Ex | Str |
|---|---|
| 129 | |

TABLE 20-continued

| Ex | Str |
|---|---|
| 130 | |
| 131 | |
| 132 | |
| 133 | |
| 134 | |

TABLE 20-continued

| Ex | Str |
|---|---|
| 135 | 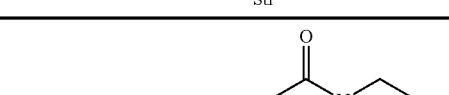 |
| 136 | 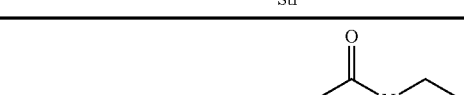 |

TABLE 21

| PEx | PSyn | DAT |
|---|---|---|
| 1 | — | $^1$H NMR (DMSO-$d_6$, 500 MHz) δ 7.90 (d, 1H, J = 8.3 Hz), 7.84 (d, 1H, J = 2.0 Hz), 7.66 (dd, 1H, J = 2.0, 8.3 Hz), 0.25 (s, 9H) |
| 2 | 1 | $^1$H NMR (DMSO-$d_6$, 400 MHz) δ = 9.23 (s, 1H), 8.22 (s, 1H), 8.10 (d, J = 8.4 Hz, 2H), 7.93 (d, J = 8.8 Hz, 2H), 3.68-3.83 (m, 2H), 3.48-3.58 (m, 2H), 3.40-3.47 (m, 2H), 3.33-3.38 (m, 2H), 1.42 (s, 9H) |
| 3 | 1 | ESI+; 309.1 |
| 4 | 1 | ESI+; 309.1 |
| 5 | 1 | $^1$H NMR (DMSO-$d_6$, 500 MHz) δ 8.12 (d, 1H, J = 2.0 Hz), 8.02 (d, 1H, J = 8.3 Hz), 7.88 (dd, 1H, J = 8.3, 2.0 Hz), 3.81 (s, 3H) |
| 6 | — | $^1$H NMR (DMSO-$d_6$, 400 MHz) δ 9.86 (s, 1H), 8.05 (d, 1H, J = 1.6 Hz), 7.97 (dd, 1H, J = 1.6, 8.0 Hz), 7.63 (d, 1H, J = 8.0 Hz), 7.46-7.57 (m, 5H) |
| 7 | — | CI+; 327.1 |
| 8 | 1 | $^1$H NMR (CDCl$_3$, 400 MHz): δ 7.70 (s, 1H), 7.57 (d, 1H, J = 8.2 Hz), 7.38 (d, 1H, J = 8.1 Hz), 4.05 (dd, 2H, J = 4.1, 11.4 Hz), 3.46-3.54 (m, 2H), 3.15 (t, 1H, J = 11.8 Hz), 1.81 (dq, 2H, J = 4.4, 12.6 Hz), 1.56-1.70 (m, 2H), 0.23 (s, 9H) |
| 9 | 1 | ESI+; 365.2 |
| 10 | — | ESI−; 317.0 |
| 11 | — | CI+; 320.1 |
| 12 | 10 | CI+; 371.0 |
| 13 | 10 | $^1$H NMR (DMSO-$d_6$, 500 MHz) δ 8.13 (d, 1H, J = 1.5 Hz), 8.01 (dd, 1H, J = 1.5, 7.9 Hz), 7.54 (d, 1H, J = 8.0 Hz), 7.39-7.43 (m, 2H), 7.34 (t, 1H, J = 74 Hz), 7.26-7.30 (m, 2H), 3.82 (s, 3H) |
| 14 | 10 | EI+; 402.1 |
| 15 | 10 | ESI+; 389.1 |
| 16 | 10 | CI+; 353.0 |
| 17 | 10 | CI+; 388.1 |
| 18 | 10 | $^1$H NMR (CDCl$_3$, 400 MHz) δ 7.81 (s, 1H), 7.62 (d, 1H, J = 7.6 Hz), 7.17-7.23 (m, 1H), 5.60 (br s, 1H), 4.20 (m, 2H), 3.84 (t, 2H, J = 5.6 Hz), 3.79 (s, 3H), 2.27 (br s, 2H) |
| 19 | 10 | ESI−; 243.0 |
| 20 | 10 | ESI+; 285.1 |
| 21 | — | EI+; 246.1 |
| 22 | — | CI+; 248.0 |
| 23 | — | ESI+; 237.1 |

TABLE 22

| PEx | PSyn | DAT |
|---|---|---|
| 24 | 21 | ESI+; 237.0 |
| 25 | 21 | EI+; 330.1 |
| 26 | 21 | EI+; 280.1 |
| 27 | 21 | CI+; 316.0 |
| 28 | 21 | CI+; 255.0 |
| 29 | 21 | ESI+; 296.3 [M + H + CH$_3$CN]+ |
| 30 | 21 | $^1$H NMR (CDCl$_3$, 400 MHz): δ 7.81 (s, 1H), 7.60 (dd, 3H, J = 9.2, 15.7 Hz), 7.37 (d, 1H, J = 8.0 Hz), 3.29 (s, 1H), 1.59 (s, 9H) |
| 31 | — | ESI−; 245.1 [M − CO$_2$H]−<br>$^1$H NMR (DMSO-$d_6$, 500 MHz) δ 14.00 (br s, 1H), 8.07 (d, 1H, J = 1.7 Hz), 7.96 (dd, 1H, J = 1.3, 7.9 Hz), 7.44-7.53 (m, 4H), 7.32-7.36 (m, 2H) |
| 32 | — | ESI+; 292.1 |

TABLE 22-continued

| PEx | PSyn | DAT |
|---|---|---|
| 33 | 31 | ESI+; 223.8 |
| 34 | 31 | ESI+; 223.9 |
| 35 | 31 | ESI+; 281.0 |
| 36 | 31 | ESI+; 281.0 |
| 37 | 31 | ESI−; 329.1 [M − CO$_2$H]− <br> $^1$H NMR (DMSO-d$_6$, 500 MHz) δ 14.00 (br s, 1H), 8.12 (d, 1H, J = 1.5 Hz), 8.00 (dd, 1H, J = 1.3, 7.9 Hz), 7.60-7.64 (m, 1H), 7.47-7.53 (m, 3H), 7.42-7.46 (m, 1H) |
| 38 | 31 | ESI−; 279.1 [M − CO$_2$H]− <br> $^1$H NMR (DMSO-d$_6$, 500 MHz) δ 14.05 (br s, 1H), 8.08 (d, 1H, J = 1.5 Hz), 7.98 (dd, 1H, J = 1.4, 8.0 Hz), 7.51-7.56 (m, 3H), 7.35-7.40 (m, 2H) |
| 39 | 31 | ESI+; 360.3 |
| 40 | 31 | ESI+; 299.1 |
| 41 | 31 | $^1$H NMR (CDCl$_3$, 400 MHz) δ 7.50 (br s, 2H), 7.11 (br s, 1H), 3.88 (br s, 2H), 3.33 (br s, 2H), 2.88 (s, 1H), 1.51 (br s, 4H) |
| 42 | 31 | $^1$H NMR (CDCl$_3$, 400 MHz) δ 7.74 (br s, 2H), 7.50 (br s, 3H), 1.53 (s, 9H) |
| 43 | — | ESI+; 308.8 |
| 44 | 43 | ESI+; 403.1 [M + H − tBu]+ |
| 45 | — | ESI+; 348.9 |

TABLE 23

| PEx | PSyn | DAT |
|---|---|---|
| 46 | 45 | $^1$H NMR (DMSO-d$_6$, 400 MHz) δ 8.98 (br s, 2H), 8.14 (d, 1H, J = 1.2 Hz), 7.99 (dd, 1H, J = 1.2, 8.0 Hz), 7.53 (d, 1H, J = 8.0 Hz), 7.44-7.50 (m, 3H), 7.30-7.37 (m, 2H), 4.03 (t, 2H, J = 5.2 Hz), 3.75 (t, 2H, J = 5.2 Hz), 3.25 (br s, 2H), 3.16 (br s, 2H) |
| 47 | — | ESI+; 424.2 |
| 48 | — | ESI+; 346.1 |
| 49 | 48 | $^1$H NMR (CDCl$_3$, 400 MHz) δ 9.88 (s, 1H), 7.68 (d, 1H, J = 1.6 Hz), 7.45-7.55 (m, 6H), 7.35-7.43 (m, 4H), 7.29-7.34 (m, 2H), 3.85-4.07 (m, 3H), 3.71 (br s, 2H), 3.00 (br s, 1H), 2.79 (s, 1H) |
| 50 | — | ESI+; 339.0 |
| 51 | — | ESI+; 473.1 |
| 52 | — | ESI−; 311.1 [M − CO$_2$H]− <br> $^1$H NMR (DMSO-d$_6$, 500 MHz) δ 8.06 (d, 1H, J = 1.5 Hz), 7.96 (dd, 1H, J = 1.5, 7.9 Hz), 7.53 (t, 2H, J = 8.0 Hz), 7.30 (t, 1H, J = 73.9 Hz), 7.28 (dd, 1H, J = 2.4, 8.1 Hz), 7.22 (d, 1H, J = 7.6 Hz), 7.16-7.18 (m, 1H) |
| 53 | 52 | ESI−; 311.1 [M − CO$_2$H]− <br> $^1$H NMR (DMSO-d$_6$, 500 MHz) δ 14.14 (br s, 1H), 8.06 (d, 1H, J = 1.5 Hz), 7.96 (dd, 1H, J = 1.5, 7.9 Hz), 7.51 (d, 1H, J = 8.0 Hz), 7.38-7.43 (m, 2H), 7.34 (t, 1H, J = 73.9 Hz), 7.25-7.29 (m, 2H) |
| 54 | 52 | ESI−; 329.0 [M − CO$_2$H]− <br> $^1$H NMR (DMSO-d$_6$, 500 MHz) δ 14.01 (br s, 1H), 8.09 (d, 1H, J = 1.7 Hz), 7.98 (dd, 1H, J = 1.3, 7.9 Hz), 7.56 (d, 1H, J = 8.1 Hz), 7.46-7.51 (m, 4H) |
| 55 | 52 | $^1$H NMR (CDCl$_3$, 400 MHz) δ 7.84 (s, 1H), 7.65 (dd, 1H, J = 1.2, 8.0 Hz), 7.23 (d, 1H, J = 7.6 Hz), 5.62 (m, 1H), 4.23 (br s, 2H), 3.81-3.89 (m, 2H), 2.29 (br s, 2H) |
| 56 | — | $^1$H NMR (CDCl$_3$, 400 MHz) δ 7.94 (d, 1H, J = 1.6 Hz), 7.69 (dd, 1H, J = 1.2, 8.0 Hz), 7.36-7.47 (m, 3H), 7.29-7.35 (m, 2H), 7.01 (d, 1H, J = 8.0 Hz), 4.57 (s, 2H) |
| 57 | — | $^1$H NMR (CDCl$_3$, 400 MHz) δ 9.87 (s, 1H), 8.35 (d, 1H, J = 2.0 Hz), 7.96 (dd, 1H, J = 2.0, 8.0 Hz), 7.44-7.54 (m, 3H), 7.33-7.40 (m, 2H), 7.21 (d, 1H, J = 8.0 Hz) |
| 58 | — | ESI+; 324.1 |
| 59 | — | ESI+; 402.3 |
| 60 | — | ESI−; 245.0 |
| 61 | — | ESI+; 379.4 |

TABLE 24

| PEx | PSyn | DAT |
|---|---|---|
| 62 | 61 | ESI+; 417.1 |
| 63 | — | CI+; 278.0 |
| 64 | 6 | ESI+; 213.0 |
| 65 | 6 | $^1$H NMR (DMSO-$d_6$, 400 MHz) δ 8.25 (s, 1H), 7.97 (d, 1H, J = 8.4 Hz), 7.84 (dd, J = 8.4, 1.6 Hz, 1H) |
| 66 | 6 | $^1$H NMR (DMSO-$d_6$, 400 MHz) δ 10.78 (s, 1H), 7.57 (d, 1H, J = 8.4 Hz), 7.08 (d, 1H, J = 2.0 Hz), 6.97 (dd, 1H, J = 8.0, 2.0 Hz) |
| 67 | 1 | $^1$H NMR (DMSO-$d_6$, 400 MHz) δ 7.81 (s, 1H), 7.74 (d, 1H, J = 8.0 Hz), 7.22-7.34 (m, 5H), 7.12-7.20 (m, 4H), 7.00-7.05 (m, 1H), 5.02-5.11 (m, 2H), 0.26 (s, 9H) |
| 68 | 1 | $^1$H NMR (CDCl$_3$, 400 MHz) δ 7.32-7.51 (m, 8H), 6.34 (t, 1H, J = 74.0 Hz), 0.28 (s, 9H) |
| 69 | 1 | $^1$H NMR (DMSO-$d_6$, 400 MHz) δ 7.85-7.89 (m, 1H), 7.73-7.79 (m, 1H), 7.64-7.71 (m, 2H), 7.49 (dd, 1H, J = 7.6, 1.2 Hz), 7.36-7.42 (m, 1H), 7.29-7.35 (m, 1H), 0.26 (s, 9H) |
| 70 | 6 | $^1$H NMR (DMSO-$d_6$, 400 MHz) δ 9.67 (s, 1H), 8.16 (d, J = 1.6 Hz, 1H), 7.96 (dd, 1H, J = 7.6, 1.6 Hz), 7.89 (d, 1H, J = 7.6 Hz), 7.67-7.79 (m, 2H), 7.44-7.50 (m, 2H) |
| 71 | 1 | ESI+; 361.9 |
| 72 | 1 | $^1$H NMR (DMSO-$d_6$, 400 MHz) δ 7.84 (d, 1H, J = 7.6 Hz), 7.67-7.76 (m, 1H), 7.59-7.67 (m, 1H), 7.37-7.47 (m, 1H), 7.31 (d, 2H, J = 7.6 Hz), 7.09 (d, 1H, J = 8.0 Hz), 1.94 (s, 3H), 0.23 (s, 9H) |
| 73 | 6 | $^1$H NMR (DMSO-$d_6$, 400 MHz) δ 8.13 (d, 1H, J = 1.6 Hz), 7.87 (dd, 1H, J = 8.0, 1.6 Hz), 7.67-7.71 (m, 2H), 7.39 (d, 1H, J = 7.6 Hz), 7.27-7.34 (m, 2H), 3.55 (s, 3H) |
| 74 | 1 | $^1$H NMR (CDCl$_3$, 400 MHz) δ 7.49 (s, 1H), 7.35-7.38 (m, 2H), 7.20-7.26 (m, 2H), 4.29 (q, 2H, J = 7.2 Hz), 1.34 (t, 3H, J = 7.2 Hz) |
| 75 | 1 | ESI+; 320.9 |
| 76 | 1 | $^1$H NMR (DMSO-$d_6$, 400 MHz) δ 9.10 (dd, 1H, J = 4.0, 1.6 Hz), 8.60 (dd, 1H, J = 8.4, 1.2 Hz), 7.94 (d, 1H, J = 8.4 Hz), 7.78-7.83 (m, 1H), 7.78 (d, 1H, J = 8.0 Hz), 0.32 (s, 9H) |
| 77 | 1 | $^1$H NMR (CDCl$_3$, 400 MHz) δ 7.83 (d, 1H, J = 7.6 Hz), 7.66-7.73 (m, 1H), 7.55-7.65 (m, 4H), 0.33 (s, 9H) |

TABLE 25

| PEx | PSyn | DAT |
|---|---|---|
| 78 | 1 | $^1$H NMR (DMSO-$d_6$, 400 MHz) δ 7.78 (d, 1H, J = 8.0 Hz), 7.63-7.71 (m, 1H), 7.54-7.61 (m, 1H), 7.27 (d, 1H, J = 7.6 Hz), 7.10 (s, 1H), 7.02-7.08 (m, 2H), 4.53-4.68 (m, 1H), 1.06 (d, 6H, J = 6.0 Hz), 0.25 (s, 9H) |
| 79 | 1 | ESI+; 355.0 |
| 80 | 10 | $^1$H NMR (DMSO-$d_6$, 400 MHz) δ 7.98 (d, 1H, J = 1.6 Hz), 7.89 (dd, 1H, J = 8.0, 1.6 Hz), 7.36-7.42 (m, 1H), 7.08-7.35 (m, 8H), 6.95-7.05 (m, 1H), 4.98-5.17 (m, 2H) |
| 81 | 10 | $^1$H NMR (CDCl$_3$, 400 MHz) δ 7.29-7.47 (m, 8H), 6.33 (t, 1H, J = 73.6 Hz) |
| 82 | 10 | $^1$H NMR (DMSO-$d_6$, 400 MHz) δ 7.84-7.91 (m, 2H), 7.73-7.80 (m, 1H), 7.66-7.72 (m, 1H), 7.64 (dd, 1H, J = 8.2, 2.0 Hz), 7.39 (d, 1H, J = 7.6 Hz), 7.30 (d, 1H, J = 8.4 Hz) |
| 83 | 10 | CI+; 305.1 |
| 84 | 10 | $^1$H NMR (DMSO-$d_6$, 400 MHz) δ 7.70 (d, 1H, J = 7.6 Hz), 7.59 (t, 1H, J = 7.6 Hz), 7.49 (t, 1H, J = 7.6 Hz), 7.16-7.22 (m, 2H), 6.88 (d, 1H, J = 8.0 Hz), 6.77 (dd, 1H, J = 8.0, 2.4 Hz), 5.50 (br s, 2H), 3.47 (s, 3H) |
| 85 | 10 | $^1$H NMR (DMSO-$d_6$, 400 MHz) δ 7.80-7.88 (m, 1H), 7.68-7.76 (m, 1H), 7.58-7.65 (m, 1H), 7.32 (d, 1H, J = 7.6 Hz), 6.92 (d, 1H, J = 2.0 Hz), 6.68-6.80 (m, 2H), 4.85 (br s, 2H) |
| 86 | 10 | $^1$H NMR (CDCl$_3$, 400 MHz) δ 7.66 (d, 1H, J = 8.0 Hz), 7.48 (t, 1H, J = 7.3 Hz), 7.39 (t, 1H, J = 7.5 Hz), 7.14-7.20 (m, 1H), 7.06 (dd, 1H, J = 8.0, 1.8 Hz), 7.01 (d, 1H, J = 1.5 Hz), 6.94 (d, 1H, J = 8.0 Hz), 3.64 (s, 3H) |
| 87 | 10 | $^1$H NMR (CD$_3$OD, 400 MHz) δ 7.79 (d, 1H, J = 8.0 Hz), 7.60-7.69 (m, 1H), 7.52-7.60 (m, 1H), 7.43-7.47 (m, 1H), 7.32-7.38 (m, 1H), 7.25 (d, 1H, J = 7.6 Hz), 7.00 (d, 1H, J = 8.0 Hz), 1.99 (s, 3H) |
| 88 | 10 | ESI+; 302.7 |
| 89 | 10 | $^1$H NMR (CDCl$_3$, 400 MHz) δ 7.83 (d, 1H, J = 7.6 Hz), 7.71-7.76 (m, 1H), 7.61-7.71 (m, 2H), 7.55-7.60 (m, 1H), 7.50 (d, 1H, J = 8.8 Hz) |

TABLE 25-continued

| PEx | PSyn | DAT |
|---|---|---|
| 90 | 10 | $^1$H NMR (DMSO-$d_6$, 400 MHz) δ 7.78 (d, 1H, J = 8.0 Hz), 7.63-7.72 (m, 1H), 7.54-7.61 (m, 1H), 7.36-7.44 (m, 1H), 7.25-7.31 (m, 1H), 7.15 (dd, 1H, J = 8.0, 2.0 Hz), 7.05 (d, 1H, J = 8.0 Hz), 4.56-4.67 (m, 1H), 1.04-1.10 (m, 6H) |
| 91 | 10 | ESI+; 338.8 |

TABLE 26

| PEx | PSyn | DAT |
|---|---|---|
| 92 | — | $^1$H NMR (DMSO-$d_6$, 400 MHz) δ 8.86 (dd, 1H, J = 4.0, 1.2 Hz), 8.64 (dd, 1H, J = 8.4, 1.6 Hz), 7.82-7.93 (m, 2H), 7.59-7.78 (m, 4H), 7.41 (d, 1H, J = 7.6 Hz), 4.80 (s, 1H) |
| 93 | 21 | $^1$H NMR (DMSO-$d_6$, 400 MHz) δ 7.85 (s, 1H), 7.77 (d, 1H, J = 7.6 Hz), 7.24-7.32 (m, 5H), 7.17-7.21 (m, 4H), 6.97-7.02 (m, 1H), 5.00-5.14 (m, 2H), 4.41 (s, 1H) |
| 94 | 21 | $^1$H NMR (CDCl$_3$, 400 MHz) δ 7.38-7.50 (m, 8H), 6.34 (t, 1H, J = 74.0 Hz), 3.17 (s, 1H) |
| 95 | 21 | $^1$H NMR (DMSO-$d_6$, 400 MHz) δ 7.83-7.90 (m, 1H), 7.73-7.79 (m, 1H), 7.67-7.72 (m, 2H), 7.52 (dd, 1H, J = 8.0, 1.6 Hz), 7.35-7.41 (m, 2H), 4.40 (s, 1H) |
| 96 | 21 | ESI+; 289.9 |
| 97 | 1 | $^1$H NMR (CDCl$_3$, 400 MHz) δ 7.60 (d, 1H, J = 7.8 Hz), 7.42 (t, 1H, J = 7.4 Hz), 7.34 (t, 1H, J = 7.7 Hz), 7.10-7.16 (m, 1H), 6.89-7.03 (m, 3H), 3.60 (s, 3H), 0.15 (s, 9H) |
| 98 | 21 | $^1$H NMR (CDCl$_3$, 400 MHz) δ 7.75 (d, 1H, J = 7.6 Hz), 7.54-7.61 (m, 1H), 7.45-7.53 (m, 1H), 7.25-7.30 (m, 1H), 7.14-7.18 (m, 1H), 7.10-7.13 (m, 1H), 7.08 (d, 1H, J = 0.8 Hz), 3.74 (s, 3H), 3.12 (s, 1H) |
| 99 | 21 | $^1$H NMR (DMSO-$d_6$, 400 MHz) δ 7.85 (d, 1H, J = 7.6 Hz), 7.69-7.76 (m, 1H), 7.60-7.66 (m, 1H), 7.43 (s, 1H), 7.29-7.37 (m, 2H), 7.11 (d, 1H, J = 7.8 Hz), 4.21 (s, 1H), 1.95 (s, 3H) |
| 100 | 21 | ESI+; 248.8 |
| 101 | 23 | $^1$H NMR (CDCl$_3$, 400 MHz) δ 7.84 (d, 1H, J = 7.6 Hz), 7.59-7.74 (m, 5H), 3.49 (s, 1H) |
| 102 | 21 | ESI+; 304.8 |
| 103 | 21 | ESI+; 282.9 |
| 104 | 31 | $^1$H NMR (DMSO-$d_6$, 400 MHz) δ 7.95-8.06 (m, 1H), 7.89 (d, 1H, J = 8.0 Hz), 7.08-7.47 (m, 9H), 6.98-7.06 (m, 1H), 4.98-5.15 (m, 2H) |
| 105 | 31 | $^1$H NMR (DMSO-$d_6$, 400 MHz) δ 7.33-7.55 (m, 8H), 7.27 (t, 1H, J = 74.0 Hz) |
| 106 | 31 | $^1$H NMR (DMSO-$d_6$, 400 MHz) δ 7.82-8.05 (m, 2H), 7.74-7.81 (m, 1H), 7.63-7.74 (m, 2H), 7.41-7.63 (m, 2H) |
| 107 | 31 | ESI+; 333.9 |
| 108 | 31 | $^1$H NMR (DMSO-$d_6$, 400 MHz) δ 7.79 (d, 1H, J = 7.8 Hz), 7.63-7.72 (m, 1H), 7.55-7.62 (m, 1H), 7.32 (d, 1H, J = 7.5 Hz), 7.01-7.18 (m, 3H), 3.68 (s, 3H) |

TABLE 27

| PEx | PSyn | DAT |
|---|---|---|
| 109 | 31 | $^1$H NMR (DMSO-$d_6$, 400 MHz) δ 7.82-7.87 (m, 1H), 7.69-7.76 (m 1H), 7.64 (t, 1H, J = 7.6 Hz), 7.49 (dd, 1H, J = 7.6, 1.2 Hz), 7.29-7.36 (m, 2H), 7.19 (d, 1H, J = 8.0 Hz), 1.97 (s, 3H) |
| 110 | 31 | ESI+; 292.8 |
| 111 | 31 | ESI+; 342.0 |
| 112 | 31 | ESI+; 292.9 |
| 113 | 31 | ESI−; 695.3 [2M − H]− |
| 114 | 31 | ESI+; 327.1 |
| 115 | 43 | ESI+; 334.8 |
| 116 | 43 | $^1$H NMR (DMSO-$d_6$, 400 MHz) δ 10.75 (s, 1H), 7.58 (d, 1H, J = 8.0 Hz), 7.09 (d, 1H, J = 2.0 Hz), 6.98 (dd, 1H, J = 8.0, 1.6 Hz), 5.06 (dd, 2H, J = 10.5, 4.8 Hz), 4.02-4.12 (m, 2H), 3.73-3.78 (m, 1H), 3.42-3.53 (m, 2H), 3.15-3.25 (m, 1H) |
| 117 | 43 | ESI+; 474.2 |
| 118 | 43 | ESI+; 482.0 |

TABLE 27-continued

| PEx | PSyn | DAT |
|---|---|---|
| 119 | 43 | $^1$H NMR (DMSO-$d_6$, 400 MHz) δ 9.67 (s, 1H), 8.16 (d, 1H, J = 1.6 Hz), 7.97 (dd, 1H, J = 8.0, 1.6 Hz), 7.89 (d, 1H, J = 7.6 Hz), 7.66-7.80 (m, 2H), 7.47 (t, 2H, J = 7.6 Hz), 5.09 (dd, 2H, J = 10.8, 4.8 Hz), 4.06-4.15 (m, 2H), 3.82-3.89 (m, 1H), 3.57 (dd, 1H, J = 10.8, 4.8 Hz), 3.51 (dd, 1H, J = 12.4, 5.6 Hz), 3.21-3.28 (m, 1H) |
| 120 | 43 | ESI+; 434.0 |
| 121 | 45 | ESI+; 134.1 |
| 122 | 45 | $^1$H NMR (CD$_3$OD, 400 MHz) δ 3.96 (t, 2H, J = 6.0 Hz), 3.37 (t, 2H, J = 6.0 Hz), 3.29-3.33 (m, 2H), 3.07 (t, 2H, J = 6.0 Hz) |
| 123 | 45 | ESI+; 135.1 |
| 124 | 47 | ESI+; 406.1 |
| 125 | 47 | ESI+; 378.2 |
| 126 | 50 | $^1$H NMR (CDCl$_3$, 400 MHz) δ 7.33-7.41 (m, 2H), 7.17-7.26 (m, 3H), 7.13-7.16 (m, 1H) |
| 127 | — | $^1$H NMR (DMSO-$d_6$, 400 MHz) δ 7.69 (d, 1H, J = 8.4 Hz), 7.21 (d, 1H, J = 2.0 Hz), 6.89-6.97 (m, 1H), 4.66-4.78 (m, 1H), 1.28 (d, 6H, J = 6.0 Hz) |

TABLE 28

| PEx | PSyn | DAT |
|---|---|---|
| 128 | 52 | $^1$H NMR (DMSO-$d_6$, 400 MHz) δ 8.67 (d, 1H, J = 4.4 Hz), 8.10 (s, 1H), 8.01 (d, 1H, J = 8.0 Hz), 7.94 (dt, 1H, J = 7.7, 1.7 Hz), 7.65 (d, 1H, J = 8.0 Hz), 7.55 (d, 1H, J = 7.6 Hz), 7.45-7.51 (m, 1H) |
| 129 | 52 | ESI−; 291.1 |
| 130 | 52 | ESI−; 289.2 |
| 131 | 52 | $^1$H NMR (DMSO-$d_6$, 400 MHz) δ 8.10-8.15 (m, 1H), 7.81-7.88 (m, 1H), 7.79 (d, 1H, J = 8.0 Hz), 7.51-7.71 (m, 2H), 7.36 (d, 1H, J = 8.0 Hz), 7.31 (d, 1H, J = 7.6 Hz), 4.99-5.18 (m, 2H), 4.07-4.15 (m, 2H), 3.82-3.90 (m, 1H), 3.48-3.59 (m, 2H), 3.21-3.27 (m, 1H) |
| 132 | 52 | $^1$H NMR (CDCl$_3$, 400 MHz) δ 7.54 (s, 1H), 7.35-7.41 (m, 2H), 7.20-7.27 (m, 2H) |
| 133 | 56 | $^1$H NMR (CDCl$_3$, 400 MHz) δ 7.96 (d, 1H, J = 1.6 Hz), 7.77 (d, 1H, J = 7.6 Hz), 7.66 (dd, 1H, J = 8.0, 1.6 Hz), 7.58 (t, 1H, J = 7.6 Hz), 7.52 (t, 1H, J = 7.6 Hz), 7.25 (t, 1H, J = 7.6 Hz), 6.91 (d, 1H, J = 8.0 Hz), 4.33 (d, 2H, J = 3.2 Hz) |
| 134 | 57 | $^1$H NMR (CDCl$_3$, 400 MHz) δ 9.57 (s, 1H), 8.34 (d, 1H, J = 1.2 Hz), 7.95 (dd, 1H, J = 8.0, 1.2 Hz), 7.82 (d, 1H, J = 7.2 Hz), 7.55-7.68 (m, 2H), 7.30 (d, 1H, J = 7.2 Hz), 7.09 (d, 1H, J = 8.0 Hz) |
| 135 | — | ESI+; 364.2 |
| 136 | — | $^1$H NMR (CDCl$_3$, 400 MHz) δ 8.72 (d, 1H, J = 4.8 Hz), 8.01 (s, 1H), 7.75-7.88 (m, 2H), 7.57 (d, 1H, J = 8.0 Hz), 7.44 (d, 1H, J = 8.0 Hz), 7.37 (dd, 1H, J = 6.8, 5.6 Hz), 3.89 (s, 3H) |
| 137 | — | ESI+; 392.1 |
| 138 | — | ESI+; 583.5 |
| 139 | — | ESI+; 311.4 |
| 140 | E95 | ESI+; 345.6 |
| 141 | — | $^1$H NMR (CDCl$_3$, 400 MHz) δ 8.39 (d, 1H, J = 2.0 Hz), 7.88 (dd, 1H, J = 8.0, 1.6 Hz), 7.73 (d, 1H, J = 7.6 Hz), 7.56 (t, 1H, J = 7.2 Hz), 7.50 (t, 1H, J = 7.6 Hz), 7.21 (d, 1H, J = 7.6 Hz), 7.01 (d, 1H, J = 8.0 Hz), 3.63 (s, 3H) |
| 142 | — | $^1$H NMR (CDCl$_3$, 400 MHz) δ 5.31 (br s, 1H), 4.96 (br s, 1H), 4.04 (s, 2H), 3.82 (s, 3H), 3.32 (br s, 4H), 1.46 (s, 9H) |
| 143 | — | $^1$H NMR (CDCl$_3$, 400 MHz) δ 5.11 (br s, 1H), 4.96 (br s, 1H), 4.04-4.12 (m, 2H), 3.19-3.40 (m, 6H), 2.76 (br s, 1H), 1.46 (s, 9H) |
| 144 | — | $^1$H NMR (CDCl$_3$, 400 MHz) δ 7.23-7.29 (m, 4H) |
| 145 | — | $^1$H NMR (CDCl$_3$, 400 MHz) δ 7.32-7.38 (m, 2H), 7.18-7.25 (m, 3H) |

TABLE 29

| Ex | Syn | DAT |
|---|---|---|
| 1 | — | ESI+; 304.9 |
| 2 | 1 | ESI+; 304.9 |
| 3 | 1 | ESI+; 372.9 |
| 4 | 1 | ESI+; 306.2 |
| 5 | 1 | ESI+; 305.9 |
| 6 | 1 | ESI+; 363.4 |

TABLE 29-continued

| Ex | Syn | DAT |
|---|---|---|
| 7 | 1 | ESI+; 363.2 |
| 8 | 1 | ESI+; 295.1 |
| 9 | 1 | ESI+; 376.1 |
| 10 | 1 | ESI+; 376.1 |
| 11 | 1 | ESI+; 373.0 |
| 12 | 1 | ESI+; 373.0 |
| 13 | 1 | ESI+; 399.1 |
| 14 | 1 | ESI+; 415.3 |
| 15 | 1 | ESI+; 401.1 |
| 16 | 1 | ESI+; 477.2 |
| 17 | 1 | ESI+; 376.1 |
| 18 | 1 | ESI+; 382.1 |
| 19 | 1 | ESI+; 305.1 |
| 20 | — | ESI+; 387.3<br>$^1$H NMR (CDCl$_3$, 500 MHz) δ 7.91 (dd, 1H, J = 1.6, 3.6 Hz), 7.72 (dt, 1H, J = 1.8, 8.0 Hz), 7.38-7.45 (m, 3H), 7.36 (d, 1H, J = 8.0 Hz), 7.31 (dd, 2H, J = 2.7, 6.2 Hz), 5.31-5.67 (m, 2H), 3.52-4.11 (m, 4H), 2.97-3.12 (m, 1H), 2.19-2.39 (m, 2H) |
| 21 | 20 | ESI+; 360.3 |
| 22 | 20 | ESI+; 376.2 |
| 23 | 20 | ESI+; 387.2 |
| 24 | 20 | ESI+; 387.4 |
| 25 | 20 | ESI+; 403.2 |
| 26 | 20 | ESI+; 404.3 |
| 27 | 20 | ESI+; 387.3 |
| 28 | 20 | ESI+; 403.1 |
| 29 | 20 | ESI+; 361.2 |
| 30 | 20 | ESI+; 397.2 |

TABLE 30

| Ex | Syn | DAT |
|---|---|---|
| 31 | 20 | ESI+; 411.2 |
| 32 | 20 | ESI+; 425.2 |
| 33 | — | ESI+; 376.2<br>$^1$H NMR (DMSO-d$_6$, 500 MHz) δ 8.08 (d, 1H, J = 1.5 Hz), 7.96 (dd, 1H, J = 1.4, 8.0 Hz), 7.44-7.53 (m, 4H), 7.31-7.37 (m, 2H), 5.02-5.13 (m, 2H), 4.04-4.16 (m, 2H), 3.86 (dd, 1H, J = 5.4, 11.0 Hz), 3.58 (dd, 1H, J = 5.0, 10.9 Hz), 3.50 (dd, 1H, J = 5.5, 12.7 Hz), 3.24 (dd, 1H, J = 4.5, 12.6 Hz) |
| 34 | — | ESI+; 401.4<br>$^1$H NMR (DMSO-d$_6$, 400 MHz) δ 8.09-8.10 (m, 1H), 7.97 (d, 1H, J = 7.9 Hz), 7.43-7.52 (m, 4H), 7.30-7.37 (m, 3H), 6.83 (br s, 1H), 4.27-4.40 (m, 2H), 3.20-3.40 (m, 1H), 2.82 (dt, 1H, J = 3.1, 12.5 Hz), 2.37-2.45 (m, 1H), 1.74-1.90 (m, 2H), 1.36-1.62 (m, 2H) |
| 35 | — | ESI+; 364.2<br>$^1$H NMR (DMSO-d$_6$, 400 MHz) δ 8.79 (t, 1H, J = 5.7 Hz), 8.01 (s, 1H), 7.91 (d, 1H, J = 7.9 Hz), 7.44-7.52 (m, 4H), 7.31-7.38 (m, 2H), 4.82 (d, 1H, J = 5.0 Hz), 4.57 (t, 1H, J = 5.6 Hz), 3.52-3.61 (m, 1H), 3.23-3.40 (m, 3H), 3.02-3.12 (m, 1H) |
| 36 | — | ESI+; 364.3<br>$^1$H NMR (DMSO-d$_6$, 400 MHz) δ 8.79 (t, 1H, J = 5.8 Hz), 8.01 (d, 1H, J = 1.2 Hz), 7.90 (d, 1H, J = 7.9 Hz), 7.44-7.52 (m, 4H), 7.31-7.37 (m, 2H), 4.82 (d, 1H, J = 5.5 Hz), 4.57 (t, 1H, J = 5.8 Hz), 3.52-3.61 (m, 1H), 3.23-3.39 (m, 3H), 3.00-3.13 (m, 1H) |
| 37 | 33 | ESI+; 402.5 |
| 38 | 33 | ESI+; 408.4 |
| 39 | 33 | ESI+; 364.2 |
| 40 | 33 | ESI+; 448.5 |
| 41 | 33 | ESI+; 448.1 |
| 42 | 33 | ESI+; 346.4 |
| 43 | — | ESI+; 376.2<br>$^1$H NMR (DMSO-d$_6$, 500 MHz) δ 8.08 (d, 1H, J = 1.7 Hz), 7.96 (dd, 1H, J = 1.4, 8.0 Hz), 7.44-7.52 (m, 4H), 7.32-7.37 (m, 2H), 5.27 (d, 2H, J = 12.1 Hz), 3.98-4.03 (m, 2H), 3.84 (dd, 1H, J = 3.8, 11.5 Hz), 3.67 (d, 1H, J = 11.5 Hz), 3.50 (dd, 1H, J = 4.1, 12.9 Hz), 3.24-3.37 (m, 1H) |

TABLE 31

| Ex | Syn | DAT |
|---|---|---|
| 44 | — | ESI+; 376.4<br>¹H NMR (DMSO-d₆, 500 MHz) δ 8.09 (d, 1H, J = 1.5 Hz), 7.96 (dd, 1H, J = 1.4, 8.0 Hz), 7.44-7.52 (m, 4H), 7.34 (dd, 2H, J = 2.0, 7.0 Hz), 5.27 (dd, 2H, J = 3.4, 13.8 Hz), 3.98-4.03 (m, 2H), 3.84 (dd, 1H, J = 3.7, 11.6 Hz), 3.67 (d, 1H, J = 11.5 Hz), 3.49 (dd, 1H, J = 4.1, 13.0 Hz), 3.25-3.37 (m, 1H) |
| 45 | — | ESI+; 377.4<br>¹H NMR (DMSO-d₆, 500 MHz) δ 8.80 (d, 1H, J = 8.1 Hz), 8.05 (d, 1H, J = 1.5 Hz), 7.93 (dd, 1H, J = 1.4, 8.0 Hz), 7.42-7.54 (m, 5H), 7.32-7.38 (m, 2H), 7.14 (s, 1H), 4.97 (t, 1H, J = 5.6 Hz), 4.30-4.36 (m, 1H), 3.58-3.68 (m, 2H) |
| 46 | — | ESI+; 390.4<br>¹H NMR (DMSO-d₆, 500 MHz) δ 8.05 (d, 1H, J = 1.5 Hz), 7.93 (dd, 1H, J = 1.4, 8.0 Hz), 7.44-7.52 (m, 4H), 7.31-7.36 (m, 2H), 4.93 (br s, 2H), 4.01 (s, 2H), 3.70 (s, 2H), 3.51 (s, 4H) |
| 47 | — | ESI+; 377.4<br>¹H NMR (DMSO-d₆, 500 MHz) δ 9.13 (d, 1H, J = 1.7 Hz), 8.63 (d, 1H, J = 1.9 Hz), 7.47-7.55 (m, 5H), 5.07 (dd, 2H, J = 4.9, 7.8 Hz), 4.07-4.15 (m, 2H), 3.87 (dd, 1H, J = 5.4, 11.0 Hz), 3.56-3.67 (m, 1H), 3.52 (dd, 1H, J = 5.4, 12.6 Hz), 3.25 (dd, 1H, J = 4.6, 12.6 Hz) |
| 48 | 43 | ESI+; 410.5 |
| 49 | 43 | ESI+; 347.3 |
| 50 | 43 | ESI+; 445.4 |
| 51 | 43 | ESI+; 418.3 |
| 52 | 43 | ESI+; 374.2 |
| 53 | 43 | ESI+; 376.4 |
| 54 | 43 | ESI+; 441.4 |
| 55 | 43 | ESI+; 414.3 |
| 56 | 43 | ESI+; 442.4 |
| 57 | 43 | ESI+; 442.5 |
| 58 | 43 | ESI+; 442.4 |
| 59 | 43 | ESI+; 376.2 |
| 60 | 43 | ESI+; 376.2 |
| 61 | 43 | ESI+; 442.3 |
| 62 | 43 | ESI+; 442.3 |

TABLE 32

| Ex | Syn | DAT |
|---|---|---|
| 63 | 43 | ESI+; 442.2 |
| 64 | 43 | ESI+; 442.3 |
| 65 | 43 | ESI+; 442.2 |
| 66 | 43 | ESI+; 460.3 |
| 67 | 43 | ESI+; 460.3 |
| 68 | 43 | ESI+; 460.3 |
| 69 | 43 | ESI+; 418.3 |
| 70 | 43 | ESI+; 460.4 |
| 71 | 43 | ESI+; 460.4 |
| 72 | 43 | ESI+; 460.4 |
| 73 | 43 | ESI+; 460.4 |
| 74 | 43 | ESI+; 448.4 |
| 75 | 43 | ESI+; 448.4 |
| 76 | 43 | ESI+; 432.4 |
| 77 | 43 | ESI+; 430.4 |
| 78 | 43 | ESI+; 460.4 |
| 79 | 43 | ESI+; 442.4 |
| 80 | 43 | ESI+; 442.4 |
| 81 | 43 | ESI+; 442.4 |
| 82 | 43 | ESI+; 442.5 |
| 83 | 43 | ESI+; 442.4 |
| 84 | 43 | ESI+; 410.4 |
| 85 | 43 | ESI+; 445.4 |
| 86 | 43 | ESI+; 384.2 |
| 87 | — | ESI+; 343.4 |
| 88 | — | ESI+; 305.9 |
| 89 | P10 | ESI+; 343.4 |
| 90 | — | ESI+; 410.4 |

TABLE 33

| Ex | Syn | DAT |
|---|---|---|
| 91 | — | ESI+; 431.2 |
| 92 | — | ESI+; 436.5 |
| 93 | 90 | ESI+; 445.6 |
| 94 | 90 | ESI+; 388.2 |
| 95 | — | ESI+; 363.0 |
| 96 | — | ESI+; 469.6 |
| 97 | 96 | ESI+; 395.1 |
| 98 | 96 | ESI+; 423.1 |
| 99 | — | ESI+; 407.3<br>¹H NMR (DMSO-d₆, 500 MHz) δ 8.13 (d, 1H, J = 1.5 Hz), 7.99 (dd, 1H, J = 1.4, 8.0 Hz), 7.44-7.55 (m, 4H), 7.31-7.37 (m, 2H), 4.31-4.39 (m, 1H), 4.15 (dt, 1H, J = 4.8, 13.6 Hz), 4.01 (ddd, 1H, J = 3.3, 8.8, 14.5 Hz), 3.92 (s, 1H), 3.66-3.74 (m, 1H), 3.13-3.28 (m, 2H), 3.08 (t, 2H, J = 5.5 Hz) |

TABLE 33-continued

| Ex | Syn | DAT |
|---|---|---|
| 100 | — | ESI+; 359.4 |
| 101 | 100 | ESI+; 359.4 |
| 102 | 1 | ESI+; 317.1 |
| 103 | 1 | ESI+; 360.3 |
| 104 | 1 | ESI+; 384.2 |
| 105 | 1 | ESI+; 422.2 |
| 106 | — | ESI+; 390.3 |
| 107 | 1 | ESI+; 390.4 |
| 108 | 1 | ESI+; 360.3 |

TABLE 34

| Ex | Syn | DAT |
|---|---|---|
| 109 | 1 | ESI+; 410.1 |
| 110 | 1 | ESI+; 419.0 |
| 111 | 1 | ESI+; 406.1 |
| 112 | 1 | ESI+; 390.1 |
| 113 | 33 | ESI+; 362.4 |
| 114 | 33 | ESI+; 441.1 |
| 115 | 33 | ESI+; 372.0 |
| 116 | 33 | ESI+; 378.1 |
| 117 | 33 | ESI+; 427.1 |
| 118 | 33 | ESI+; 378.1 |
| 119 | — | ESI+; 419.0 |
| 120 | 88 | ESI+; 333.1 |
| 121 | 88 | ESI+; 324.1 |
| 122 | 88 | ESI+; 408.4 |
| 123 | 96 | ESI+; 459.6 |
| 124 | 96 | ESI+; 483.2 |
| 125 | 99 | ESI+; 395.3 |
| 126 | 106 | ESI+; 434.0 |
| 127 | — | ESI+; 374.0 |
| 128 | — | ESI+; 438.1 |
| 129 | — | ESI+; 430.1 |
| 130 | — | ESI+; 469.2 |
| 131 | — | ESI+; 376.2 |
| 132 | 131 | ESI+; 443.2 |
| 133 | — | ESI+; 406.0 |

TABLE 35

| Ex | Syn | DAT |
|---|---|---|
| 134 | — | ESI+; 376.3<br>$^1$H NMR (DMSO-$d_6$, 500 MHz) δ 8.08 (d, 1H, J = 1.7 Hz), 7.96 (dd, 1H, J = 1.3, 7.9 Hz), 7.51 (d, 1H, J = 8.0 Hz), 7.44-7.49 (m, 3H), 7.32-7.36 (m, 2H), 5.06 (dd, 2H, J = 4.8, 9.9 Hz), 4.07-4.14 (m, 2H), 3.85 (dd, 1H, J = 5.4, 11.1 Hz), 3.57 (dd, 1H, J = 4.9, 10.7 Hz), 3.51 (dd, 1H, J = 5.7, 12.9 Hz), 3.24 (dd, 1H, J = 4.9, 12.2 Hz)<br>DSC$^1$; 133° C.<br>2θ (°) = 4.0, 8.0, 12.0, 12.7, 15.1, 16.7, 18.1, 18.9, 19.6, 22.2 |
| 135 | — | ESI+; 401.2<br>$^1$H NMR (DMSO-$d_6$, 500 MHz) δ 8.10 (d, 1H, J = 1.5 Hz), 7.97 (dd, 1H, J = 1.3, 7.9 Hz), 7.50 (d, 1H, J = 8.0 Hz), 7.44-7.49 (m, 3H), 7.30-7.36 (m, 3H), 6.83 (br s, 1H), 4.28-4.40 (m, 2H), 3.22-3.42 (m, 1H), 2.82 (dt, 1H, J = 3.1, 12.7 Hz), 2.37-2.45 (m, 1H), 1.75-1.89 (m, 2H), 1.50-1.60 (m, 1H), 1.37-1.46 (m, 1H)<br>DSC$^1$; 180° C.<br>2θ (°) = 5.7, 7.7, 13.4, 14.2, 15.4, 16.0, 16.6, 18.3, 23.7, 25.7 |
| 136 | — | ESI+; 407.2<br>$^1$H NMR (DMSO-$d_6$, 500 MHz) δ 8.13 (d, 1H, J = 1.7 Hz), 7.99 (dd, 1H, J = 1.4, 8.0 Hz), 7.53 (d, J = 8.0 Hz, 1H), 7.44-7.51 (m, 3H), 7.32-7.36 (m, 2H), 4.31-4.39 (m, 1H), 4.15 (dt, 1H, J = 4.7, 13.7 Hz), 3.97-4.05 (m, 1H), 3.92 (s, 1H), 3.66-3.74 (m, 1H), 3.13-3.28 (m, 2H), 3.08 (t, 2H, J = 5.5 Hz)<br>DSC$^1$; 97° C., 124° C., 191° C.<br>DSC$^2$; 147° C.<br>2θ (°) = 4.2, 12.5, 14.4, 14.9, 16.7, 17.1, 18.6, 19.7, 22.0, 25.4 |

INDUSTRIAL APPLICABILITY

A compound of formula (I) or a salt thereof has an inhibitory action on STING and is expected to be useful as a therapeutic drug for an autoimmune disease, a neurodegenerative disease, a type I interferonopathy and/or other STING-mediated disease.

The invention claimed is:

1. A compound of formula (I) or a salt thereof:

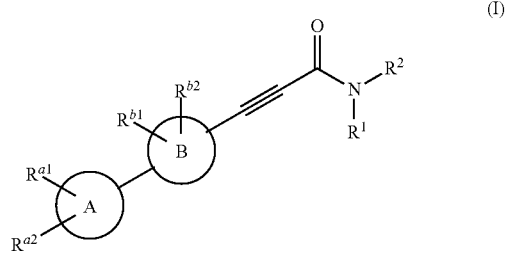

wherein,
Ring A is phenyl,
Ring B is formula (V):

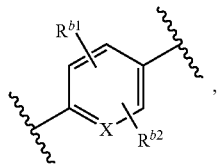

(V)

X is CH or N,
$R^{a1}$, $R^{a2}$ and $R^{b1}$ are H,
$R^{b2}$ is halogeno-$C_{1-6}$ alkyl,
$R^1$ is H,
$R^2$ is $C_{1-6}$ alkyl which is substituted by one or two $R^3$,
or, $R^1$ and $R^2$ are linked to each other to form azetidinyl, pyrrolidinyl, piperidinyl or thiomorpholinyl together with the nitrogen atom to which $R^1$ and $R^2$ are attached, wherein the azetidinyl, pyrrolidinyl, piperidinyl or thiomorpholinyl may be optionally substituted with one or two $R^7$,
each $R^3$ is independently —OH or —C(═O)—$NH_2$, and
each $R^7$ is independently —$C_{1-6}$ alkylene-OH, —OH, —C(═O)—$NH_2$, oxo or imino.

2. The compound or a salt thereof according to claim 1, wherein the compound is a compound selected from the following group of:
$N^2$-{3-[2-(trifluoromethyl)[1,1'-biphenyl]-4-yl]prop-2-ynoyl}-L-serinamide,
1-[(3R,4R)-3,4-dihydroxypyrrolidin-1-yl]-3-[2-(trifluoromethyl)[1,1'-biphenyl]-4-yl]prop-2-yn-1-one,
1-{3-[2-(trifluoromethyl)[1,1'-biphenyl]-4-yl]prop-2-ynoyl}piperidine-4-carboxamide,
1-[(3R,4S)-3,4-dihydroxypyrrolidin-1-yl]-3-[2-(trifluoromethyl)[1,1'-biphenyl]-4-yl]prop-2-yn-1-one,
1-[3,3-bis(hydroxymethyl)azetidin-1-yl]-3-[2-(trifluoromethyl)[1,1'-biphenyl]-4-yl]prop-2-yn-1-one,
N-[(2R)-2,3-dihydroxypropyl]-3-[2-(trifluoromethyl)[1,1'-biphenyl]-4-yl]prop-2-ynamide,
N-[(2S)-2,3-dihydroxypropyl]-3-[2-(trifluoromethyl)[1,1'-biphenyl]-4-yl]prop-2-ynamide,
1-[(3S,4S)-3,4-dihydroxypyrrolidin-1-yl]-3-[2-(trifluoromethyl)[1,1'-biphenyl]-4-yl]prop-2-yn-1-one,
(3R)-1-{3-[2-(trifluoromethyl)[1,1'-biphenyl]-4-yl]prop-2-ynoyl}pyrrolidine-3-carboxamide,
1-[(3R,4S)-3,4-dihydroxypyrrolidin-1-yl]-3-[6-phenyl-5-(trifluoromethyl)pyridin-3-yl]prop-2-yn-1-one, and
1-imino-4-{3-[2-(trifluoromethyl)[1,1'-biphenyl]-4-yl]prop-2-ynoyl}-1$\lambda^6$-thiomorpholin-1-one.

3. A pharmaceutical composition comprising the compound or a salt thereof according to claim 1 and one or more pharmaceutically acceptable excipients.

4. A method for therapeutic treatment of an autoimmune disease, a neurodegenerative disease, a type I interferonopathy and/or other STING-mediated disease comprising administering to a subject an effective amount of the compound or a salt thereof according to claim 1.

5. The compound or a salt thereof according to claim 2 wherein the compound is $N^2$-{3-[2-(trifluoromethyl)[1,1'-biphenyl]-4-yl]prop-2-ynoyl}-L-serinamide.

6. The compound or a salt thereof according to claim 2, wherein the compound is 1-[(3R,4R)-3,4-dihydroxypyrrolidin-1-yl]-3-[2-(trifluoromethyl)[1,1'-biphenyl]-4-yl]prop-2-yn-1-one.

7. The compound or a salt thereof according to claim 2, wherein the compound is 1-{3-[2-(trifluoromethyl)[1,1'-biphenyl]-4-yl]prop-2-ynoyl}piperidine-4-carboxamide.

8. The compound or a salt thereof according to claim 2, wherein the compound is 1-[(3R,4S)-3,4-dihydroxypyrrolidin-1-yl]-3-[2-(trifluoromethyl)[1,1'-biphenyl]-4-yl]prop-2-yn-1-one.

9. The compound or a salt thereof according to claim 2, wherein the compound is 1-[3,3-bis(hydroxymethyl)azetidin-1-yl]-3-[2-(trifluoromethyl)[1,1'-biphenyl]-4-yl]prop-2-yn-1-one.

10. The compound or a salt thereof according to claim 2, wherein the compound is N-[(2R)-2,3-dihydroxypropyl]-3-[2-(trifluoromethyl)[1,1'-biphenyl]-4-yl]prop-2-ynamide.

11. The compound or a salt thereof according to claim 2, wherein the compound is N-[(2S)-2,3-dihydroxypropyl]-3-[2-(trifluoromethyl)[1,1'-biphenyl]-4-yl]prop-2-ynamide.

12. The compound or a salt thereof according to claim 2, wherein the compound is 1-[(3S,4S)-3,4-dihydroxypyrrolidin-1-yl]-3-[2-(trifluoromethyl)[1,1'-biphenyl]-4-yl]prop-2-yn-1-one.

13. The compound or a salt thereof according to claim 2, wherein the compound is (3R)-1-{3-[2-(trifluoromethyl)[1,1'-biphenyl]-4-yl]prop-2-ynoyl}pyrrolidine-3-carboxamide.

14. The compound or a salt thereof according to claim 2, wherein the compound is 1-[(3R,4S)-3,4-dihydroxypyrrolidin-1-yl]-3-[6-phenyl-5-(trifluoromethyl)pyridin-3-yl]prop-2-yn-1-one.

15. The compound or a salt thereof according to claim 2, wherein the compound is 1-imino-4-{3-[2-(trifluoromethyl)[1,1'-biphenyl]-4-yl]prop-2-ynoyl}-1$\lambda^6$-thiomorpholin-1-one.

16. A pharmaceutical composition comprising the compound or a salt thereof according to claim 2 and one or more pharmaceutically acceptable excipients.

17. A method for therapeutic treatment of systemic lupus erythematosus and/or Sjogren's syndrome comprising administering to a subject an effective amount of the compound or a salt thereof according to claim 1.

18. A method for therapeutic treatment of an autoimmune disease, a neurodegenerative disease, a type I interferonopathy and/or other STING-mediated disease comprising administering to a subject an effective amount of the compound or a salt thereof according to claim 2.

19. A method for therapeutic treatment of systemic lupus erythematosus and/or Sjogren's syndrome comprising administering to a subject an effective amount of the compound or a salt thereof according to claim 2.

* * * * *